(12) United States Patent
Wensley et al.

(10) Patent No.: US 11,642,473 B2
(45) Date of Patent: *May 9, 2023

(54) HEATING UNIT FOR USE IN A DRUG DELIVERY DEVICE

(71) Applicant: ALEXZA PHARMACEUTICALS, INC., Mountain View, CA (US)

(72) Inventors: Martin J. Wensley, Los Gatos, CA (US); Marc Glazer, Sunnyvale, CA (US); James Bresson, Los Altos, CA (US); Ryan Timmons, Mountain View, CA (US); Daniel J. Myers, Mountain View, CA (US)

(73) Assignee: ALEXZA PHARMACEUTICALS, INC., Palo Alto, CA (US)

( * ) Notice: Subject to any disclaimer, the term of this patent is extended or adjusted under 35 U.S.C. 154(b) by 400 days.

This patent is subject to a terminal disclaimer.

(21) Appl. No.: 16/853,400

(22) Filed: Apr. 20, 2020

(65) Prior Publication Data

US 2020/0246559 A1 Aug. 6, 2020

Related U.S. Application Data

(63) Continuation of application No. 15/289,772, filed on Oct. 10, 2016, now Pat. No. 10,625,033, which is a (Continued)

(51) Int. Cl.
*A61M 11/00* (2006.01)
*A61M 11/04* (2006.01)
(Continued)

(52) U.S. Cl.
CPC .......... *A61M 11/042* (2014.02); *A61K 9/007* (2013.01); *A61K 9/0009* (2013.01); *A61K 9/12* (2013.01);
(Continued)

(58) Field of Classification Search
CPC .............. A61M 11/042; A61M 11/001; A61M 15/0015; A61M 11/041; A61M 15/00; A61M 15/06; A61M 11/047; A61M 2205/3653; A61M 2205/8268; A61K 9/0009; A61K 9/007; A61K 9/12; A61K 31/135; A61K 31/138; A61K 31/196; A61K 31/197; A61K 31/433
See application file for complete search history.

(56) References Cited

U.S. PATENT DOCUMENTS 1,239,634 A 9/1917 Stuart
1,514,682 A 11/1924 Wilson
(Continued)

FOREIGN PATENT DOCUMENTS

CA 2152684 1/1996
CH 436 297 5/1967
(Continued)

OTHER PUBLICATIONS

U.S. Appl. No. 11/687,466, filed Mar. 16, 2007, Zaffaroni.
(Continued)

*Primary Examiner* — Steven O Douglas
(74) *Attorney, Agent, or Firm* — Adsero IP

(57) ABSTRACT

Drug supply units are disclosed which comprise substrates having a plurality of holes formed therein.

14 Claims, 18 Drawing Sheets

Related U.S. Application Data continuation of application No. 12/045,674, filed on Mar. 10, 2008, now abandoned.

(60) Provisional application No. 60/894,116, filed on Mar. 9, 2007.

(51) Int. Cl.

| | | |
|---|---|---|
| *A61M 15/06* | (2006.01) | |
| *A61K 9/12* | (2006.01) | |
| *A61K 9/00* | (2006.01) | |
| *A61M 15/00* | (2006.01) | |
| *A61K 31/135* | (2006.01) | |
| *A61K 31/138* | (2006.01) | |
| *A61K 31/196* | (2006.01) | |
| *A61K 31/197* | (2006.01) | |
| *A61K 31/433* | (2006.01) | |
| *A61K 31/4468* | (2006.01) | |
| *A61K 31/451* | (2006.01) | |
| *A61K 31/4525* | (2006.01) | |
| *A61K 31/4985* | (2006.01) | |
| *A61K 31/519* | (2006.01) | |
| *A61K 31/53* | (2006.01) | |
| *A61K 31/5415* | (2006.01) | |
| *A61K 31/56* | (2006.01) | |
| *A61K 31/573* | (2006.01) | |
| *A61K 31/58* | (2006.01) | |
| *A61K 31/7076* | (2006.01) | |

(52) U.S. Cl.
CPC .......... *A61K 31/135* (2013.01); *A61K 31/138* (2013.01); *A61K 31/196* (2013.01); *A61K 31/197* (2013.01); *A61K 31/433* (2013.01); *A61K 31/4468* (2013.01); *A61K 31/451* (2013.01); *A61K 31/4525* (2013.01); *A61K 31/4985* (2013.01); *A61K 31/519* (2013.01); *A61K 31/53* (2013.01); *A61K 31/5415* (2013.01); *A61K 31/56* (2013.01); *A61K 31/573* (2013.01); *A61K 31/58* (2013.01); *A61K 31/7076* (2013.01); *A61M 11/001* (2014.02); *A61M 11/041* (2013.01); *A61M 15/00* (2013.01); *A61M 15/0015* (2014.02); *A61M 15/06* (2013.01); *A61M 11/047* (2014.02); *A61M 2205/3653* (2013.01); *A61M 2205/8268* (2013.01)

(56) References Cited

U.S. PATENT DOCUMENTS

| | | |
|---|---|---|
| 1,535,486 A | 4/1925 | Lundy |
| 1,803,334 A | 5/1931 | Lehmann |
| 1,864,980 A | 6/1932 | Curran |
| 2,084,299 A | 6/1937 | Borden |
| 2,086,140 A | 7/1937 | Silten |
| 2,230,753 A | 2/1941 | Klavehn |
| 2,230,754 A | 2/1941 | Klavehn |
| 2,243,669 A | 5/1941 | Clyne |
| 2,309,846 A | 2/1943 | Holm |
| 2,469,656 A | 5/1949 | Lienert |
| 2,714,649 A | 8/1955 | Critzer |
| 2,741,812 A | 4/1956 | Andre |
| 2,761,055 A | 8/1956 | Ike |
| 2,887,106 A | 5/1959 | Robinson |
| 2,898,649 A | 8/1959 | Murray |
| 2,902,484 A | 9/1959 | Horclois |
| 3,043,977 A | 7/1962 | Morowitz |
| 3,080,624 A | 3/1963 | Webber, III |
| 3,161,478 A | 12/1964 | Chessin |
| 3,164,600 A | 1/1965 | Janssen |
| 3,169,095 A | 2/1965 | Thiel |
| 3,200,819 A | 8/1965 | Gilbert |
| 3,219,533 A | 11/1965 | Mullins |
| 3,282,729 A | 11/1966 | Richardson |
| 3,296,249 A | 1/1967 | Bell |
| 3,299,185 A | 1/1967 | Oda |
| 3,371,085 A | 2/1968 | Reeder |
| 3,393,197 A | 7/1968 | Pachter |
| 3,433,791 A | 3/1969 | Bentley |
| 3,560,607 A | 2/1971 | Hartley |
| 3,701,782 A | 10/1972 | Hester |
| 3,749,547 A | 7/1973 | Gregory |
| 3,763,347 A | 10/1973 | Whitaker |
| 3,773,955 A | 11/1973 | Pachter |
| 3,831,606 A | 8/1974 | Damani |
| 3,847,650 A | 11/1974 | Gregory |
| 3,864,326 A | 2/1975 | Babington |
| 3,882,323 A | 5/1975 | Smolker |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick |
| 4,020,379 A | 4/1977 | Manning |
| 4,045,156 A | 8/1977 | Chu |
| 4,079,742 A | 3/1978 | Rainer |
| 4,104,210 A | 8/1978 | Coran |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline |
| 4,181,757 A | 1/1980 | Youdelis |
| 4,183,912 A | 1/1980 | Rosenthale |
| 4,184,099 A | 1/1980 | Lindauer |
| 4,189,200 A | 2/1980 | Yeager |
| 4,190,654 A | 2/1980 | Gherardi |
| 4,198,200 A | 4/1980 | Fonda |
| RE30,285 E | 5/1980 | Babington |
| 4,219,031 A | 8/1980 | Rainer |
| 4,229,447 A | 10/1980 | Porter |
| 4,229,931 A | 10/1980 | Schlueter |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann |
| 4,291,758 A | 9/1981 | Fujii |
| 4,303,083 A | 12/1981 | Burruss, Jr. |
| 4,340,072 A | 7/1982 | Bolt |
| 4,346,059 A | 8/1982 | Spector |
| 4,347,855 A | 9/1982 | Lanzillotti |
| 4,376,767 A | 3/1983 | Sloan |
| 4,391,285 A | 7/1983 | Burnett |
| 4,419,302 A | 12/1983 | Nishino |
| 4,419,650 A | 12/1983 | John |
| 4,423,071 A | 12/1983 | Chignac |
| 4,474,191 A | 10/1984 | Steiner |
| 4,484,576 A | 11/1984 | Albarda |
| 4,484,577 A | 11/1984 | Sackner et al. |
| 4,508,726 A | 4/1985 | Coleman |
| 4,523,589 A | 6/1985 | Krauser |
| 4,539,575 A | 9/1985 | Nilsson |
| 4,556,539 A | 12/1985 | Spector |
| 4,566,451 A | 1/1986 | Badewien |
| 4,588,425 A | 5/1986 | Usry |
| 4,588,721 A | 5/1986 | Mahan |
| 4,591,615 A | 5/1986 | Aldred |
| 4,605,552 A | 8/1986 | Fritschi |
| 4,617,232 A | 10/1986 | Chandler |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III |

(56) References Cited

U.S. PATENT DOCUMENTS

| | | |
|---|---|---|
| 4,683,231 A | 7/1987 | Glassman |
| 4,693,868 A | 9/1987 | Katsuda |
| 4,708,151 A | 11/1987 | Shelar |
| 4,714,082 A | 12/1987 | Banerjee |
| 4,722,334 A | 2/1988 | Blackmer |
| 4,734,560 A | 3/1988 | Bowen |
| 4,735,217 A | 4/1988 | Gerth |
| 4,735,358 A | 4/1988 | Morita |
| 4,753,758 A | 6/1988 | Miller |
| 4,755,508 A | 7/1988 | Bock |
| 4,756,318 A | 7/1988 | Clearman |
| 4,765,347 A | 8/1988 | Sensabaugh, Jr. |
| 4,771,795 A | 9/1988 | White |
| 4,774,971 A | 10/1988 | Vieten |
| 4,793,365 A | 12/1988 | Sensabaugh, Jr. |
| 4,793,366 A | 12/1988 | Hill |
| 4,800,903 A | 1/1989 | Ray |
| 4,801,411 A | 1/1989 | Wellinghoff |
| 4,814,161 A | 3/1989 | Jinks |
| 4,819,665 A | 4/1989 | Roberts |
| 4,848,374 A | 7/1989 | Chard |
| 4,852,561 A | 8/1989 | Sperry |
| 4,853,517 A | 8/1989 | Bowen |
| 4,854,331 A | 8/1989 | Banerjee |
| 4,858,630 A | 8/1989 | Banerjee |
| 4,863,720 A | 9/1989 | Burghart |
| 4,881,541 A | 11/1989 | Eger |
| 4,881,556 A | 11/1989 | Clearman |
| 4,889,850 A | 12/1989 | Thornfeldt |
| 4,892,109 A | 1/1990 | Strubel |
| 4,895,719 A | 1/1990 | Radhakrishnun |
| 4,906,417 A | 3/1990 | Gentry |
| 4,911,157 A | 3/1990 | Miller |
| 4,917,119 A | 4/1990 | Potter |
| 4,917,120 A | 4/1990 | Hill |
| 4,917,830 A | 4/1990 | Ortiz |
| 4,922,901 A | 5/1990 | Brooks et al. |
| 4,924,883 A | 5/1990 | Perfetti |
| 4,928,714 A | 5/1990 | Shannon |
| 4,935,073 A | 6/1990 | Bartlett |
| 4,935,624 A | 6/1990 | Henion |
| 4,941,483 A | 7/1990 | Ridings |
| 4,947,874 A | 8/1990 | Brooks et al. |
| 4,947,875 A | 8/1990 | Brooks et al. |
| 4,950,664 A | 8/1990 | Goldberg |
| 4,955,945 A | 9/1990 | Weick |
| 4,959,380 A | 9/1990 | Wilson |
| 4,963,289 A | 10/1990 | Ortiz |
| 4,968,885 A | 11/1990 | Willoughby |
| 4,984,158 A | 1/1991 | Hillsman |
| 4,989,619 A | 2/1991 | Clearman et al. |
| 5,016,425 A | 5/1991 | Weick |
| 5,017,575 A | 5/1991 | Golwyn |
| 5,019,122 A | 5/1991 | Clearman |
| 5,020,548 A | 6/1991 | Farrier |
| 5,027,836 A | 7/1991 | Shannon |
| 5,033,483 A | 7/1991 | Clearman |
| 5,038,769 A | 8/1991 | Krauser |
| 5,042,509 A | 8/1991 | Banerjee |
| 5,049,389 A | 9/1991 | Radhakrishnun |
| 5,060,666 A | 10/1991 | Clearman |
| 5,060,667 A | 10/1991 | Strubel |
| 5,060,671 A | 10/1991 | Counts |
| 5,067,499 A | 11/1991 | Banerjee |
| 5,072,726 A | 12/1991 | Mazloomdoost |
| 5,076,292 A | 12/1991 | Sensabaugh, Jr. |
| 5,082,668 A | 1/1992 | Wong |
| 5,093,894 A | 3/1992 | Deevi |
| 5,095,921 A | 3/1992 | Loose |
| 5,099,861 A | 3/1992 | Clearman |
| 5,105,831 A | 4/1992 | Banerjee |
| 5,109,180 A | 4/1992 | Boultinghouse |
| 5,112,598 A | 5/1992 | Biesalski |
| 5,118,494 A | 6/1992 | Schultz |
| 5,119,834 A | 6/1992 | Shannon |
| 5,126,123 A | 6/1992 | Johnson |
| 5,133,368 A | 7/1992 | Neumann |
| 5,135,009 A | 8/1992 | Muller |
| 5,137,034 A | 8/1992 | Perfetti |
| 5,144,962 A | 9/1992 | Counts |
| 5,146,915 A | 9/1992 | Montgomery |
| 5,149,538 A | 9/1992 | Granger |
| 5,156,170 A | 10/1992 | Clearman |
| 5,160,664 A | 11/1992 | Liu |
| 5,164,740 A | 11/1992 | Ivri |
| 5,166,202 A | 11/1992 | Schweizer |
| 5,167,242 A | 12/1992 | Turner |
| 5,168,866 A | 12/1992 | Montgomery |
| 5,177,071 A | 1/1993 | Freidinger |
| 5,179,966 A | 1/1993 | Losee |
| 5,186,164 A | 2/1993 | Raghuprasad |
| 5,192,548 A | 3/1993 | Velasquez |
| 5,224,498 A | 7/1993 | Deevi et al. |
| 5,226,411 A | 7/1993 | Levine |
| 5,229,120 A | 7/1993 | DeVincent |
| 5,229,382 A | 7/1993 | Chakrabarti |
| 5,240,922 A | 8/1993 | O'Neill |
| 5,249,586 A | 10/1993 | Morgan |
| 5,255,674 A | 10/1993 | Oftedal |
| 5,261,424 A | 11/1993 | Sprin |
| 5,264,433 A | 11/1993 | Sato |
| 5,269,327 A | 12/1993 | Counts |
| 5,284,133 A | 2/1994 | Burns |
| 5,285,798 A | 2/1994 | Banerjee |
| 5,292,499 A | 3/1994 | Evans |
| 5,322,075 A | 6/1994 | Deevi |
| 5,333,106 A | 7/1994 | Lanpher |
| 5,345,951 A | 9/1994 | Serrano |
| 5,357,984 A | 10/1994 | Farrier |
| 5,363,842 A | 11/1994 | Mishelevich |
| 5,364,838 A | 11/1994 | Rubsamen |
| 5,366,770 A | 11/1994 | Wang |
| 5,369,723 A | 11/1994 | Counts |
| 5,372,148 A | 12/1994 | McCafferty |
| 5,376,386 A | 12/1994 | Ganderton |
| 5,388,574 A | 2/1995 | Ingebrethsen |
| 5,391,081 A | 2/1995 | Lampotang |
| 5,397,652 A | 3/1995 | Carey |
| 5,399,574 A | 3/1995 | Robertson |
| 5,400,808 A | 3/1995 | Turner |
| 5,400,969 A | 3/1995 | Keene |
| 5,402,517 A | 3/1995 | Gillett |
| 5,408,574 A | 4/1995 | Deevi |
| 5,431,167 A | 7/1995 | Savord |
| 5,436,230 A | 7/1995 | Soudant |
| 5,451,408 A | 9/1995 | Mezei |
| 5,455,043 A | 10/1995 | Fischel-Ghodsian |
| 5,456,247 A | 10/1995 | Shilling |
| 5,456,677 A | 10/1995 | Spector |
| 5,457,100 A | 10/1995 | Daniel |
| 5,457,101 A | 10/1995 | Greenwood |
| 5,459,137 A | 10/1995 | Andrasi |
| 5,462,740 A | 10/1995 | Evenstad |
| 5,468,936 A | 11/1995 | Deevi |
| 5,479,948 A | 1/1996 | Counts |
| 5,496,359 A | 3/1996 | Davidson |
| 5,501,236 A | 3/1996 | Hill |
| 5,505,214 A | 4/1996 | Collins |
| 5,507,277 A | 4/1996 | Rubsamen |
| 5,511,726 A | 4/1996 | Greenspan |
| 5,518,179 A | 5/1996 | Humberstone et al. |
| 5,519,019 A | 5/1996 | Andrasi |
| 5,554,646 A | 5/1996 | Lloyd et al. |
| 5,522,385 A | 6/1996 | Lloyd |
| 5,525,329 A | 6/1996 | Snyder |
| 5,537,507 A | 7/1996 | Mariner |
| 5,538,020 A | 7/1996 | Farrier |
| 5,540,959 A | 7/1996 | Wang |
| 5,543,434 A | 8/1996 | Weg |
| 5,544,646 A | 8/1996 | Lloyd |
| 5,564,442 A | 10/1996 | MacDonald |
| 5,565,148 A | 10/1996 | Pendergrass |
| 5,577,156 A | 11/1996 | Costello |
| 5,584,701 A | 12/1996 | Lampotang |

(56) References Cited

U.S. PATENT DOCUMENTS

| | | |
|---|---|---|
| 5,586,550 A | 12/1996 | Ivri |
| 5,591,409 A | 1/1997 | Watkins |
| 5,592,934 A | 1/1997 | Thwaites |
| 5,593,792 A | 1/1997 | Farrier |
| 5,605,146 A | 2/1997 | Sarela |
| 5,605,897 A | 2/1997 | Beasley, Jr. |
| 5,607,691 A | 3/1997 | Hale |
| 5,613,504 A | 3/1997 | Collins |
| 5,613,505 A | 3/1997 | Campbell |
| 5,619,984 A | 4/1997 | Hodson |
| 5,622,944 A | 4/1997 | Hale |
| 5,627,178 A | 5/1997 | Chakrabarti |
| 5,641,938 A | 6/1997 | Holland |
| 5,649,554 A | 7/1997 | Sprinkel |
| 5,655,523 A | 8/1997 | Hodson |
| 5,656,255 A | 8/1997 | Jones |
| 5,660,166 A | 8/1997 | Lloyd |
| 5,666,977 A | 9/1997 | Higgins |
| 5,690,809 A | 11/1997 | Subramaniam |
| 5,694,919 A | 12/1997 | Rubsamen et al. |
| 5,718,222 A | 2/1998 | Lloyd |
| 5,724,957 A | 3/1998 | Rubsamen |
| 5,725,756 A | 3/1998 | Subramaniam |
| 5,733,572 A | 3/1998 | Unger |
| 5,735,263 A | 4/1998 | Rubsamen et al. |
| 5,738,865 A | 4/1998 | Baichwal |
| 5,743,250 A | 4/1998 | Gonda |
| 5,743,251 A | 4/1998 | Howell |
| 5,744,469 A | 4/1998 | Tran |
| 5,747,001 A | 5/1998 | Wiedmann |
| 5,756,449 A | 5/1998 | Andersen |
| 5,758,637 A | 6/1998 | Ivri |
| 5,767,117 A | 6/1998 | Moskowitz |
| 5,769,621 A | 6/1998 | Early |
| 5,770,222 A | 6/1998 | Unger |
| 5,771,882 A | 6/1998 | Psaros |
| 5,776,928 A | 7/1998 | Beasley, Jr. |
| 5,804,212 A | 9/1998 | Ilium |
| 5,809,997 A | 9/1998 | Wolf |
| 5,817,656 A | 10/1998 | Beasley, Jr. |
| 5,819,756 A | 10/1998 | Mielordt |
| 5,823,178 A | 10/1998 | Lloyd |
| 5,829,436 A | 11/1998 | Rubsamen |
| 5,833,891 A | 11/1998 | Subramaniam |
| 5,840,246 A | 11/1998 | Hammons |
| 5,855,564 A | 1/1999 | Ruskewicz |
| 5,855,913 A | 1/1999 | Hanes |
| 5,858,118 A | 1/1999 | Shah |
| 5,865,185 A | 2/1999 | Collins |
| 5,874,064 A | 2/1999 | Edwards |
| 5,874,481 A | 2/1999 | Weers |
| 5,875,776 A | 3/1999 | Vaghefi |
| 5,878,752 A | 3/1999 | Adams et al. |
| 5,884,620 A | 3/1999 | Gonda |
| 5,890,908 A | 4/1999 | Lampotang |
| 5,894,841 A | 4/1999 | Voges |
| 5,900,249 A | 5/1999 | Smith |
| 5,904,900 A | 5/1999 | Bleuse |
| 5,906,811 A | 5/1999 | Hersh |
| 5,907,075 A | 5/1999 | Subramaniam |
| 5,910,301 A | 6/1999 | Farr |
| 5,915,378 A | 6/1999 | Lloyd et al. |
| 5,918,595 A | 7/1999 | Olsson |
| 5,928,520 A | 7/1999 | Haumesser |
| 5,929,093 A | 7/1999 | Pang |
| 5,934,272 A | 8/1999 | Lloyd et al. |
| 5,934,289 A | 8/1999 | Watkins |
| 5,935,604 A | 8/1999 | Ilium |
| 5,938,117 A | 8/1999 | Ivri |
| 5,939,100 A | 8/1999 | Albrechtsen |
| 5,941,240 A | 8/1999 | Gonda |
| 5,944,012 A | 8/1999 | Pera |
| 5,957,124 A | 9/1999 | Lloyd et al. |
| 5,960,792 A | 10/1999 | Lloyd et al. |
| 5,970,973 A | 10/1999 | Gonda |
| 5,971,951 A | 10/1999 | Ruskewicz |
| 5,980,566 A | 11/1999 | Alt |
| 5,985,309 A | 11/1999 | Edwards |
| 5,993,805 A | 11/1999 | Sutton |
| 6,004,516 A | 12/1999 | Rasouli |
| 6,004,970 A | 12/1999 | O'Malley |
| 6,008,214 A | 12/1999 | Kwon |
| 6,008,216 A | 12/1999 | Chakrabarti |
| 6,013,050 A | 1/2000 | Bellhouse |
| 6,014,969 A | 1/2000 | Lloyd |
| 6,014,970 A | 1/2000 | Ivri et al. |
| 6,041,777 A | 3/2000 | Faithfull |
| 6,044,777 A | 4/2000 | Walsh |
| 6,048,550 A | 4/2000 | Chan |
| 6,048,857 A | 4/2000 | Ellinwood, Jr. |
| 6,050,260 A | 4/2000 | Daniell |
| 6,051,257 A | 4/2000 | Kodas |
| 6,051,566 A | 4/2000 | Bianco |
| 6,053,176 A | 4/2000 | Adams |
| RE36,744 E | 6/2000 | Goldberg |
| 6,085,026 A | 7/2000 | Hammons |
| 6,089,857 A | 7/2000 | Matsuura |
| 6,090,212 A | 7/2000 | Mahawili |
| 6,090,403 A | 7/2000 | Block et al. |
| 6,095,134 A | 8/2000 | Sievers |
| 6,095,153 A | 8/2000 | Kessler et al. |
| 6,098,620 A | 8/2000 | Lloyd |
| 6,102,036 A | 8/2000 | Slutsky et al. |
| 6,113,795 A | 9/2000 | Subramaniam |
| 6,117,866 A | 9/2000 | Bondinell |
| 6,125,853 A | 10/2000 | Susa |
| 6,126,919 A | 10/2000 | Stefely |
| 6,131,566 A | 10/2000 | Ashurst |
| 6,131,570 A | 10/2000 | Schuster |
| 6,133,327 A | 10/2000 | Kimura |
| 6,135,369 A | 10/2000 | Prendergast |
| 6,136,295 A | 10/2000 | Edwards |
| 6,138,683 A | 10/2000 | Hersh |
| 6,140,323 A | 10/2000 | Ellinwood, Jr. |
| 6,143,277 A | 11/2000 | Ashurst |
| 6,143,746 A | 11/2000 | Daugan |
| 6,149,892 A | 11/2000 | Britto |
| 6,155,268 A | 12/2000 | Takeuchi |
| 6,158,431 A | 12/2000 | Poole |
| 6,167,880 B1 | 1/2001 | Gonda |
| 6,178,969 B1 | 1/2001 | St. Charles |
| 6,211,171 B1 | 4/2001 | Sawynok |
| 6,228,445 B1 | 5/2001 | Tverberg |
| 6,234,167 B1 | 5/2001 | Cox |
| 6,241,969 B1 | 6/2001 | Saidi |
| 6,250,298 B1 | 6/2001 | Gonda |
| 6,250,301 B1 | 6/2001 | Pate |
| 6,255,334 B1 | 7/2001 | Sands |
| 6,263,872 B1 | 7/2001 | Schuster |
| 6,264,922 B1 | 7/2001 | Wood |
| 6,284,287 B1 | 9/2001 | Sarlikiotis |
| 6,290,986 B1 | 9/2001 | Murdock |
| 6,299,900 B1 | 10/2001 | Reed |
| 6,300,710 B1 | 10/2001 | Nakamori |
| 6,306,431 B1 | 10/2001 | Zhang |
| 6,309,668 B1 | 10/2001 | Bastin |
| 6,309,986 B1 | 10/2001 | Flashinski |
| 6,313,176 B1 | 11/2001 | Ellinwood, Jr. |
| 6,315,985 B1 | 11/2001 | Wu |
| 6,325,475 B1 | 12/2001 | Hayes |
| 6,328,033 B1 | 12/2001 | Avrahami |
| 6,367,481 B1 | 4/2002 | Nichols |
| 6,376,550 B1 | 4/2002 | Raber |
| 6,390,453 B1 | 5/2002 | Frederickson |
| 6,408,854 B1 | 6/2002 | Gonda |
| 6,413,930 B1 | 7/2002 | Ratti |
| 6,420,351 B1 | 7/2002 | Tsai |
| 6,431,166 B2 | 8/2002 | Gonda |
| 6,443,152 B1 | 9/2002 | Lockhart |
| 6,444,326 B1 | 9/2002 | Smith |
| 6,444,665 B1 | 9/2002 | Helton |
| 6,461,591 B1 | 10/2002 | Keller |
| 6,479,074 B2 | 11/2002 | Murdock |
| 6,491,233 B2 | 12/2002 | Nichols |

(56) References Cited

U.S. PATENT DOCUMENTS

| | | |
|---|---|---|
| 6,501,052 B2 | 12/2002 | Cox |
| 6,506,762 B1 | 1/2003 | Horvath |
| 6,514,482 B1 | 2/2003 | Bartus |
| 6,516,796 B1 | 2/2003 | Cox |
| 6,521,187 B1 | 2/2003 | Papen |
| 6,550,691 B2 | 4/2003 | Pence |
| 6,554,201 B2 | 4/2003 | Klimowicz |
| 6,557,552 B1 | 5/2003 | Cox |
| 6,561,186 B2 | 5/2003 | Casper |
| 6,568,390 B2 | 5/2003 | Nichols |
| 6,591,839 B2 | 7/2003 | Meyer |
| 6,632,047 B2 | 10/2003 | Vinegar |
| 6,638,981 B2 | 10/2003 | Williams |
| 6,648,950 B2 | 11/2003 | Lee |
| 6,671,945 B2 | 1/2004 | Gerber |
| 6,680,668 B2 | 1/2004 | Gerber |
| 6,681,769 B2 | 1/2004 | Sprinkel |
| 6,681,998 B2 | 1/2004 | Sharpe et al. |
| 6,682,716 B2 | 1/2004 | Hodges et al. |
| 6,684,880 B2 | 2/2004 | Trueba |
| 6,688,313 B2 | 2/2004 | Wrenn |
| 6,694,975 B2 | 2/2004 | Schuster |
| 6,701,921 B2 | 3/2004 | Sprinkel |
| 6,701,922 B2 | 3/2004 | Hindle |
| 6,709,739 B1 | 3/2004 | Mullen |
| 6,715,487 B2 | 4/2004 | Nichols |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,728,478 B2 | 4/2004 | Cox |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,772,757 B2 | 8/2004 | Sprinkel, Jr. |
| 6,776,978 B2 | 8/2004 | Rabinowitz et al. |
| 6,779,520 B2 | 8/2004 | Genova |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,812,432 B1 | 11/2004 | Haluschka |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,979,437 B2 | 12/2005 | Bartus |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,040,314 B2 | 5/2006 | Nguyen |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,066,398 B2 | 6/2006 | Borland |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,088,914 B2 | 8/2006 | Whittle |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,364,897 B2 | 4/2008 | Heaney et al. |
| 7,387,788 B1 | 6/2008 | Carrara |
| 7,402,777 B2 | 7/2008 | Hale et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,459,469 B2 | 12/2008 | Munoz |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,494,344 B2 | 2/2009 | Galauner et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,785,482 B2 | 8/2010 | Subramanian |
| 7,832,655 B2 | 11/2010 | Tollens et al. |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 7,981,401 B2 | 7/2011 | Every et al. |
| 7,987,846 B2 | 8/2011 | Hale et al. |
| 7,988,952 B2 | 8/2011 | Rabinowitz et al. |
| 8,003,080 B2 | 8/2011 | Rabinowitz et al. |
| 8,074,644 B2 | 12/2011 | Hale et al. |
| 8,173,107 B2 | 5/2012 | Rabinowitz et al. |
| 8,235,037 B2 | 8/2012 | Hale et al. |
| 8,288,372 B2 | 10/2012 | Hale et al. |
| 8,333,197 B2 | 12/2012 | Cross et al. |
| 8,387,612 B2 | 3/2013 | Damani et al. |
| 8,425,704 B2 | 4/2013 | Currano |
| 8,506,935 B2 | 8/2013 | Hale et al. |

(56) References Cited

U.S. PATENT DOCUMENTS

| | | |
|---|---|---|
| 8,684,980 B2 | 4/2014 | Hunter et al. |
| 8,955,512 B2 | 2/2015 | Hale et al. |
| 8,991,387 B2 | 3/2015 | Damani et al. |
| 9,211,382 B2 | 12/2015 | Hale et al. |
| 9,308,208 B2 | 4/2016 | Wensley |
| 9,370,629 B2 | 6/2016 | Damani |
| 9,439,907 B2 | 9/2016 | Hale et al. |
| 9,440,034 B2 | 9/2016 | Hale et al. |
| 9,687,487 B2 | 6/2017 | Hodges |
| 9,724,341 B2 | 8/2017 | Myers |
| 9,763,476 B2 | 9/2017 | Flick |
| 10,166,224 B2 | 1/2019 | Myers |
| 10,625,033 B2 | 4/2020 | Wensley |
| 10,786,635 B2 | 9/2020 | Sharma |
| 2001/0020147 A1 | 9/2001 | Staniforth |
| 2001/0039262 A1 | 11/2001 | Venkataraman |
| 2001/0042546 A1 | 11/2001 | Umeda |
| 2002/0031480 A1 | 3/2002 | Peart |
| 2002/0037828 A1 | 3/2002 | Wilson |
| 2002/0058009 A1 | 5/2002 | Bartus |
| 2002/0061281 A1 | 5/2002 | Osbakken |
| 2002/0078955 A1 | 6/2002 | Nichols |
| 2002/0086852 A1 | 7/2002 | Cantor |
| 2002/0097139 A1 | 7/2002 | Gerber |
| 2002/0112723 A1 | 8/2002 | Schuster |
| 2002/0117175 A1 | 8/2002 | Kottayil |
| 2002/0176841 A1 | 11/2002 | Barker |
| 2003/0004142 A1 | 1/2003 | Prior |
| 2003/0015196 A1 | 1/2003 | Hodges |
| 2003/0015197 A1 | 1/2003 | Hale |
| 2003/0032638 A1 | 2/2003 | Kim et al. |
| 2003/0033055 A1 | 2/2003 | McRae |
| 2003/0049025 A1 | 3/2003 | Neumann |
| 2003/0051728 A1 | 3/2003 | Lloyd et al. |
| 2003/0062042 A1 | 4/2003 | Wensley |
| 2003/0106551 A1 | 6/2003 | Sprinkel |
| 2003/0118512 A1 | 6/2003 | Shen |
| 2003/0121906 A1 | 7/2003 | Abbott |
| 2003/0131843 A1 | 7/2003 | Lu |
| 2003/0132219 A1 | 7/2003 | Cox |
| 2003/0138508 A1 | 7/2003 | Novack et al. |
| 2003/0156829 A1 | 8/2003 | Cox |
| 2003/0209240 A1 | 11/2003 | Hale et al. |
| 2004/0009128 A1 | 1/2004 | Rabinowitz |
| 2004/0016427 A1 | 1/2004 | Byron |
| 2004/0035409 A1 | 2/2004 | Harwig |
| 2004/0055504 A1 | 3/2004 | Lee |
| 2004/0081624 A1 | 4/2004 | Nguyen |
| 2004/0096402 A1 | 5/2004 | Hodges et al. |
| 2004/0099266 A1 | 5/2004 | Cross |
| 2004/0099269 A1 | 5/2004 | Hale |
| 2004/0101481 A1 | 5/2004 | Hale et al. |
| 2004/0102434 A1 | 5/2004 | Hale |
| 2004/0105818 A1 | 6/2004 | Every et al. |
| 2004/0105819 A1 | 6/2004 | Hale |
| 2004/0170571 A1 | 9/2004 | Rabinowitz |
| 2004/0191322 A1 | 9/2004 | Hansson |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0121024 A1 | 6/2005 | Langford |
| 2005/0126562 A1 | 6/2005 | Rabinowitz et al. |
| 2005/0131739 A1 | 6/2005 | Rabinowitz et al. |
| 2005/0268911 A1 | 12/2005 | Cross |
| 2006/0032496 A1 | 2/2006 | Hale et al. |
| 2006/0032501 A1 | 2/2006 | Hale et al. |
| 2006/0120962 A1 | 6/2006 | Rabinowitz et al. |
| 2006/0193788 A1 | 8/2006 | Hale et al. |
| 2006/0216243 A1 | 9/2006 | Rabinowitz |
| 2006/0216244 A1 | 9/2006 | Rabinowitz |
| 2006/0233717 A1 | 10/2006 | Hale |
| 2006/0233719 A1 | 10/2006 | Rabinowitz |
| 2006/0239936 A1 | 10/2006 | Rabinowitz |
| 2006/0246011 A1 | 11/2006 | Rabinowitz |
| 2006/0246012 A1 | 11/2006 | Rabinowitz |
| 2006/0257328 A1 | 11/2006 | Rabinowitz |
| 2006/0257329 A1 | 11/2006 | Rabinowitz et al. |
| 2006/0269486 A1 | 11/2006 | Rabinowitz |
| 2006/0269487 A1 | 11/2006 | Rabinowitz |
| 2006/0280692 A1 | 12/2006 | Rabinowitz |
| 2006/0286043 A1 | 12/2006 | Rabinowitz |
| 2007/0014737 A1 | 1/2007 | Rabinowitz |
| 2007/0028916 A1 | 2/2007 | Hale |
| 2007/0031340 A1 | 2/2007 | Hale |
| 2007/0122353 A1 | 5/2007 | Hale et al. |
| 2007/0140982 A1 | 6/2007 | Every |
| 2007/0178052 A1 | 8/2007 | Rabinowitz |
| 2007/0286816 A1 | 12/2007 | Hale et al. |
| 2008/0038363 A1 | 2/2008 | Zaffaroni |
| 2008/0110454 A1 | 5/2008 | White |
| 2008/0110872 A1 | 5/2008 | Hale |
| 2008/0175796 A1 | 7/2008 | Rabinowitz |
| 2008/0210225 A1 | 9/2008 | Geiger |
| 2008/0216828 A1 | 9/2008 | Wensley |
| 2008/0257345 A1 | 10/2008 | Snyder |
| 2008/0299048 A1 | 12/2008 | Hale et al. |
| 2008/0306285 A1 | 12/2008 | Hale et al. |
| 2008/0308096 A1 | 12/2008 | Borgschulte et al. |
| 2008/0311176 A1 | 12/2008 | Hale |
| 2009/0062254 A1 | 3/2009 | Hale et al. |
| 2009/0071477 A1 | 3/2009 | Hale |
| 2009/0180968 A1 | 7/2009 | Hale et al. |
| 2009/0229600 A1 | 9/2009 | Hale |
| 2009/0235926 A1 | 9/2009 | Cross |
| 2009/0246147 A1 | 10/2009 | Rabinowitz |
| 2009/0258075 A1 | 10/2009 | Hale |
| 2009/0301363 A1 | 12/2009 | Damani |
| 2010/0006092 A1 | 1/2010 | Hale et al. |
| 2010/0055048 A1 | 3/2010 | Hale et al. |
| 2010/0065052 A1 | 3/2010 | Sharma et al. |
| 2010/0068155 A1 | 3/2010 | Lei et al. |
| 2010/0160240 A1 | 6/2010 | Gurd |
| 2010/0163020 A1 | 7/2010 | Hyde |
| 2010/0181387 A1 | 7/2010 | Zaffaroni et al. |
| 2010/0208438 A1 | 8/2010 | Kaltenbacher |
| 2010/0276505 A1 | 11/2010 | Smith |
| 2010/0294268 A1 | 11/2010 | Wensley et al. |
| 2010/0300433 A1 | 12/2010 | Sharma et al. |
| 2011/0233043 A1 | 9/2011 | Cross et al. |
| 2011/0240013 A1 | 10/2011 | Hale et al. |
| 2011/0240014 A1 | 10/2011 | Bennett et al. |
| 2011/0240022 A1 | 10/2011 | Hodges et al. |
| 2011/0244020 A1 | 10/2011 | Hale et al. |
| 2011/0245493 A1 | 10/2011 | Rabinowitz et al. |
| 2011/0253135 A1 | 10/2011 | Hale et al. |
| 2012/0048963 A1 | 3/2012 | Sharma et al. |
| 2013/0032139 A1 | 2/2013 | Hale et al. |
| 2013/0078307 A1 | 3/2013 | Holton |
| 2013/0156823 A1 | 6/2013 | Wu |
| 2013/0180516 A1 | 7/2013 | Damani |
| 2013/0180525 A1 | 7/2013 | Cross et al. |
| 2013/0251813 A1 | 9/2013 | Cawello |
| 2013/0276779 A1 | 10/2013 | Hale |
| 2013/0287851 A1 | 10/2013 | Shaw |
| 2014/0060525 A1 | 3/2014 | Hale et al. |
| 2014/0060532 A1 | 3/2014 | Hodges et al. |
| 2014/0066618 A1 | 3/2014 | Hale et al. |
| 2014/0072605 A1 | 3/2014 | Bennett et al. |
| 2015/0065491 A1 | 3/2015 | Cartt |
| 2015/0157635 A1 | 6/2015 | Hale et al. |
| 2015/0196060 A1 | 7/2015 | Wensley |
| 2015/0250800 A1 | 9/2015 | Hale et al. |
| 2015/0265783 A1 | 9/2015 | Damani et al. |
| 2016/0143364 A1 | 5/2016 | DePiano |
| 2016/0166564 A1 | 6/2016 | Myers et al. |
| 2016/0324845 A1 | 11/2016 | Myers et al. |
| 2016/0374937 A1 | 12/2016 | Hale |
| 2017/0049974 A1 | 2/2017 | Wensley |
| 2017/0105246 A1 | 4/2017 | Cross |
| 2017/0281884 A1 | 10/2017 | Hodges |
| 2018/0021328 A1 | 1/2018 | Myers |

(56) References Cited

U.S. PATENT DOCUMENTS

| | | |
|---|---|---|
| 2018/0126098 A1 | 5/2018 | Sharma |
| 2019/0021987 A1 | 1/2019 | Sharma |
| 2019/0117909 A1 | 4/2019 | Myers |
| 2019/0209546 A1 | 7/2019 | Myers |
| 2020/0246559 A1 | 8/2020 | Wensley |
| 2021/0008300 A1 | 1/2021 | Sharma |
| 2021/0046259 A1 | 2/2021 | Hasegawa |
| 2021/0052830 A1 | 2/2021 | Myers |

FOREIGN PATENT DOCUMENTS

| | | |
|---|---|---|
| CN | 1082365 | 2/1994 |
| CN | 1120109 A | 4/1996 |
| CN | 1176075 | 3/1998 |
| CN | 101437496 A | 5/2009 |
| CN | 107750177 A | 3/2018 |
| CN | 110267662 A | 9/2019 |
| DE | 19854007 | 5/2000 |
| EP | 0039369 | 11/1981 |
| EP | 0274431 | 7/1988 |
| EP | 0 277 519 | 8/1988 |
| EP | 0 358 114 | 3/1990 |
| EP | 0430559 | 6/1991 |
| EP | 0492485 | 7/1992 |
| EP | 0606486 | 7/1994 |
| EP | 0734719 | 2/1996 |
| EP | 0967214 | 12/1999 |
| EP | 1080720 | 3/2001 |
| EP | 1177793 | 2/2002 |
| EP | 1222938 | 7/2002 |
| EP | 0808635 B1 | 7/2003 |
| EP | 1578422 B1 | 6/2007 |
| EP | 3268072 | 1/2018 |
| EP | 3551189 | 10/2019 |
| FR | 921852 A | 5/1947 |
| FR | 2428068 A | 1/1980 |
| GB | 502761 | 1/1938 |
| GB | 903866 | 8/1962 |
| GB | 1366041 | 9/1974 |
| GB | 2108390 | 5/1983 |
| GB | 2122903 | 1/1984 |
| HU | 200105 B | 4/1990 |
| HU | 219392 B | 6/1996 |
| JP | 2574120 | 6/1998 |
| JP | 2004-149447 | 5/2004 |
| JP | 2004-531555 | 10/2004 |
| JP | 2006-511566 | 4/2006 |
| JP | 2006-523486 | 10/2006 |
| JP | 2008-519766 | 6/2008 |
| JP | 2008-519768 | 6/2008 |
| JP | 2008-530134 | 8/2008 |
| JP | 2010-525354 | 7/2010 |
| JP | 2018-510703 | 4/2018 |
| JP | 6773675 | 10/2020 |
| JP | 2021-511893 | 5/2021 |
| KR | 10-2217768 | 2/2021 |
| MX | 2019-006745 | 10/2019 |
| WO | WO 1985/000520 | 2/1985 |
| WO | WO 1988/008304 | 11/1988 |
| WO | WO 1990/002737 | 3/1990 |
| WO | WO 1990/007333 | 7/1990 |
| WO | WO 1991/007947 | 6/1991 |
| WO | WO 1991/018525 | 12/1991 |
| WO | WO 1992/005781 | 4/1992 |
| WO | WO 1992/015353 | 9/1992 |
| WO | WO 1992/019303 | 11/1992 |
| WO | WO 1993/011817 | 6/1993 |
| WO | WO 1993/012823 | 7/1993 |
| WO | WO 94/09842 | 5/1994 |
| WO | WO 1994/016717 | 8/1994 |
| WO | WO 1994/016757 | 8/1994 |
| WO | WO 1994/016759 | 8/1994 |
| WO | WO 1994/017369 | 8/1994 |
| WO | WO 1994/017370 | 8/1994 |
| WO | WO 94/27653 | 12/1994 |
| WO | WO 1994/027576 | 12/1994 |
| WO | WO 1995/031182 | 11/1995 |
| WO | WO 1996/000069 | 1/1996 |
| WO | WO 1996/000070 | 1/1996 |
| WO | WO 1996/000071 | 1/1996 |
| WO | WO 96/09846 | 4/1996 |
| WO | WO 1996/010663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 1996/031198 | 10/1996 |
| WO | WO 1996/037198 | 11/1996 |
| WO | WO 1997/016181 | 5/1997 |
| WO | WO 1997/017948 | 5/1997 |
| WO | WO 1997/023221 | 7/1997 |
| WO | WO 97/27804 | 8/1997 |
| WO | WO 1997/031691 | 9/1997 |
| WO | WO 1997/035562 | 10/1997 |
| WO | WO 1997/035582 | 10/1997 |
| WO | WO 1997/036574 | 10/1997 |
| WO | WO 1997/040819 | 11/1997 |
| WO | WO 1997/049690 | 12/1997 |
| WO | WO 1998/002186 | 1/1998 |
| WO | WO 1998/016205 | 4/1998 |
| WO | WO 98/22170 | 5/1998 |
| WO | WO 1998/029110 | 7/1998 |
| WO | WO 1998/031346 | 7/1998 |
| WO | WO 98/36651 | 8/1998 |
| WO | WO 1998/034595 | 8/1998 |
| WO | WO 1998/037896 | 9/1998 |
| WO | WO 1999/004797 | 2/1999 |
| WO | WO 1999/011311 | 3/1999 |
| WO | WO 1999/016419 | 4/1999 |
| WO | WO 1999/024433 | 5/1999 |
| WO | WO 1999/037347 | 7/1999 |
| WO | WO 1999/037625 | 7/1999 |
| WO | WO 1999/044664 | 9/1999 |
| WO | WO 1999/055362 | 11/1999 |
| WO | WO 1999/059710 | 11/1999 |
| WO | WO 99/64094 | 12/1999 |
| WO | WO 2000/000176 | 1/2000 |
| WO | WO 2000/000215 | 1/2000 |
| WO | WO 2000/000244 | 1/2000 |
| WO | WO 2000/019991 | 4/2000 |
| WO | WO 00/29053 | 5/2000 |
| WO | WO 2000/027359 | 5/2000 |
| WO | WO 2000/027363 | 5/2000 |
| WO | WO 2000/028844 | 5/2000 |
| WO | WO 2000/028979 | 5/2000 |
| WO | WO 2000/029167 | 5/2000 |
| WO | WO 2000/035417 | 6/2000 |
| WO | WO 2000/038618 | 7/2000 |
| WO | WO 2000/044350 | 8/2000 |
| WO | WO 2000/044730 | 8/2000 |
| WO | WO 2000/047203 | 8/2000 |
| WO | WO 2000/051491 | 9/2000 |
| WO | WO 00/66084 | 11/2000 |
| WO | WO 2000/064940 | 11/2000 |
| WO | WO 2000/066106 | 11/2000 |
| WO | WO 2000/066206 | 11/2000 |
| WO | WO 00/76673 | 12/2000 |
| WO | WO 2000/072827 | 12/2000 |
| WO | WO 01/05459 | 1/2001 |
| WO | WO 2001/013957 | 3/2001 |
| WO | WO 2001/017568 | 3/2001 |
| WO | WO 2001/019528 | 3/2001 |
| WO | WO 2001/029011 | 4/2001 |
| WO | WO 2001/032144 | 5/2001 |
| WO | WO 2001/041732 | 6/2001 |
| WO | WO 2001/069136 | 9/2001 |
| WO | WO 2001/080829 | 11/2001 |
| WO | WO 2001/095903 | 12/2001 |
| WO | WO 2002/000198 | 1/2002 |
| WO | WO 2002/024158 | 3/2002 |
| WO | WO 2002/051466 | 7/2002 |
| WO | WO 2002/051469 | 7/2002 |
| WO | WO 2002/056866 | 7/2002 |

(56) References Cited

FOREIGN PATENT DOCUMENTS

| | | |
|---|---|---|
| WO | WO 2002/083119 | 10/2002 |
| WO | WO 02/094236 | 11/2002 |
| WO | WO 02/094242 | 11/2002 |
| WO | WO 2002/094218 | 11/2002 |
| WO | WO 2002/094232 | 11/2002 |
| WO | WO 2002/094234 | 11/2002 |
| WO | WO 2002/098389 | 12/2002 |
| WO | WO 2002/098496 | 12/2002 |
| WO | WO 2002/102297 | 12/2002 |
| WO | WO 2003/024456 | 3/2003 |
| WO | WO 2003/037412 | 5/2003 |
| WO | WO 03/045484 | 6/2003 |
| WO | WO 2003/049535 | 6/2003 |
| WO | WO 2017/189883 | 11/2017 |
| WO | WO 2018/107045 | 6/2018 |

OTHER PUBLICATIONS

U.S. Appl. No. 11/964,630, filed Dec. 26, 2007, Hale.
U.S. Appl. No. 12/111,188, filed Apr. 28, 2008, Hale.
U.S. Appl. No. 12/117,737, filed May 8, 2008, Hale.
U.S. Appl. No. 12/211,247, filed Sep. 16, 2008, Sharma.
U.S. Appl. No. 12/211,554, filed Sep. 16, 2008, Sharma.
U.S. Appl. No. 12/211,628, filed Sep. 16, 2008, Lei.
U.S. Appl. No. 12/245,184, filed Oct. 3, 2008, Hale.
U.S. Appl. No. 12/275,836, filed Nov. 21, 2008, Hale.
U.S. Appl. No. 13/217,385, filed Aug. 25, 2011, Sharma.
U.S. Appl. No. 13/569,006, filed Aug. 7, 2012, Hale.
AK Steel (2007) 304/304L Stainless Steel Data Sheet.
AK Steel (2007) 316/316L Stainless Steel Data Sheet.
Alexza Pharmaceuticals (2015) "AZ-002 (Staccato alprazolam) in epilepsy patients", Dec. 21, 2015, p. 1-6.
Anderson (1982) Drug Metabolism Reviews 13(5):799-826 "Recent Advances in Methodology and Concepts for Characterizing Inhalation Pharmacokinetic Parameters in Animals and Man".
Anonymous, (Jun. 1998) Guidance for Industry: Stability testing of drug substances and products, U.S. Department of Health and Human Services, FDA, CDER, CBER, pp. 1-110.
Benowitz (1994) NIDA Research Monograpy, 2 pages, "Individual Differences in Nicotine Kinetics and Metabolism in Humans".
Bickes and Grubelich (1996) "SCB Ignitioin of Pyrotechnics, thermites, and intermetallics". Explosive Components Department, Sandia National Laboratories. Aug. 20, 1996.
BP: Chemicalsactivities (1999) Product: (Barex) Barrier Resins; Database [Online]; 8 pages; Availabe Web Site: www.bp.com/chemicals/products/product.asp; Last update: Apr. 25, 2016; Accessed on: Aug. 2, 2001.
Brand et al. (Jun. 2000) Journal of Pharmaceutical Sciences 89(6):724-731 "Total Deposition of Therapeutic Particles During Spontaneous and Controlled Inhalations".
Campbell et al. (2001) BMJ 323:1-6 "Are cannabinoids an effective and safe treatment option in the management of pain? A qualitative systemic review".
Carroll et al. (1990) Psychopharmacology (Berl) 102:443-450 "Cocaine-Base Smoking in Rhesus Monkey: Reinforcing and Physiological Effects".
Cichewicz et al. (May 1999) Journal of Pharmacology and Experimental Therapeutics 289(2):859-867, "Enhancement of mu opioid antinociception by oral DELTA 9—tetrahydrocannabinol: Dose response analysis and receptor identification".
Clark and Byron (1986) Z. Erkrank 166:13-24 "Dependence of Pulmonary Absorption Kinetics on Aerosol Particle Size".
Centerwatch.com (2000) Drugs Approved by the FDA—Drug Name: Nicotrol Inhaler; 2 pages; Available Web Site: www.centerwatch.com/patient/drugs/dru202.html; Accessed on: Aug. 2, 2001.
Cleveland Clinic (2010) Article on types and symptoms of epileptic seizure, Dec. 30, 2010.
Communication pursuant to Article 94(3) EPC from European App No. 16762425.3, dated Oct. 23, 2019, 8 pages.
Communication pursuant to Article 94(3) EPC from European App No. 16762425.3, dated Dec. 3, 2020, 6 pages.
Dallas et al. (1983) Developments in the Science and Practice of Toxicology, pp. 419-422, "A Small Animal Model for Direct Respiratory and Hemodynamic Measurements in Toxicokinetic Studies of Volatile Chemicals," Hayes, A. W. et al. eds., Elsevier Science Publishers, New York.
Database Biosis "Online!" Biosciences Information Service, Philadelphia, PA 1979, Knight, V. et al., "Amantadine aerosol in humans", database accession No. PREV 198069035552 abstract, &Antimicrobial Agents and Chemotherapy 16(5):572-578.
Database WPI, Section CH, Week 198941, Derwent Publications Ltd., London, GB; AN 1989-297792 AP002230849 & JP 01 221313 (Nippon Create 1(K), Sep. 4, 1989, abstract.
Examination Report for Canadian App No. 2,979,213, dated Jun. 22, 2018, 7 pages.
Examination Report (First) for New Zealand App No. 735414, dated Mar. 19, 2018, 7 pages.
Examination Report (Further) for New Zealand App No. 735414, dated Nov. 6, 2018, 3 pages.
Extended European Search Report for Application No. 17878604.2, dated Jun. 22, 2020, 10 pages.
Faris et al. (2002) International Journal of Cardiology 82:149-158 "Current evidence supporting the role of diuretics in heart failure: a meta analysis of randomized controlled trials".
Feynman et al. (1964) The Feyman Lectures on Physics: Mainly Electromagnetism and Matter "Chapter 32: Refractive Index of Dense Materials" Addison-Wesley: Publishing Company, Inc., Reading, Massachusetts, pp. 32-1-32-13.
French et al. (2015) Epilepsy and Behavior 46:34-50 "The epilepsy foundation's 4th biennial epilepsy pipeline update conference".
Gleeson et al. (1982) Psychopharmacology 78:141-146 "Chlorpromazine Hyperalgesia Antagonizes Clonidine Analgesia, but Enhances Morphine Analgesia in Rats Tested in a Hot-Water Tail-Flick Paradigm".
Graves et al. (1983) Annals of Internal Medicine 99:360-366 "Patient-Controlled Analgesia".
Hamon et al. (1987) Neuropharmacology 26(6):531-539 "Opioid Receptors and Neuropeptides in the CNS in Rats Treated Chronically with Amoxapine and Amitriptyline".
Hatsukami et al. (May 1990) Pharmacology Biochemistry & Behavior 36:1-7 "A Method for Delivery of Precise Doses of Smoked Cocaine-Base to Human".
Huizer (1987) Pharmaceutisch Weekblad Scientific Edition 9(4):203-211 "Analytical Studies on Illicit Heron. V. Efficacy of Volitization During Heroin Smoking".
Hwang (1999) Wall Street Journal, Jun. 28, 1999, pp. 1-3 "Tobacco: R. J. Reynolds Hopes to Spin Nicotine Into Drugs".
International Search Report and Written Opinion for PCT/US2014/046288 dated Oct. 2, 2014, 9 pages.
International Preliminary Report on Patentability for PCT/US2016/021554, dated Sep. 12, 2017, 7 pages.
International Search Report and Written Opinion for PCT/US2016/021554, dated May 27, 2016.
International Search Report and Written Opinion for PCT/US19/016398, dated Apr. 30, 2019.
International Preliminary Report on Patentability for PCT/US19/016398, dated Aug. 4, 2020.
International Preliminary Report on Patentability for PCT/US2017/065347, dated Jun. 11, 2019.
International Search Report and Written Opinion for PCT/US2017/065347, dated Feb. 22, 2018.
James et al. (1991) Radiation Protection Dosimetry 38(1/3): 159-165 "The Respiratory Tract Deposition Model Proposed by the ICRP Task Group".
Kexun Xu (1989) "Handbook of Organic Chemical Material and Intermediates," Dec. 31, 1989, pp. 490-491 (English relevance is Office Action dated Jan. 30, 2018 with respect to Chinese App. No. 201480050267X w/English Translation).
Kim and Patel (1994) Tet. Letters 35:5603-5606 "'BOP' As a Reagent for Mild and Efficient Preparation of Esters".
Lichtman et al. (1996) Journal of Pharmacology and Experimental Therapeutics 279:69-76 "Inhalation Exposure to Volatilized Opioids Produces Antinociception in Mice".

(56) References Cited

OTHER PUBLICATIONS

Lichtman et al. (2000) European Journal of Pharmacology 399:141-149 "Pharmacological Evaluation of Aerosolized Cannabinoids in Mice".
Lopez (Jul. 26, 1999) "UK Researcher Develops Nicotinic Drugs with R. J. Reynolds", 1 page; Available Web Site: www.eurekalert.org/pub_releases/1999-07/UoKM-Urdn-260799.php; Last Update: Mar. 16, 2002; Accessed on: Oct. 1, 2002.
Lynch (2001) J. Psychiatry Neuroscience 26:30-36 "Antidepressants as analgesics: a review of randomized controlled trials".
Magnusson et al. (2000) Brain Research 855:260-266 "The Involvement of Dopamine in Nociception: the role of D1 and D2 Receptors in the Dorsolateral Striatum".
Mattox and Carroll (1996) Psychopharmacology 125:195-201 "Smoked Heroin Self-Administration in Rhesus Monkeys".
McCormick et al. (1988) British Journal of Anesthesia 80(4):564-565 "Bronchospasm During Inhalation of Nebulized Midazolam".
McGee et al. (1979) American Journal of Hospital Pharmacy 36:633-640 "Phenotiazine Analgesia—Fact or Fantasy?".
Meng et al. (1997) NIDA Research Monogragh 173:201-224 "Inhalation Studies with Drugs of Abuse".
Meng et al. (1999) Drug and Alcohol Dependence 53:111-120 "Pharmacological effects of methamphetamine and other stimulants via inhalation exposure".
NS Healthcare (2014) (hllps://www.ns-healthcare.com/analysis/elegant-simplicity-single-dose-disposable-inhalers-4214657/) Jul. 4, 2014.
Office Action dated Mar. 24, 2017 with respect to Canadian App No. 2,918,145, 4 pages.
Office Action dated Jun. 22, 2018 with respect to Canadian App No. 2,979,213, 7 pages.
Office Action dated Feb. 3, 2020 with respect to Canadian App No. 2,979,213, 5 pages.
Office Action dated Jul. 8, 2020 with respect to Canadian App No. 3,046,385, 6 pages.
Office Action dated Jan. 30, 2018 with respect to Chinese App No. 201480050267.X (w/English Translation).
Office Action dated Nov. 29, 2019 with respect to Chinese App No. 201680027355.7 (wEnglish Translation), 15 pages.
Office Action dated Apr. 15, 2021 with respect to Chinese App No. 201680027355.7 (wEnglish Translation).
Office Action dated Mar. 26, 2018 with respect to Japanese App No. 2016-525796 (w/English Translation).
Office Action dated Oct. 29, 2018 with respect to Japanese App No. 2017-548052 (w/English Translation).
Office Action dated Sep. 20, 2019 with respect to Japanese App No. 2017-548052 (w/English Translation), 6 pages.
Office Action dated Jul. 7, 2020 with respect to Japanese App No. 2019-531043 (w/English Translation) 12 pages.
Office Action dated Feb. 2, 2021 with respect to Japanese App No. 2019-531043 (w/English Translation).
Office Action dated Jan. 26, 2007 with respect to U.S. Appl. No. 10/057,198.
Office Action dated Jul. 3, 2006 with respect to U.S. Appl. No. 10/057,198.
Office Action dated Sep. 20, 2005 with respect to U.S. Appl. No. 10/057,198.
Office Action dated Dec. 4, 2003 with respect to U.S. Appl. No. 10/057,198.
Office Action dated Jun. 5, 2007 with respect to U.S. Appl. No. 10/057,197.
Office Action dated Sep. 21, 2006 with respect to U.S. Appl. No. 10/057,197.
Office Action dated Jan. 12, 2005 with respect to U.S. Appl. No. 10/057,197.
Office Action dated Jun. 3, 2004 with respect to U.S. Appl. No. 10/057,197.
Office Action dated Dec. 15, 2003 with respect to U.S. Appl. No. 10/057,197.
Office Action dated Dec. 28, 2007 with respect to U.S. Appl. No. 10/146,080.
Office Action dated Mar. 20, 2007 with respect to U.S. Appl. No. 10/146,080.
Office Action dated Jun. 5, 2006 with respect to U.S. Appl. No. 10/146,080.
Office Action dated Aug. 25, 2005 with respect to U.S. Appl. No. 10/146,080.
Office Action dated Feb. 27, 2004 with respect to U.S. Appl. No. 10/146,080.
Office Action dated Oct. 30, 2007 with respect to U.S. Appl. No. 10/146,086.
Office Action dated Feb. 12, 2007 with respect to U.S. Appl. No. 10/146,086.
Office Action dated Dec. 13, 2005 with respect to U.S. Appl. No. 10/146,086.
Office Action dated Nov. 21, 2007 with respect to U.S. Appl. No. 10/146,088.
Office Action dated Sep. 28, 2007 with respect to U.S. Appl. No. 10/146,088.
Office Action dated Feb. 16, 2007 with respect to U.S. Appl. No. 10/146,088.
Office Action dated Aug. 13, 2003 with respect to U.S. Appl. No. 10/153,313.
Office Action dated Mar. 8, 2005 with respect to U.S. Appl. No. 10/718,982.
Pfeiffer (1982) Geriatrics 37(2):67-76 "Drugs for pain in the elderly".
Poochikian and Bertha (2000) Resp. Drug Deliv. VII:109-115 "Inhalation Drug Product Excipient Controls: Significance and Pitfalls".
Rapoport and Sheftell (1997) CNS Drugs 7(1):37-46 "Intranasal Medications for the Treatment of Migraine and Cluster Headache".
Schreiber et al. (1999) Pharmacology Biochemistry and Behavior 64(1):75-80 "The Atypical Neuroleptics Clozapine and Olanzapine Differ Regarding Their Antinociceptive Mechanisms and Potency".
ScienceDaily Magazine (Jul. 1999) "University of Kentucky Researcher Develops Nicotinic Drugs with R. J. Reynolds"; 2 pages; Availabe Web Site: www.sciencedaily.com/releases/1999/07/990728073542.htm; Last update: Mar. 14, 2002; Accessed on: Sep. 23, 2002.
Streitwieser and Heathcock, eds., (1981) "Introduction to Organic Chemistry" Second edition, Macmillan Publishing Co., Inc., New York, pp. ix-xvi. (Table of Contents).
Tsantilis et al. (2001) Aerosol Science and Technology 34:237-246 "Sintering Time for Silica Particle Growth".
U.S. Appl. No. 11/687,466, filed Mar. 16, 2007, Zaffaroni et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
U.S. Appl. No. 12/352,582, filed Jan. 12, 2009, Hale et al.
U.S. Appl. No. 12/413,339, filed Mar. 27, 2009, Rabinowitz et al.
U.S. Appl. No. 12/471,070, filed May 22, 2009, Hale et al.
U.S. Appl. No. 12/485,704, filed Jun. 16, 2009, Damani et al.
U.S. Appl. No. 12/490,102, filed Jun. 23, 2009, Hale et al.
Vapotronics, Inc. (1998) "Vapotronics is creating global opportunities in the drug delivery and smoking replacement markets with an innovative digital inhaler technology platform"; Available Web Site: www.vapotronics.com.au/banner.htm; 11 pages; Accessed on: Jun. 5, 2000.
Vaughan (1990) J. Aerosol Sci. 21(3): 453-462 "The Generation of Monodisperse Fibres of Caffeine".
Williams (Feb. 8, 1999) "Rhone-Poulenc Rorer Inc. and Targacept Inc. Announce Alliance to Develop New Drugs to Treat Alzheimer's and Parkinson's Diseases"; 1 page; Available Web Site: www.rpr.rpna.com/ABOUT_RPR/pressrels/1999/990209-targa.html; Last update: Oct. 11, 1999; Accessed on: Jan. 28, 2000.
Wilson, et al. (1979) Proceedings of the Society for Experimental Bioloy and Medicine 161(3):350-354, Biosis Database Accession No. PREV198069008137, "Amatadine Aerosol Particle Aerosol Generation and Delivery to Man".
Wood et al. (1996) Pharmacology Biochemistry & Behavior 53(1):57-66 "Methylecgonidine Coats the Crack Particle".

(56) References Cited

OTHER PUBLICATIONS

Wood et al. (1996) Pharmacology Biochemistry & Behavior 55(2):237-248 "Generation of Stable Test Atmospheres of Cocaine Base and Its Pyrolyzate, Methylecgonidine, and Demonstration of Their Biological Activity".
U.S. Appl. No. 13/311,660, filed Dec. 6, 2011, Bennett et al..
U.S. Appl. No. 13/597,865, filed Aug. 29, 2012, Bennett et al..
U.S. Appl. No. 15/262,954, filed Sep. 12, 2016, Hale et al..
U.S. Appl. No. 15/289,772, filed Oct. 10, 2016, Wensley et al..
Banhart (2000) "Manufacturing Routes for Metallic Foams" JOM, Dec. 2000:22-27.
Banhart (2001) "Manufacture, characterization and application of cellular metals and metal foams" Progress in Materials Science, 46:559-632.
Bennett et al. (1981) "Patient-Controlled Analgesia: A New Concept of Postoperative Pain Relief" Annual Surg., 195(6):700-705.
Darquenne et al. (1997) "Aerosol dispersion in human lung: comparison between numberical simulations and experiments for bolus tests" American Physiological Society, 966-974.
Davis et al. (1972) "Breathing of half-micron aerosols I. Experimental" Journal of Applied Physiology, 32(5):591-600.
Dershwitz et al. (2000) "Pharmacokinetics and pharmacodynamics of Inhaled versus Intravenous Morphine in Healthy Volunteers" Anesthesiology, 93(3):619-628.
Finlay (2001) "The Mechanics of Inhaled Pharmaceutical Aerosols: An Introduction" Academic Press: San Diego, Formula 2.39, 3-14, v-viii.
Gonda (1991) "Particle Deposition in the Human Respiratory Tract" The Lung: Scientific Foundations, Second Edition., Crystal R.G. and West, J.B. (eds), Raven Publishers, New York, 2289-2294.
Heyder et al. (1986) "Deposition of particles in the human respiratory tract in the size Range 0.0005-15 μm" J. Aerosol Sci., 17(5):811-822.
Hurt et al. (1998) "Prying Open the Door to the Tobacco Industry's Secrets About Nicotine" JAMA, 280(13):1173-1181.
Martin et al. (1989) "Pyrolysis and Volatilization of Cocaine" Journal of Analytical Toxicology, 13:158-162.
Pankow et al. (1997) "Conversion of Nicotine in Tobacco Smoke to Its Volatile and Available Free-Base Form through the Action of Faseous Ammonia" Environ. Sci. Technol., 31:2428-2433.
Pankow (2000) "Chemistry of tobacco smoke" ACS Conference—San Francisco, Mar. 26, 2000, 1-8.
Reticulated Vitreous Carbon (1997) Flyer for ERG Materials and Aerospace Corp.
Seeman et al. (1999) "The Form of Nicotine in Tobacco. Thermal Transfer of Nicotine and Nicotine Acid Salts to Nicotine in the Gas Phase" J. Agric. Food Chem., 47:5133-5145.
Sekine et al. (1987) "Abuse of Smoking Methamphetamine Mixed with Tobacoo: 1. Inhalation Efficiency and Pyrolysis Products of Methamphetamine" Journal of Forensic Science 32(5):1271-1280.
Ward et al. (1997) "Pharmacokinetics and Drug Disposition: Morphine pharmacokinetics after pulmonary administration from a novel aerosol delivery system" Clinical Pharamcology & Therapeutics, 62(6):596-609.
International Preliminary Report on Patentability for PCT/US2008/056452, dated Sep. 15, 2009, 10 pages.
International Search Report and the Written Opinion of the International Searching Authority for PCT/US2008/056452, dated Jan. 22, 2009, 17 pages.
EP Search Report/Communication pursuant to Article 94(3) EPC for Application 08754883.0, dated Jun. 4, 2014, 6 pages.
Alexza Pharmaceuticals (2015) "AZ-002 (Staccato alprazolam) in epilepsy patients", Dec. 21, 2015, p. 1-8.

HEATING UNIT FOR USE IN A DRUG DELIVERY DEVICE

CROSS-REFERENCES TO RELATED APPLICATIONS

This application is a continuation of U.S. application Ser. No. 15/289,772, filed Oct. 10, 2016, entitled "Heating Unit for Use in a Drug Delivery Device", which application is a continuation of U.S. application Ser. No. 12/045,674, filed Mar. 10, 2008, entitled "Heating Unit for Use in a Drug Delivery Device" which application claims the priority of earlier filed U.S. Provisional Application Ser. No. 60/894,116, filed Mar. 9, 2007. Each of these applications is incorporated herein by reference in its entirety. Any disclaimer that may have occurred during the prosecution of the above-referenced applications is hereby expressly rescinded, and reconsideration of all relevant art is respectfully requested.

FIELD OF THE INVENTION

The present invention relates generally to drug supply units comprising a substrate having a plurality of holes. More particularly, embodiments of the invention relate to drug supply units intended to be used to vaporize a drug composition deposited on a surface of the substrate, drug delivery devices comprising such drug supply units, and methods of producing an aerosol using such drug delivery devices.

BACKGROUND OF THE INVENTION

Traditionally, inhalation therapy has played a relatively minor role in the administration of therapeutic agents when compared to more traditional drug administration routes of oral delivery and delivery via injection. Due to drawbacks associated with traditional routes of administration, including slow onset, poor patient compliance, inconvenience, and/or discomfort, alternative administration routes have been sought. Pulmonary delivery is one such alternative administration route which can offer several advantages over the more traditional routes. These advantages include rapid onset, the convenience of patient self-administration, the potential for reduced drug side-effects, the ease of delivery by inhalation, the elimination of needles, and the like. Many preclinical and clinical studies with inhaled compounds have demonstrated that efficacy can be achieved both within the lungs and systemically.

However, despite such results, the role of inhalation therapy in the health care field has remained limited mainly to treatment of asthma, in part due to a set of problems unique to the development of inhalable drug formulations and their delivery modalities, especially formulations for, and delivery by, inhalation.

Metered dose inhaler formulations involve a pressurized propellant, which is frequently a danger to the environment, and generally produces aerosol particle sizes undesirably large for systemic delivery by inhalation. Furthermore, the high speed at which the pressurized particles are released from metered dose inhalers makes the deposition of the particles undesirably dependent on the precise timing and rate of patient inhalation. Also, the metered dose inhaler itself tends to be inefficient because a portion of the dose is lost on the wall of the actuator, and due to the high speed of ejection of the aerosol from the nozzle, much of the drug impacts ballistically on the tongue, mouth, and throat, and never gets to the lung.

While solving some of the problems with metered dose inhalers, dry powder formulations are prone to aggregation and low flowability phenomena which considerably diminish the efficiency of dry powder-based inhalation therapies. Such problems are particularly severe for dry powders having an aerosol particle size small enough to be optimal for deep lung delivery, as difficulty of particle dispersion increases as particle size decreases. Thus, excipients are needed to produce powders that can be dispersed. This mix of drug and excipient must be maintained in a dry atmosphere lest moisture cause agglomeration of the drug into larger particles. Additionally, it is well known that many dry powders expand as they are delivered to the patient's airways due to the high levels of moisture present in the lung.

Liquid aerosol formations similarly involve non-drug constituents, i.e. the solvent, as well as preservatives to stabilize the drug in the solvent. Thus, all liquid aerosol devices must overcome the problems associated with formulation of the compound into a stable liquid. Liquid formulations must be prepared and stored under aseptic or sterile conditions since they can harbor microorganisms. This necessitates the use of preservatives or unit dose packaging. Additionally, solvents, detergents and other agents are used to stabilize the drug formulation. Moreover, the dispersion of liquids generally involves complex and cumbersome devices and is effective only for solutions with specific physical properties, e.g. viscosity. Such solutions cannot be produced for many drugs due to the solubility properties of the drug.

Recently, devices and methods for generating aerosols via volatilization of the drug has been developed, which addresses many of these above mentioned problems. (See, e.g., Rabinowitz et al., U.S. Publication No's US 2003/0015190, Cross et al., U.S. Publication No. 2005/0268911; Hale et al., U.S. Pat. No. 7,090,830, each incorporated by reference in its entirety). These devices and methods eliminate the need for excipients to improve flowability and prevent aggregation, solvents or propellants to disperse the compound, solution stabilizers, compound solubility, etc. and hence, the associated problems with these added materials. Additionally, devices and methods have been developed that allow for consistent particle size generation using volatilization. With such devices, drug compound typically is deposited on a surface of a substrate, such as a stainless steel foil. The substrate is rapidly heated to volatilize the drug, followed by cooling of the vapor so that it condenses to form an aerosol (i.e., a condensation aerosol).

Volatilization, however, subjects the drug to potential chemical degradation via thermal, oxidative, and/or other means. The activation energies of these degradation reactions depend on molecular structure, energy transfer mechanisms, transitory configurations of the reacting molecular complexes, and the effects of neighboring molecules. One method to help control degradation during volatilization is the use of the flow of gas across the surface of the compound, to create a situation in which a compound's vapor molecules are swept away from its surface. (See e.g., Wensley et al., U.S. Publication No. US 2003/0062042 A1). Additionally, the use of thin films reduces the amount of thermal degradation by decreasing the temporal duration of close contact between the heated drug molecule and other molecules and/or the surface on which the drug is in contact.

Now, the inventors have discovered, unexpectedly and surprisingly, that a drug supply unit comprising a substrate having a plurality of holes provides a number of advantages. In particular, the inventors have found that the use of such drug supply units allows the formation of a condensation aerosol of higher purity. In addition, the inventors have discovered that the use of such drug supply units allows formation of a condensation aerosol with a higher yield. This discovery forms the basis of the present invention.

SUMMARY OF THE INVENTION

Embodiments of the invention include a drug supply unit comprising a substrate, wherein the substrate has a surface containing a plurality of holes, and wherein at least a portion of the surface is coated with a drug composition.

Other embodiments of the invention include an aerosol drug delivery device comprising: a housing defining an airway; a drug supply unit comprising a surface, wherein at least a portion of the surface includes a plurality of holes; a heating element operatively associated with the drug supply unit, wherein the heating element is configured to heat the substrate; and a drug composition coated onto at least a portion of the surface of the substrate, wherein the heating element is configured to configured to heat the substrate to a temperature sufficient to vaporize at least a portion of the drug. Other embodiments of the invention include a method of producing a drug-containing aerosol, the method comprising: (a) providing an aerosol drug delivery device comprising a housing defining an airway; a drug supply unit comprising a surface, wherein at least a portion of the surface includes a plurality of holes; a heating element operatively associated with the drug supply unit; and a drug composition coated onto at least a portion of the surface of the substrate; wherein the heating element is configured to heat the substrate to a temperature sufficient to vaporize at least a portion of the drug; (b) providing an air flow through the plurality of holes while heating the substrate; and (c) allowing the vaporized drug to cool and condense into an aerosol comprising particles.

These and other objects, aspects, embodiments, features, and advantages of the present invention will be clearly understood through a consideration of the following detailed description. It will be understood that the embodiments described are illustrative of some of the applications of the principles of the present invention. Modifications may be made without departing from the spirit and scope of the invention, including those combinations of features that are individually disclosed and claimed herein.

BRIEF DESCRIPTION OF THE DRAWINGS

FIG. 2A shows a perforated polyimide film substrate having holes measuring $2.8 \times 10^{-3}$ in. by $5.25 \times 10^{-3}$ in.

FIG. 2B shows a perforated polyimide film substrate having holes measuring $8.8 \times 10^{-3}$ in. $\times 9.8 \times 10^{-2}$ in.

FIG. 7 is a bar graph showing aerosol purity (%) and yield (%) at various air flow ratios (across:bottom) for sildenafil free base.

FIG. 8 is a plot showing aerosol purity (%) as a function of drug coating thickness (microns) for sildenafil free base.

DETAILED DESCRIPTION OF THE PREFERRED EMBODIMENTS

Definitions

Figure 1A:
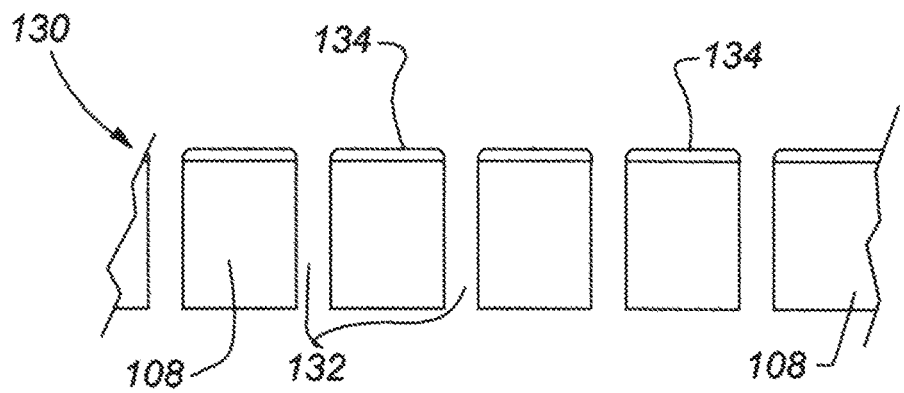
FIG. 1A is a cross-section view of a drug supply unit according to one embodiment of the invention.

As defined herein, the following terms shall have the following meanings when reference is made to them throughout the specification.

"Aerodynamic diameter" of a given particle refers to the diameter of a spherical droplet with a density of 1 g/mL (the density of water) that has the same settling velocity as the given particle.

"Aerosol" refers to a collection of solid or liquid particles suspended in a gas.

"Condensation aerosol" refers to an aerosol that has been formed by the vaporization of a composition and subsequent cooling of the vapor, such that the vapor condenses to form particles.

"Decomposition index" refers to a number derived from an assay described in Example 20. The number is determined by subtracting the purity of the generated aerosol, expressed as a fraction, from 1.

"Drug" means any substance that is used in the prevention, diagnosis, alleviation, treatment or cure of a condition. The drug is preferably in a form suitable for thermal vapor delivery, such as an ester, free acid, or free base form. The drugs are preferably other than recreational drugs. More specifically, the drugs are preferably other than recreational drugs used for non-medicinal recreational purposes, e.g., habitual use to solely alter one's mood, affect, state of consciousness, or to affect a body function unnecessarily, for recreational purposes. The terms "drug", "compound", and "medication" are used herein interchangeably.

"Drug composition" refers to a composition that comprises only pure drug, two or more drugs in combination, or one or more drugs in combination with additional components. Additional components can include, for example, pharmaceutically acceptable excipients, carriers, and surfactants.

"Drug degradation product" and "thermal degradation product" are used interchangeably and mean any byproduct which results from heating the drug(s) and is not responsible for producing a therapeutic effect.

"Drug supply article" and "drug supply unit" are used interchangeably and refer to a substrate with at least a portion of its surface coated with one or more drug compositions. Drug supply articles of the invention may also include additional elements such as, for example, but not limitation, a heating element.

"Fraction drug degradation product" refers to the quantity of drug degradation products present in the aerosol particles divided by the quantity of drug plus drug degradation product present in the aerosol, i.e. (sum of quantities of all drug degradation products present in the aerosol)/((quantity of drug(s) present in the aerosol)+(sum of quantities of all drug degradation products present in the aerosol)). The term "percent drug degradation product" as used herein refers to the fraction drug degradation product multiplied by 100%, whereas "purity" of the aerosol refers to 100% minus the percent drug degradation products.

"Heat stable drug" refers to a drug that has a TSR≥9 when vaporized from a film of some thickness between 0.05 μm and 20 μm. A determination of whether a drug classifies as a heat stable drug can be made as described in Example 20.

"Mass median aerodynamic diameter" or "MMAD" of an aerosol refers to the aerodynamic diameter for which half of the particulate mass of the aerosol is contributed by particles with an aerodynamic diameter larger than the MMAD and half by particles with an aerodynamic diameter smaller than the MMAD.

"Purity" as used herein, with respect to the aerosol purity, means the fraction of drug composition in the aerosol/the fraction of drug composition in the aerosol plus drug degradation products. Thus purity is relative with regard to the purity of the starting material. For example, when the starting drug or drug composition used for substrate coating contained detectable impurities, the reported purity of the aerosol does not include those impurities present in the starting material that were also found in the aerosol, e.g., in certain cases if the starting material contained a 1% impurity and the aerosol was found to contain the identical 1% impurity, the aerosol purity may nevertheless be reported as >99% pure, reflecting the fact that the detectable 1% purity was not produced during the vaporization-condensation aerosol generation process.

"Support" refers to a material on which the composition is adhered, typically as a coating or thin film. The terms "support" and "substrate" are used herein interchangeably. A "perforated substrate" refers to a substrate wherein a surface of the substrate has a plurality of holes that extend through the substrate. As described below, these holes allow a gas (e.g., air) to flow through the substrate. A "non-perforated substrate" refers to a substrate without any holes.

"Substantially free of" means that the material, compound, aerosol, etc., being described is at least 95% free of the other component from which it is said to be substantially free.

"Therapeutically effective amount" means the amount required to achieve a therapeutic effect. The therapeutic effect could be any therapeutic effect ranging from prevention, symptom amelioration, symptom treatment, to disease termination or cure.

"Thermal stability ratio" or "TSR" means the % purity/(100%–% purity) if the % purity is <99.9%, and 1000 if the % purity is ≥99.9%. For example, a respiratory drug vaporizing at 90% purity would have a TSR of 9. An example of how to determine whether a respiratory drug is heat stable is provided in Example 20.

"Thermal vapor" refers to a vapor phase, aerosol, or mixture of aerosol-vapor phases, formed preferably by heating. The thermal vapor may comprise a drug and optionally a carrier, and may be formed by heating the drug and optionally a carrier. The term "vapor phase" refers to a gaseous phase. The term "aerosol phase" refers to solid and/or liquid particles suspended in a gaseous phase.

"Vapor" refers to a gas, and "vapor phase" refers to a gas phase. The term "thermal vapor" refers to a vapor phase, aerosol, or mixture of aerosol-vapor phases, formed preferably by heating.

Drug Supply Unit

The drug supply units described herein may be used to form condensation aerosols. One such method involves the heating of a composition to form a vapor, followed by cooling of the vapor so that it forms an aerosol (i.e., a condensation aerosol).

Typically, the composition is deposited on a substrate, and then the substrate is heated to vaporize the composition. The drug supply unit of the invention comprises a substrate and a drug composition deposited on at least a portion of the substrate, wherein the surface of the substrate has a plurality of holes formed therein that extend through the substrate. As described below, these holes allow a gas (e.g., air) to flow through the substrate.

Typically, the substrate is a heat-conductive substrate. The drug supply unit is particularly suited for use in a device for inhalation therapy for delivery of a therapeutic agent to the lungs of a patient, for local or systemic treatment. The unit is also suited for use in a device that generates an air stream, for application of aerosol particles to a target site. For example, a stream of gas carrying aerosol particles can be applied to treat an acute or chronic skin condition, can be applied during surgery at the incision site, or can be applied to an open wound. As one of skill in the art can readily appreciate, the devices and methods of the invention are applicable not only to a unit consisting of the above components but also to any drug supply unit that consists of these and any other additional number of components up to, and including, the complete drug delivery device itself. Discussed below are aspects of the substrate, the drug composition film, aerosol purity, and surface area features of the substrate for delivery of therapeutic amounts of a drug composition.

A. Substrates

1. Substrate Materials, Surface Characteristics, and Geometry

An illustrative example of one type of drug supply unit of the invention is shown in cross-sectional view in FIG. 1A. Drug supply unit 130 is comprised of a substrate 108 having a plurality of holes 132.

A number of different materials may be used to construct the substrate. Typically, the substrates are heat-conductive and include metals or alloys, such as aluminum, iron, copper, stainless steel, gold, titanium and the like, alloys. The holes in the substrate may be formed by any method known in the art. In one variation, the heat-conductive substrate is a sheet of stainless steel foil that has had holes etched or drilled thorough it. In some embodiments, stainless steel has advantages over materials like aluminum because it has a lower thermal conductivity value, without an appreciable increase in thermal mass. Low thermal conductivity is helpful because heat generated by the process needs to remain in the immediate area of interest.

A drug supply unit of the invention may also comprise treated substrates, which have been described as providing improve purity of the drug composition aerosol generated from films applied thereon. Exemplary substrates of this type are described in Bennett et al., U.S. Publication No. 2005/0034723, which is incorporated herein by reference. Metal substrates disclosed therein have a treated exterior surface. The treated exterior surface is typically an acid treated, heat treated, or metal oxide-enriched surface. The treatment approaches disclosed therein are applicable to a diversity of metals and alloys, including without limitation steel, stainless steel, aluminum, chromium, copper, iron, titanium, and the like, with aluminum, copper, and steel, especially stainless steel, being particularly preferred embodiments. In one variation, the heat-conductive substrate is a sheet of SULFINERT®-treated stainless steel.

Alternatively, the substrate may comprise a ceramic or polymer. In one variation, the heat-conductive substrate is a sheet of polyimide film (KAPTON® polyimide film, DuPont, Wilmington, Del.) comprising a plurality of holes. In such case, the drug supply unit can further comprise a heater element disposed on or within the polymeric substrate. In order to lower the thermal mass, in some preferred embodiments, a thin sheet of polyimide film ($5 \times 10^{-4}$ in. to $1 \times 10^{-3}$ in.) may be used. In some embodiments, electrically conductive heater traces can be formed on a surface of the polyimide film sheet. Although the heater traces typically comprise copper, it is also contemplated herein that the traces can be formed of other conductive materials, such as aluminum, nickel, or gold.

The substrate typically has a thickness of at least $5 \times 10^4$ in. When the substrate comprises a metal (e.g., stainless steel), the substrate typically has a thickness within the range of about $5 \times 10^{-4}$ in. to about $1 \times 10^{-2}$ in. When the substrate comprises a polymer (e.g., polyimide film), the substrate typically has a thickness within the range of about $5 \times 10^{-4}$ in. to about $5 \times 10^{-3}$ in.

At least a portion of the surface of the substrate comprises a plurality of holes through which a flow of gas can pass. Typically, the substrate comprises at least 10, at least 20, at least 30, at least 40, at least 50, at least 60, at least 70, at least 80, at least 90, at least 100, at least 250, at least 500, or more, holes.

Typically, a gas (e.g., air) flows through the holes upon inhalation by a subject using the drug delivery device. The gas may be drawn into the device by the act of inhalation, or may otherwise be provided (e.g., stored within the device under pressure until inhalation).

Typically, the holes have a regular shape, such as a circle, an ellipse, a square, a rectangle, or a regular polygon. In a preferred embodiment, the substrate comprises a plurality of small, circular, regularly spaced holes, typically of the same or similar size. However, the invention is not so limited and the holes could be of irregular shape, and/or have varying sizes and/or spacing. The plurality of holes may have different shapes (e.g., a combination of circular and rectangular holes).

The dimensions of the holes typically remain uniform as they extend through the substrate, but it is within the scope of the invention that the holes can vary in shape and dimension as they extend through the substrate. For example, the holes could have a tapered, conical shape, so that the holes have a larger diameter on one surface of the substrate than on another.

Figure 2A:
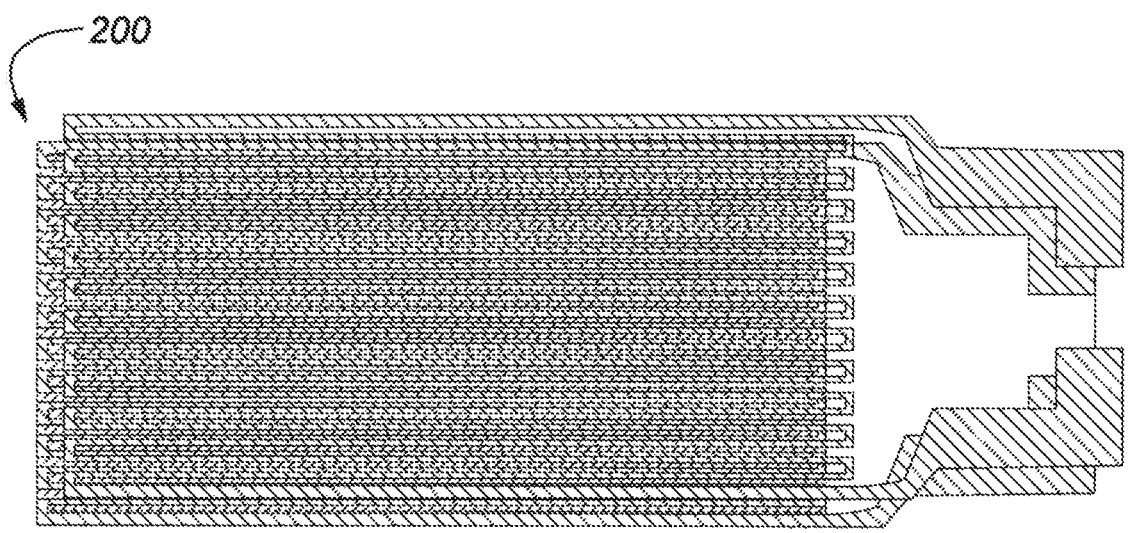
Figure 2B:
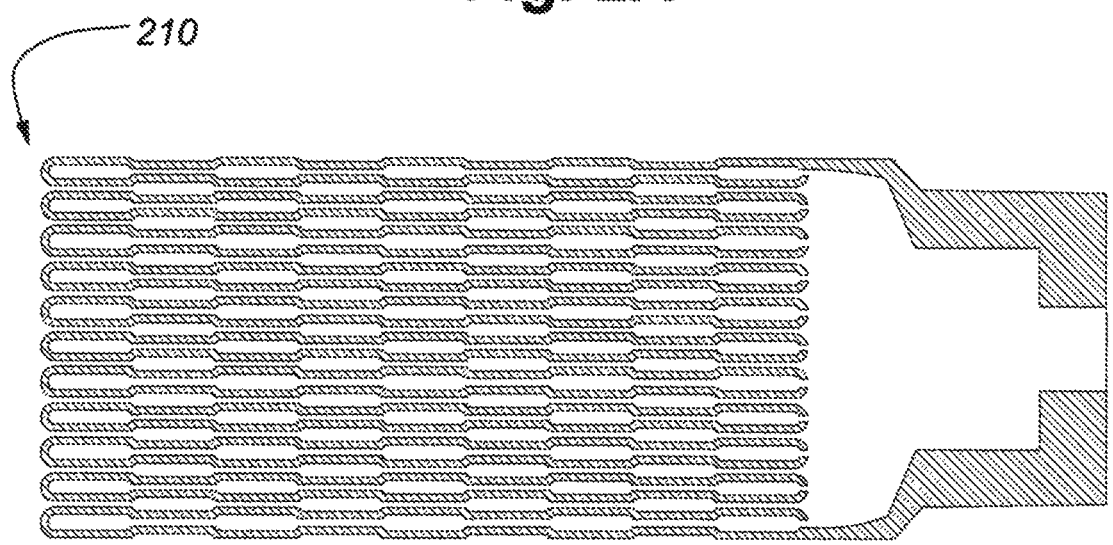

In the case of a drug supply unit comprising a polymeric substrate (e.g., polyimide film) with heater traces, the holes are preferably located between the heater traces, as shown in FIGS. 2A and 2B, which show polyimide film substrates having smaller and larger size holes, respectively. The substrate 200 shown in FIG. 2A has smaller holes measuring $2.8 \times 10^{-3}$ in. by $5.25 \times 10^{-3}$ in. The spacing between holes is $1.5 \times 10^{-2}$ in. The heater 20 shown in FIG. 2B has larger holes measuring 8.8×10⁻³ in. by 9.8×10⁻² in. The polyimide films have a thickness of 1×10⁻³ in.

Figure 3:
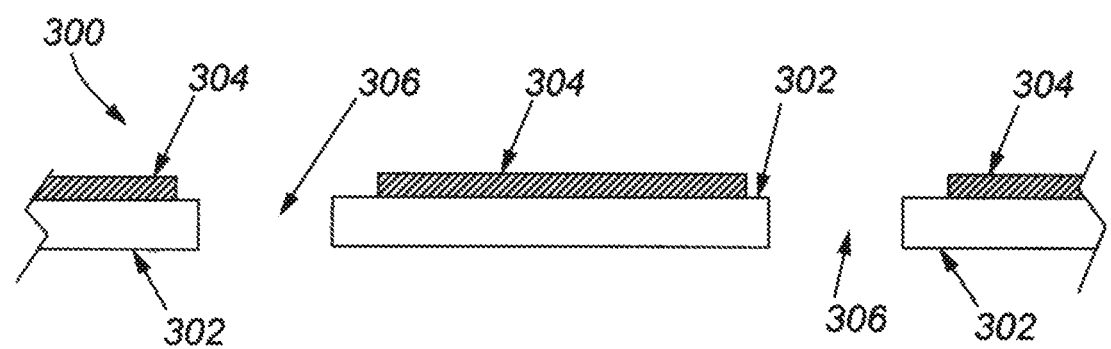
FIG. 3 is a cross-sectional view of a polyimide film substrate, showing the polyimide film substrate, copper heater traces, and holes formed through the polyimide film.

FIG. 3 is a schematic illustration of a polyimide film substrate 300, showing the polyimide film 302, copper heater traces 304, and holes 306 formed through the polyimide film 302.

Typically, the holes are arranged in a regular pattern across the substrate. However, it is also contemplated herein that the holes could be arranged in an irregular pattern or even randomly across the substrate.

The holes may be formed in the substrate using any conventional technique known in the art, including without limitation, laser etching, drilling, wet chemical etching, plasma etching, stamping, punching, and combinations thereof.

A drug is typically coated onto a portion of the substrate. The drug-coated portion of the substrate typically has a surface area within the range of about 8 mm² to about 20 cm²; more typically, within the range of about 9 mm² to about 15 cm². The holes typically occupy between about 1% to about 70%; more typically, between about 10% to about 60%; and, most typically, between about 20% to about 50%, of the drug-coated surface area.

The drug is typically coated to a coating density ranging from about 0.1 mg/cm² to about 10 mg/cm² on the substrate surface. This roughly corresponds to a coating thickness within the range of about 1 μm to about 100 μm.

The drug may be coated onto the substrate surface using any conventional coating technique known in the art, including without limitation, spray coating, dip coating, and inkjet printing.

In a preferred embodiment of a polyimide film heating unit, the drug is coated onto the polyimide film side of the heating unit. It is also contemplated herein that the drug may be coated onto the side of the heating unit having the conductive heater traces, or onto both sides of the heating unit.

Drug supply units for use in the present invention are typically electrical drug supply units, where current is passed through an electrical resistance element. For example, heating of the substrate may be accomplished by passing current through a thin metallic substrate, or through electrically conductive traces formed on the surface of a polymeric substrate (as described above). However, it is also within the scope of the present invention that other types of heating methods known in the art may be used. For example, heating of the substrate may be accomplished using optical, radiative, convection, or chemical energy sources.

As contemplated herein, the substrate for use in the heating unit of the invention can either be an exterior surface of a heating unit itself, or can be a separate material operatively associated with the heating unit (e.g., in direct contact with or in proximity to the exterior surface of the heating unit). The minimum temperature required for volatilization of the drug and, thus, the maximum allowable spacing between the substrate and the heating unit will, of course, vary with the particular drug, among other factors.

The perforated substrate can be of virtually any geometry, but is most typically square or rectangular in shape. The perforated substrate of the drug supply unit illustrated in FIG. 1A is shown as having a substantially planar geometry, having an upper surface 134 (upon which drug composition 138 has been deposited) and lower surface 136. "Across" air flow is directed over the surface on which the drug composition has been deposited (e.g., parallel to and in the same plane as upper surface 134) while "bottom" air flow is directed through holes 132, from lower surface 136 to upper surface 134.

Figure 1B:
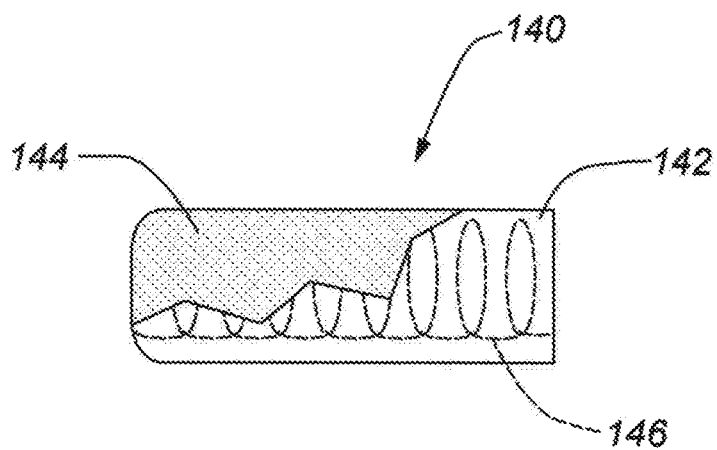
FIG. 1B is a cut-away view of a drug supply unit according to one embodiment of the invention.

FIG. 1B is a perspective, cut-away view of an alternative geometry of the aerosol delivery article. Article 140 is comprised of a hollow, cylindrically-shaped substrate 142 formed from a heat-conductive material. Substrate 142 has a perforated exterior surface 144. Drug composition (not shown) is deposited on the exterior surface 144. As will be described in more detail below, in use, the substrate of the aerosol delivery article is heated to vaporize all or a portion of the drug film. During vaporization, "across" air flow is directed over exterior surface 144 of the substrate and "bottom" air flow is directed through the holes in substrate 142, from the hollow interior of substrate 142 to the exterior surface 144.

2. Heating of the Substrate

Typically, heat is applied to the substrate to vaporize the drug composition film. It will be appreciated that the temperature to which the substrate is heated will vary according to the drug's vaporization properties and the selected minimum purities and yields of the aerosol, but the substrate is typically heated to a temperature of at least about 150° C., preferably of at least about 250° C., more preferably at least about 300° C. or 350° C. Heating the substrate produces a thermal vapor that in the presence of the flowing gas (both across and through the substrate) generates aerosol particles. Thus, the drug supply unit can further comprise a heating element for supplying heat to the substrate to produce a substrate temperature greater than 150° C. and to volatilize all or a portion of the drug composition film from the substrate. Preferably, the temperature is sufficient to substantially volatilize the drug composition film from the substrate in a period of 2 seconds or less, more preferably in less than 1 second, still more preferably in less than 500 milliseconds, and most preferably in less than 200 milliseconds.

In FIG. 1B, the substrate surface is partially cut-away in the figure to expose a heating element 146 disposed in interior of substrate 142. As shown, the substrate can be hollow with a heating element inserted into the hollow space. The heating element in the embodiment shown takes the form of an electrical resistive wire that produces heat when a current flows through the wire. Other heating elements are suitable, including but not limited to a solid chemical fuel, chemical components that undergo an exothermic reaction, inductive heat, etc. Heating of the substrate by conductive heating is also suitable.

As one of skill in the art will recognize, depending on the choice of substrate material, the optimal means of heating may vary. For example, if the substrate material is stainless steel, a preferred means of heating typically is electrical resistive heating. On the other hand, if the substrate material is aluminum, a preferential means to vaporize the drug composition on the substrate surface typically is by conductive means, i.e., by bringing the aluminum in contact with a heat source (e.g., a halogen bulb), rather than electrical resistance means, due to the higher thermal conductivity and higher electrical conductivity of aluminum relative to stainless steel.

In studies conducted in support of the invention, a variety of drugs were deposited on stainless steel and polyimide film (KAPTON®) substrates. However, as disclosed above, and as one of skill in the art will recognize, a variety of different substrates can be used.

Drug Composition Film

In addition to the substrate, the aerosol delivery article comprises a drug composition deposited on the substrate, typically as a film or coating. As shown in FIG. 1A, de D. Surface Area of the Substrate Another feature of the aerosol delivery article is that the substrate surface area is typically such that a therapeutic dose of the drug aerosol is delivered in a single use of the device when used by a subject such that dose titration by the patient to deliver a minimum effective dose is possible. For a drug delivery device of the invention, the yield from a single dose may be determined by collecting the thermal vapor evolved upon actuation of the device or assembly and analyzing its composition as described herein, and comparing the results of analysis of the thermal vapor to those of a series of reference standards containing known amounts of the drug. The amount of drug or drugs required in the starting composition for delivery as a thermal vapor depends on the amount of drug or drugs entering the thermal vapor phase when heated (i.e., the dose produced by the starting drug or drugs), the bioavailability of the thermal vapor phase drug or drugs, the volume of patient inhalation, and the potency of the thermal vapor drug or drugs as a function of plasma drug concentration.

Typically, the bioavailability of thermal vapors ranges from 20-100% and is preferably in the range of 50-100% relative to the bioavailability of drugs infused intravenously. The potency of the thermal vapor drug or drugs per unit plasma drug concentration is preferably equal to or greater than that of the drug or drugs delivered by other routes of administration. It may substantially exceed that of oral, intramuscular, or other routes of administration in cases where the clinical effect is related to the rate of rise in plasma drug concentration more strongly than the absolute plasma drug concentration. Thus, for medications currently given orally, the effective human therapeutic dose of that drug in thermal vapor form is generally less than the standard oral dose. Preferably it will be less than 80%, more preferably less than 40%, and most preferably less than 20% of the standard oral dose. For medications currently given intravenously, the drug dose in a thermal vapor will generally be similar to or less than the standard intravenous dose. Preferably it will be less than 200%, more preferably less than 100%, and most preferably less than 50% of the standard intravenous dose.

Determination of the appropriate dose of thermal vapor to be used to treat a particular condition can be performed via animal experiments and a dose-finding (Phase I/II) clinical trial. Preferred animal experiments involve measuring plasma drug concentrations after exposure of the test animal to the drug thermal vapor. These experiments may also be used to evaluate possible pulmonary toxicity of the thermal vapor. Because accurate extrapolation of these results to humans is facilitated if the test animal has a respiratory system similar to humans, mammals such as dogs or primates are a preferred group of test animals. Conducting such experiments in mammals also allows for monitoring of behavioral or physiological responses in mammals. Initial dose levels for testing in humans will generally be less than or equal to the least of the following: current standard intravenous dose, current standard oral dose, dose at which a physiological or behavioral response was obtained in the mammal experiments, and dose in the mammal model which resulted in plasma drug levels associated with a therapeutic effect of drug in humans. Dose escalation may then be performed in humans, until either an optimal therapeutic response is obtained or dose-limiting toxicity is encountered.

The actual effective amount of drug for a particular patient can vary according to the specific drug or combination thereof being utilized, the particular composition formulated, the mode of administration and the age, weight, and condition of the patient and severity of the episode being treated. The amount of drug that is required to provide a therapeutic dose is generally known in the art or can be determined as discussed above.

The amount of drug that is required to provide a therapeutic dose is generally known in the art or can be determined as discussed above. The required dosage, discussed above, and the determined film thickness of the instant methods (as set by the selected minimum aerosol purities and yield) dictate the minimum required substrate area in accordance with the following relationship:

$$\text{film thickness (cm)} \times \text{drug density (g/cm}^3\text{)} \times \text{substrate area (cm}^2\text{)} = \text{dose (g)}$$

As noted above, drug density can be determined experimentally or from the literature, or if unknown, can be assumed to be 1 g/cc. To form a drug supply article comprising a drug film on a heat-conductive substrate that is capable of administering an effective human therapeutic dose, the minimum substrate surface area is determined using the relationships described above to determine a substrate area for a determined film thickness (according to the methods of the instant invention) that will yield a therapeutic dose of drug aerosol.

The actual dose of drug delivered, i.e., the percent yield or percent emitted, from the drug-supply article will depend on, along with other factors, the percent of drug film that is vaporized upon heating the substrate. Thus, for drug films that yield upon heating 100% of the drug film and aerosol particles that have 100% drug purity, the relationship between dose, thickness, and area given above correlates directly to the dose provided to the user. As the percent yield and/or particle purity decrease, adjustments in the substrate area can be made as needed to provide the desired dose. Also, as one of skill in the art will recognize, larger substrate areas other than the minimum calculated area for a particular film thickness can be used to deliver a therapeutically effective dose of the drug. Moreover, as can be appreciated by one of skill in art, the film need not coat the complete surface area if a selected surface area exceeds the minimum required for delivering a therapeutic dose from a selected film thickness.

Formation of Condensation Aerosols

Also disclosed herein is a method of producing a drug-containing condensation aerosol comprising providing a substrate having the drug deposited on its surface, wherein the surface of the substrate has a plurality of holes formed therein. The substrate is heated to a temperature sufficient to vaporize the drug while simultaneously providing an air flow across the substrate and through the substrate via the plurality of holes. The drug is preferably heated to a temperature and for a duration that results in an acceptably low level of decomposition. The vaporized drug is preferably rapidly mixed into the air flow to cool and preclude additional decomposition of the drug. The vaporized drug is then allowed to condense into an aerosol comprising particles. The terms "air", "air flow", and "gas" are used interchangeably herein, and are intended to encompass ambient air as well as any other appropriate (i.e., physiologically acceptable, non-explosive) gases, including compressed gases. For example, the device of the invention could be attached to a separate tank of compressed gas that blows air or another suitable gas up through the perforations in the substrate concurrently with heating of the substrate.

The aerosolized drug preferably has a purity level of at least 90%; more preferably, at least 95%; more preferably, at least 96%; more preferably, at least 97%. As used herein, the term "pure" refers to an aerosolized drug that contains no thermal degradation products, excipients, or other contaminants. For example, an aerosolized drug that is at least 97% pure contains less than 3% of thermal degradation products, excipients, or other contaminants. As used herein, the term "thermal degradation product" means any byproduct which results from heating the drug.

The aerosol is preferably characterized by less than 10% by weight of a thermal degradation product, more preferably, less than 5%, more preferably, less than 1%, more preferably, less than 0.5%, more preferably, less than 0.1%, or, more preferably, less than 0.03% by weight of a thermal degradation product.

In certain embodiments, for example, when the drug delivery device is designed for portable use with a battery power source, efficient energy use can be desirable. Minimization of the energy used to release the drug from the substrate can, at least in part, depend on the shape and dimensions of the substrate, the materials forming the substrate, and the placement of the substrate within the airway. In certain embodiments, the substrate can comprise an electrically resistive material such as a foil. In certain embodiments, the substrate can be a stainless steel foil and can include a layer of one or more materials such as a gold layer to facilitate, for example, forming an electrical connection, and/or modifying the electrical properties such as the resistance of a portion of the foil. The appropriate dimensions for a substrate can depend at least in part, on the desired resistance, the amount of drug disposed on the substrate, the amount of energy needed to vaporize the drug disposed on the substrate, and/or on mechanical stability considerations.

Delivery Devices

As shown in FIG. 1A, there is a drug supply unit 130 having a heat-conductive substrate 108 comprising a plurality of holes 132 extending therethrough. A composition coating 134 is at least a portion of the upper surface 134.

FIG. 1B provides a perspective, cut-away view of another embodiment of drug supply unit 140. The drug supply unit comprises a cylindrical substrate 142. This substrate may be formed from a heat-conductive material, for example. The substrate 142 includes a plurality of holes 144 extending therethrough. A thin layer of a drug (not shown) for aerosolization is coated onto external surface 142. As shown in the cut-away portion, there is a heating element 146 disposed in the substrate 142. The substrate 142 can be hollow with a heating element inserted into the hollow space, or solid with a heating element incorporated into the substrate. "Bottom" gas flow into the hollow space passes through the substrate via the plurality of holes while "across" gas flow passes over the external surface of substrate 142.

The illustrative heating element 146 shown in FIG. 1B is shown as an electrical resistive wire that produces heat when a current flows through it, but as noted above, a number of different heating methods and corresponding devices are acceptable. For example, acceptable heat sources can supply heat to the drug supply unit at rates that rapidly achieve a temperature sufficient to completely vaporize the composition from the support surface. For example, heat sources that achieve a temperature of 200° C. to 500° C. or more within a period of 2 seconds or less are typical, although it should be appreciated that the temperature chosen will be dependent upon the vaporization properties of the composition, but typically the vaporization temperature will be at least about 200° C.; preferably, at least about 250° C.; more preferably, at least about 300° C. or 350° C. Heating the substrate 142 produces a drug composition vapor that in the presence of a flowing gas generates aerosol particles in the desired size range. The presence of the gas flow is generally prior to, simultaneous with, or subsequent to heating the substrate. In one embodiment, the substrate is heated for a period of less than about 1 second, and more preferably for less than about 500 milliseconds, still more preferably for less than about 200 milliseconds. The drug aerosol particles are inhaled by a subject for delivery to the lung.

Figure 1C:
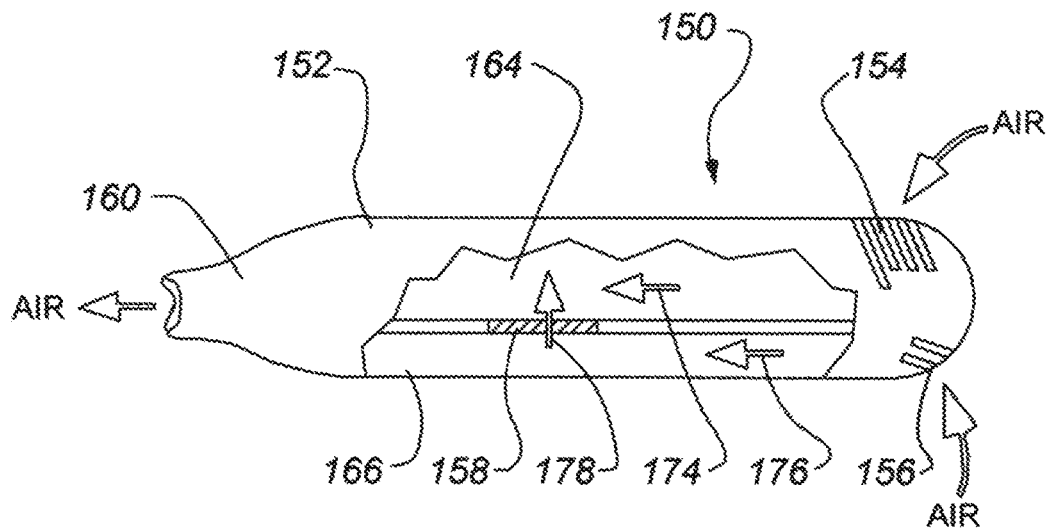
FIG. 1C is a cut-away view of a drug delivery device according to one embodiment of the invention.

FIG. 1C is a perspective view of an embodiment drug delivery device 150 that incorporates an embodiment of the drug supply unit of the invention. Housing 152 comprises a first air inlet 154 and a second air inlet 156, which lead, respectively, to first airway 164 and second airway 166. Substrate 158 is disposed between first airway 164 and second airway 166. Substrate 158 includes a plurality of holes (not shown) fluidly connecting first airway 164 and second airway 166. A drug for aerosolization (not shown) is disposed on a portion of the surface of substrate 158 in communication with first airway 164. When a user places the device 150 in his/her mouth and inhales a breath through tapered mouthpiece 160, air flows through inlets 156 and 158, establishing a first airflow 174 in first airway 164, and a second airflow 176 in second airway 166, such that second airflow 176 passes from second airway 166 to first airway 164 through the holes in substrate 158. The combined first air flow 174 and second airflow 176 carry the aerosol to the subject through mouthpiece/outlet 160.

The devices described herein may additionally contain a variety of components to facilitate aerosol delivery. For instance, the device may include any component known in the art to control the timing of drug aerosolization relative to inhalation (e.g., breath-actuation). Similarly, the device may include a component to provide feedback to patients on the rate and/or volume of inhalation, or a component to prevent excessive use (i.e., "lockout" feature). In addition, the device may further include a component to prevent use by unauthorized individuals, and a component to record dosing histories. These components may be used alone, or in combination with other components.

The element that allows cooling may be of any configuration. For example, it may be an inert passageway linking the heating means to the inhalation means. Similarly, the element permitting inhalation by a user may be of any configuration. For example, it may be an exit portal that forms a connection between the cooling element and the user's respiratory system.

The device as shown has aperatures that control the gas flow ratio. In an alternative embodiment, the across air flow or bottom air flow may be regulated by a gas-flow control valve(s) disposed upstream of the solid support. The gas-flow valve(s) may, for example, include an inlet port communicating with the chamber, and a deformable flap adapted to divert or restrict airflow away from the port increasingly, with increasing pressure drop across the valve. Similarly, the gas-flow valve may include an actuation switch. In this variation, the valve movement would be in response to an air pressure differential across the valve, which for example, could function to close the switch. The gas-flow valve may also include an orifice designed to limit the rate of airflow into the chamber.

The device may also include a bypass valve communicating with the chamber downstream of the unit for offsetting the decrease in airflow produced by the gas-flow control valve, as the user draws air into the chamber. In this way, the bypass valve could cooperate with the gas-control valve to control the flow through the condensation region of the chamber as well as the total amount of air being drawn through the device. Thus the total volumetric airflow through the device in this variation would be the sum of the volumetric airflow rate through the gas-control valve and the volumetric airflow rate through the bypass valve.

Aerosol Composition

The compositions described herein typically comprise at least one drug compound. The drug compositions may comprise other compounds as well. For example, the composition may comprise a mixture of drug compounds, a mixture of a drug compound and a pharmaceutically acceptable excipient, or a mixture of a drug compound with other compounds having useful or desirable properties. The composition may comprise a pure drug compound as well. In preferred embodiments, the composition consists essentially of pure drug and contains no propellants or solvents.

Any suitable drug compound may be used. Drugs that can be used include, for example but not limitation, those listed in U.S. Pat. No. 7,090,830.

Typically, the drugs of use in the invention have a molecular weight in the range of about 150-700, preferably in the range of about 200-700, more preferably in the range of 250-600, still more preferably in the range of about 250-500. In some variations, the drugs have a molecular weight in the range 350-600 and in others the drugs have a molecular weight in the range of about 300-450. In other variations, where the drug is a heat stable drug, the drug can have a molecular weight of 350 or greater.

Typically, the compound is in its ester, free acid, or free-base form. However, it is also a possibility that the compound will be vaporizable from its salt form. Indeed, a variety of pharmaceutically acceptable salts are suitable for aerosolization. Illustrative salts include, without limitation, the following: hydrochloric acid, hydrobromic acid, acetic acid, maleic acid, formic acid, and fumaric acid salts. Salt forms can be purchased commercially, or can be obtained from their corresponding free acid or free base forms using methods well-known in the art.

Suitable pharmaceutically acceptable excipients may be volatile or nonvolatile. Volatile excipients, when heated, are concurrently volatilized, aerosolized and inhaled with the drug. Classes of such excipients are known in the art and include, without limitation, gaseous, supercritical fluid, liquid and solid solvents. The following is a list of exemplary carriers within these classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Additionally, pharmaceutically acceptable carriers, surfactants, enhancers, and inorganic compounds may be included in the composition. Examples of such materials are known in the art.

In some variations, the aerosols are substantially free of organic solvents and propellants. Additionally, water is typically not added as a solvent for the drug, although water from the atmosphere may be incorporated in the aerosol during formation, in particular, while passing air over the film and during the cooling process. In other variations, the aerosols are completely devoid of organic solvents and propellants. In yet other variations, the aerosols are completely devoid of organic solvents, propellants, and any excipients. These aerosols comprise only pure drug, less than 10% drug degradation products, and a carrier gas, which is typically air.

Typically, the drug has a decomposition index less than 0.15. Preferably, the drug has a decomposition index less than 0.10. More preferably, the drug has a decomposition index less than 0.05. Most preferably, the drug has a decomposition index less than 0.025

In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations, the condensation aerosol particles comprise less than 10% by weight of a thermal degradation product. In other variations, the condensation drug aerosol particles comprise less than 5%, 1%, 0.5%, 0.1%, or 0.03% by weight of a thermal degradation product.

In certain embodiments of the invention, the drug aerosol has a purity of between 90% and 99.8%, or between 93% and 99.7%, or between 95% and 99.5%, or between 96.5% and 99.2%.

Typically, the aerosol has a number concentration greater than $10^6$ particles/mL. In other variations, the aerosol has a number concentration greater than $10^7$ particles/mL. In yet other variations, the aerosol has a number concentration greater than $10^8$ particles/mL, greater than $10^9$ particles/mL, greater than $10^{10}$ particles/mL, or greater than $10^{11}$ particles/mL.

The gas in which the aerosol particles are suspended is typically air. It is contemplated, however, that other gases, in particular inert gases, such as argon, nitrogen, helium, and the like, also may be used. The gas can also include vapor of the composition that has not yet condensed to form particles. Typically, the gas does not include propellants or vaporized organic solvents. In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations the condensation drug aerosol has an MMAD in the range of about 1-3 µm. In some variations the geometric standard deviation around the MMAD of the condensation drug aerosol particles is less than 3.0. In other variations, the geometric standard deviation around the MMAD of the condensation drug aerosol particles is less than 2.5, or less than 2.0.

Substrate Screening Apparatus and Testing Procedures

Figure 4A:
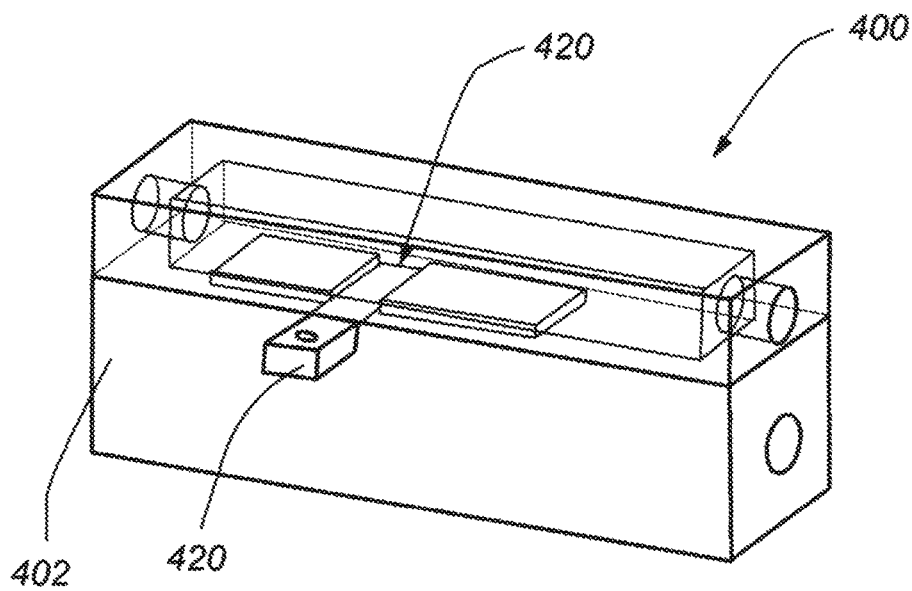
FIG. 4A is a schematic of an embodiment of a substrate screening apparatus.
Figure 4B:
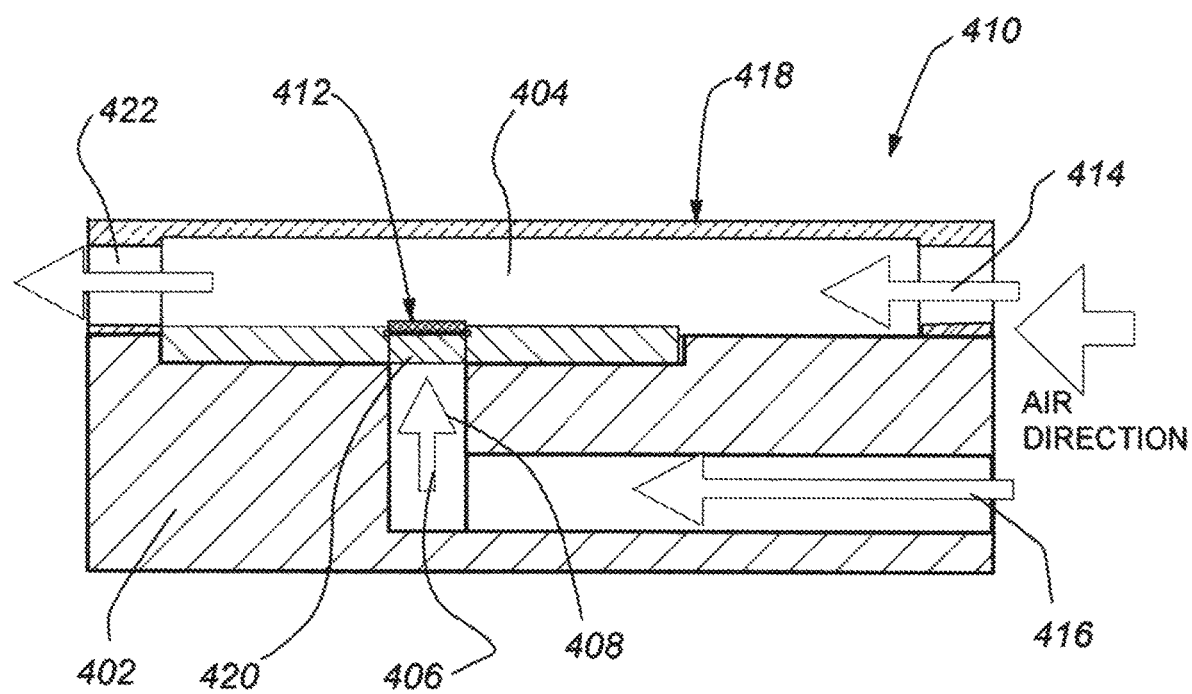
FIG. 4B is a cross-sectional view of the substrate screening apparatus embodiment shown in FIG. 4A.

FIG. 4A is a schematic of an embodiment of the substrate screening apparatus 400. FIG. 4B is a cross-sectional view of the substrate screening apparatus 400.

The substrate screening apparatus 400 is made of a machined plastic (polyoxymethylene, DELRIN® Acetal Resin, DuPont, Wilmington, Del.) block 402 with a 2 cm² cross-sectional area for mounting a substrate 412. Block 402 includes a first airway 404 extending from first inlet 414 to outlet 422. Block 402 also include a second airway 406 extending from second inlet 416 to substrate 412, where it typically joins the first airway. The substrate 412 is mounted in the substrate screening apparatus 400 across two electrodes 420. A first air flow 414 is established in first airway 404 and a second air flow 416 is established in second airway 406 such that the second air flow 416 passes from the second airway 406 to first airway 404 through holes in the substrate 412. While providing air flows 414 and 416, the substrate 412 is heated, typically by discharging a capacitor (not shown) across the substrate 412. In a one embodiment, the flow of air passing through holes in the substrate 412 is in a direction orthogonal to that of air flow 414. Substrate 412 is coated with a drug composition film. The substrate 412 is heated to vaporized all or a portion of the drug composition. The vaporized drug subsequently cools and condenses to form a condensation aerosol that is carried to the outlet by air flow 414, joined by air flow 416). Accordingly, the condensation aerosol is emitted from the outlet 422.

Figure 6:
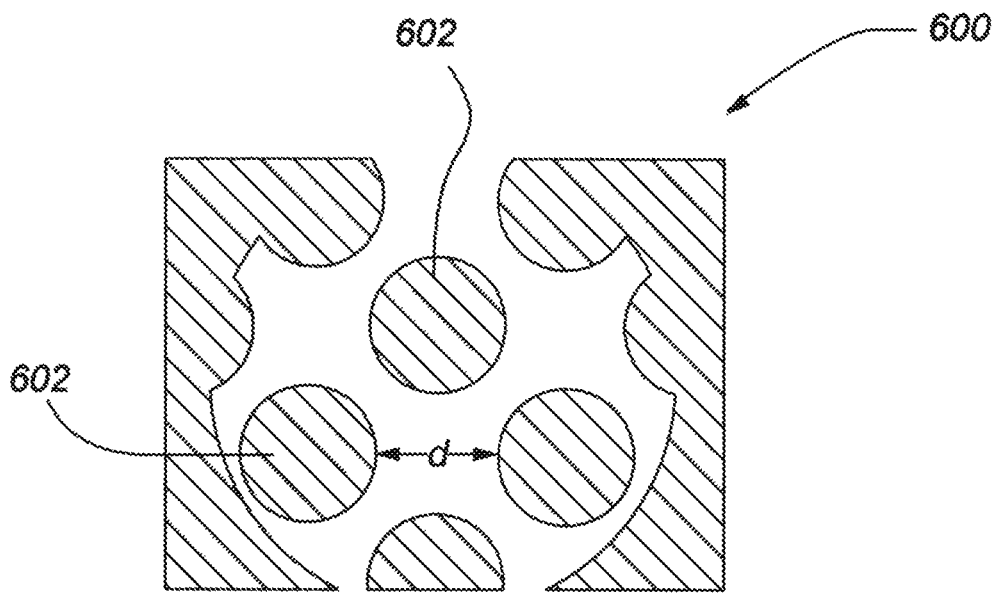
FIG. 6 shows a magnified image of a perforated stainless steel substrate.

Test substrates having dimensions 0.50 in. wide by 2-3 in. long cut from sheets of 304 stainless steel and 316 stainless steel. FIG. 6 shows a magnification of a representative test substrate 600, having regularly spaced, circular holes formed in the stainless steel sheet. The distance between the edge of one hole to the edge of an adjacent hole is indicated as "d" on FIG. 6. The distance "d" is also referred to herein as "hole spacing" or "spacing between holes." As used herein, the term "% porosity" of the substrate refers to the percentage of the nominal total surface area of the substrate (i.e., the surface area if there were no holes) that is occupied by the holes. Thus, a rectangular substrate measuring 0.5 in.×3 in. would have a nominal total surface area of 1.5 in$^2$. If the substrate had 400 circular holes having a diameter of 0.01 square inch, it would have a porosity of approximately 2.1%.

The test substrates were meticulously cleaned to remove any contamination from previous processing by ultrasonication in a 60° C., 6.5% Ridoline bath for 5 minutes followed by ultrasonication in a reverse-osmosis deionized (RODI) water bath at 40° C. for 1 minute followed by a 3-cycle dump rinse using RODI. To prevent water spots, the test substrates were dipped in an isopropanol bath and transferred to a 40° C. drying oven for solvent removal. Some test substrates were also subjected to heat oxidation step, performed by laying the stainless steel substrates on a sheet of aluminum foil and placing them in an oven at 350° C. for 6 hours. These "heat passivated" substrates were then re-cleaned as described above.

The test substrates were then coated with a drug composition. The drug was typically dissolved in a volatile organic solvent (e.g., dichloromethane/methanol mixture or acetone or other suitable organic solvent) and then spray-coated onto the test substrates using an automated spray coater. Coating parameters, such as the drug concentration in the coating solution, solution flow rate, were selected to obtain a uniform drug coating of the desired coating density (i.e., mass/area).

After coating, a sampling of coated substrates was extracted to determine if the mass of coated drug is within tolerance. The mass of drug coated per test article was determined by high performance liquid chromatography (HPLC) analysis and used to calculate a nominal coating thickness metric using the following formula:

$$\lambda = \frac{mass}{\rho * SA},$$

where λ is the thickness of the drug coating, SA is the surface area of the drug coating, and ρ is the density of the drug. The density was generally assumed to be 1.0 g/cm$^3$ unless a different literature value was known. Therefore, 1 mg deposited over an area of 5 cm$^2$ results in a nominal coating thickness of 2 µm. The coating thickness is most easily varied by either altering the drug concentration in the coating solution and/or the flow rate.

Total air flow through the substrate screening apparatus was set by providing air flows 414 and 416 at a desired ratio. (As used herein, "across" air flow refers to air flow 414 and "bottom" air flow refers to air flow 416.) Brass electrodes 420 attached to the substrate screening apparatus 400 were used to clamp the substrate 412 in place and provide electrical connections. For most experiments, a 1-Farad capacitor was used as the energy source. The capacitor was typically charged to 11-14 volts, depending on the desired substrate temperature. A high current relay was used to connect the circuit and discharge the capacitor across the substrate to induce heating and vaporization of the drug.

Figure 5:
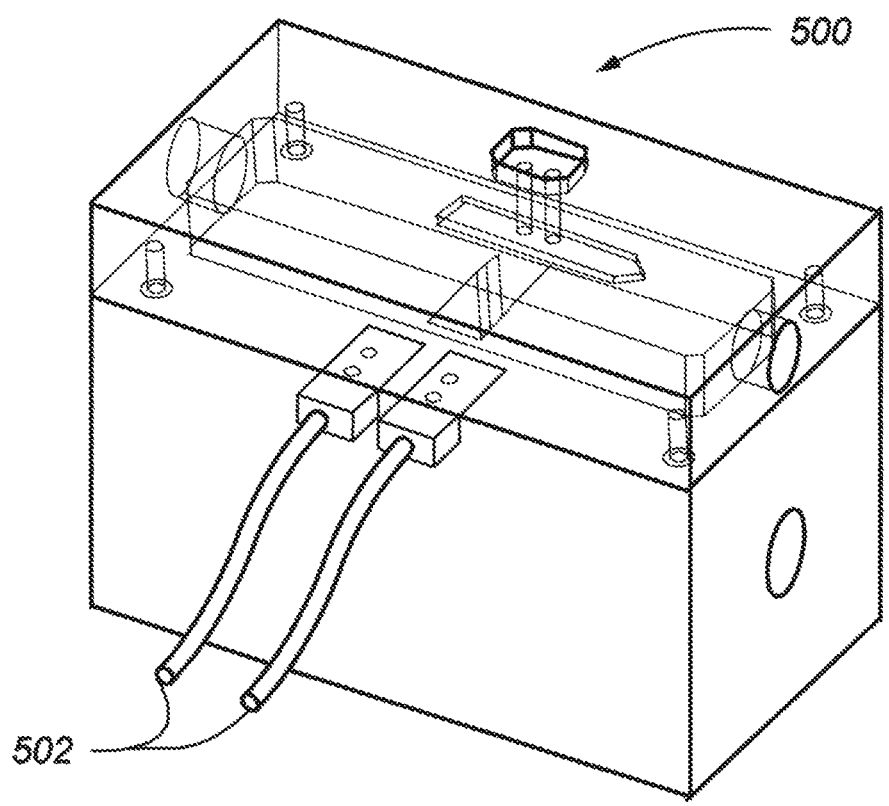
FIG. 5 is a schematic of another embodiment of a substrate screening apparatus.

FIG. 5 is a schematic of another embodiment of a substrate screening apparatus 500 that was used to direct air flow through the holes of coated polyimide film (KAPTON® polyimide film) substrates (see FIGS. 2A and 2B). Substrate screening apparatus 500 is similar in configuration and operation to substrate screening apparatus 400, with the exception that substrate screening apparatus 500 includes two electrodes 502 on the same side of the screening apparatus 500, whereas substrate screening apparatus 400 includes two electrodes 420 on opposite sides of the screening apparatus 400. In the examples using polyimide film substrates described below, a polyimide film substrate coated with a drug composition was placed in substrate screening apparatus 500 across electrodes 502. A computer-controlled power supply was connected to the electrodes. The power supply was typically capable of heating the polyimide film substrate to the target temperature within 300 milliseconds, and the substrate was kept at the target temperature for a duration of 1 second.

To determine aerosol purity and emitted dose, a 2 µm Teflon filter (ZEFLUOR PTFE filters, available from Zefon International, Inc., Ocala, Fla.) was placed immediately downstream from the screening apparatus during aerosol generation. After the aerosol was collected from the air stream, the filter was removed, extracted with a known volume of HPLC-grade methanol, and analyzed for both drug content and purity. The "used" test substrate was also extracted for residual drug, and the airway of the screening apparatus was swabbed for determination of the amount of aerosol deposition within the apparatus.

The filter extracts were analyzed by HPLC using a C-18 reverse phase column (4.6 mm ID×150 mm length, 5 µm packing, Capcell Pak UG120, available from Shiseido Fine Chemicals, Tokyo, Japan) eluted with (1) water/0.1% trifluoroacetic acid and (2) acetonitrile/0.1% trifluoroacetic acid at a flow rate of 1 mL/minute with a linear gradient over 24 minutes and a total run time of 36 minutes. Detection was from 200-400 nm using a photodiode array detector. Purity was calculated by measuring peak areas from the chromatogram obtained at 225 nm. Confirmatory purity evaluations were additionally performed by inspection of the full 200-400 nm wavelength range. In addition, a portion of the filter extracts is analyzed by HPLC with mass spectrometric detection. Analyses by these alternate methods yielded similar purity results when compared to the primary HPLC analysis.

An Anderson Cascade Impactor (ACI), an inertial impaction size separating device, was used to determine the particle size distribution of the aerosol. The ACI consists of several stages, with each successive stage having a smaller size cutoff. By extracting and determining the mass of drug deposited at each stage, it is possible to estimate the particle size distribution of the aerosol. The ACI was placed immediately downstream from the screening apparatus. Again, the airway and substrate were extracted to determine the mass balance for each actuation of the device.

EXAMPLES

Example 1

Loperamide and flunisolide condensation aerosols were produced by the substrate screening apparatus using 304 stainless steel perforated substrates having the % porosities, hole spacings, and hole diameters shown in Table 1. The substrates were spray-coated with loperamide free base or flunisolide free base at coating densities of 0.3 mg/cm$^2$ and 0.4 mg/cm$^2$, respectively. Air flow ratios (across:bottom) of 23:5 and 18:10 were evaluated. The substrate was rapidly heated to approximately 400° C. for loperamide and approximately 375° C. for flunisolide.

TABLE 1

Characteristics of Perforated 304 Stainless Steel Substrates

| Substrate # | Hole Diameter | Hole Spacing | % Porosity |
|---|---|---|---|
| 1 | 0.005" | 0.015" | 5 |
| 2 | 0.005" | 0.009" | 10 |
| 3 | 0.005" | 0.005" | 20 |
| 4 | 0.010" | 0.03" | 5 |
| 5 | 0.010" | 0.018" | 10 |
| 6 | 0.010" | 0.010" | 20 |
| 7 | 0.010" | 0.004" | 40 |
| 8 | 0.020" | 0.059" | 5 |
| 9 | 0.020" | 0.036" | 10 |
| 10 | 0.020" | 0.020" | 20 |
| 11 | 0.020" | 0.008" | 40 |
| 12 | 0.040" | 0.118" | 5 |
| 13 | 0.040" | 0.016" | 40 |

Aerosol purity results for loperamide aerosolized from perforated 304 stainless steel substrates at an across:bottom air flow ratio of 23:5 are presented in Table 2.

TABLE 2

Aerosolization of Loperamide from Perforated Stainless Steel Substrates

| | Aerosol Purity (% ± SD) Hole Diameter | | | |
|---|---|---|---|---|
| % Porosity | 0.005" | 0.010" | 0.020" | 0.040" |
| 5 | 94.6 ± 0 | 95.4 ± 1.1 | 95.3 ± 0.2 | 91.5 ± 0.1 |
| 10 | 96.3 ± 0.1 | 94.4 ± 0.3 | 94.9 ± 0.2 | — |
| 20 | 96.8 ± 0.4 | 96.3 ± 0.2 | 89.6 ± 0.8 | — |
| 40 | — | 96.1 ± 0.2 | 95.2 ± 0.6 | 94.1 ± 0.2 |

Aerosol purity results for loperamide aerosolized from perforated 304 stainless steel substrates at an across:bottom air flow ratio of 18:10 are presented in Table 3.

TABLE 3

Aerosolization of Loperamide from Perforated Stainless Steel Substrates

| | Aerosol Purity (% ± SD) Hole Diameter | | | |
|---|---|---|---|---|
| % Porosity | 0.005" | 0.010" | 0.020" | 0.040" |
| 5 | 93.9 ± 0 | 95.9 ± 0 | 95.2 ± 0.3 | 90.5 ± 0.4 |
| 10 | 96.9 ± 0.4 | 94 ± 0.2 | 94.8 ± 0.2 | — |
| 20 | 97.4 ± 0.1 | 96.4 ± 0.1 | 89.8 ± 0.6 | — |
| 40 | — | 96.8 ± 0.2 | 95 ± 0.5 | 94.5 ± 0.3 |

Aerosol purity results for flunisolide aerosolized from perforated 304 stainless steel substrates at an across:bottom air flow ratio of 23:5 are presented in Table 4.

TABLE 4

Aerosolization of Flunisolide from Perforated Stainless Steel Substrates

| | Aerosol Purity (% ± SD) Hole Diameter | | | |
|---|---|---|---|---|
| % Porosity | 0.005" | 0.010" | 0.020" | 0.040" |
| 5 | 73.6 ± 2.3 | 76.1 ± 0.1 | 77.9 ± 1.1 | 68.6 ± 1.1 |
| 10 | 82.7 ± 1.4 | 71.4 ± 0.7 | 72.7 ± 1.8 | — |
| 20 | 87.9 ± 2 | 80.6 ± 3.1 | 69.9 ± 0.3 | — |
| 40 | — | 84.2 ± 0.1 | 80 ± 1.3 | 74.3 ± 7.3 |

Aerosol purity results for flunisolide aerosolized from perforated 304 stainless steel substrates at an across:bottom air flow ratio of 18:10 are presented in Table 5.

TABLE 5

Aerosolization of Flunisolide from Perforated Stainless Steel Substrates

| | Aerosol Purity (% ± SD) Hole Diameter | | | |
|---|---|---|---|---|
| % Porosity | 0.005" | 0.010" | 0.020" | 0.040" |
| 5 | 80.1 ± 1.8 | 83.6 ± 1.4 | 77.8 ± 2 | 70.4 ± 1.1 |
| 10 | 81.4 ± 0.9 | 75.4 ± 1.2 | 77.2 ± 2.8 | — |
| 20 | 90.7 ± 0.7 | 80.8 ± 1.4 | 74.7 ± 1 | — |
| 40 | — | 85.6 ± 0.8 | 81.9 ± 1.2 | 77 ± 1 |

Both compounds exhibited similar trends in aerosol purity with increasing hole diameter and porosity. Both compounds exhibited the greatest aerosol purity at a hole diameter of 0.005" and 20% porosity (Substrate #3 in Table 1). Loperamide was less sensitive to changes in air flow than flunisolide.

Example 2

Sildenafil aerosols were produced by the substrate screening apparatus using 0.005" thick 316 stainless steel substrates having a regular staggered pattern of circular, 0.006" diameter holes. The holes, which were formed in the substrate by chemical etching, occupied approximately 27% of the total surface area of the substrate. The distance "d" between the holes was 3.5×10$^{-3}$ in.

The substrates were spray-coated with a 15 mg/mL solution of sildenafil free base (isolated from pills, available from Pfizer, Inc., New York, N.Y.) dissolved in dichloromethane/methanol (2:1 volume:volume) at coating densities of 0.18, 0.50, and 1.07 mg/cm$^2$ (approximate coating thicknesses: 1.8, 5.0, and 10.7 μm). Total (across+bottom)

air flow rate was 28.3 liters/minute. Various airflow ratios and vaporization temperatures were evaluated.

Figures 7, 8:
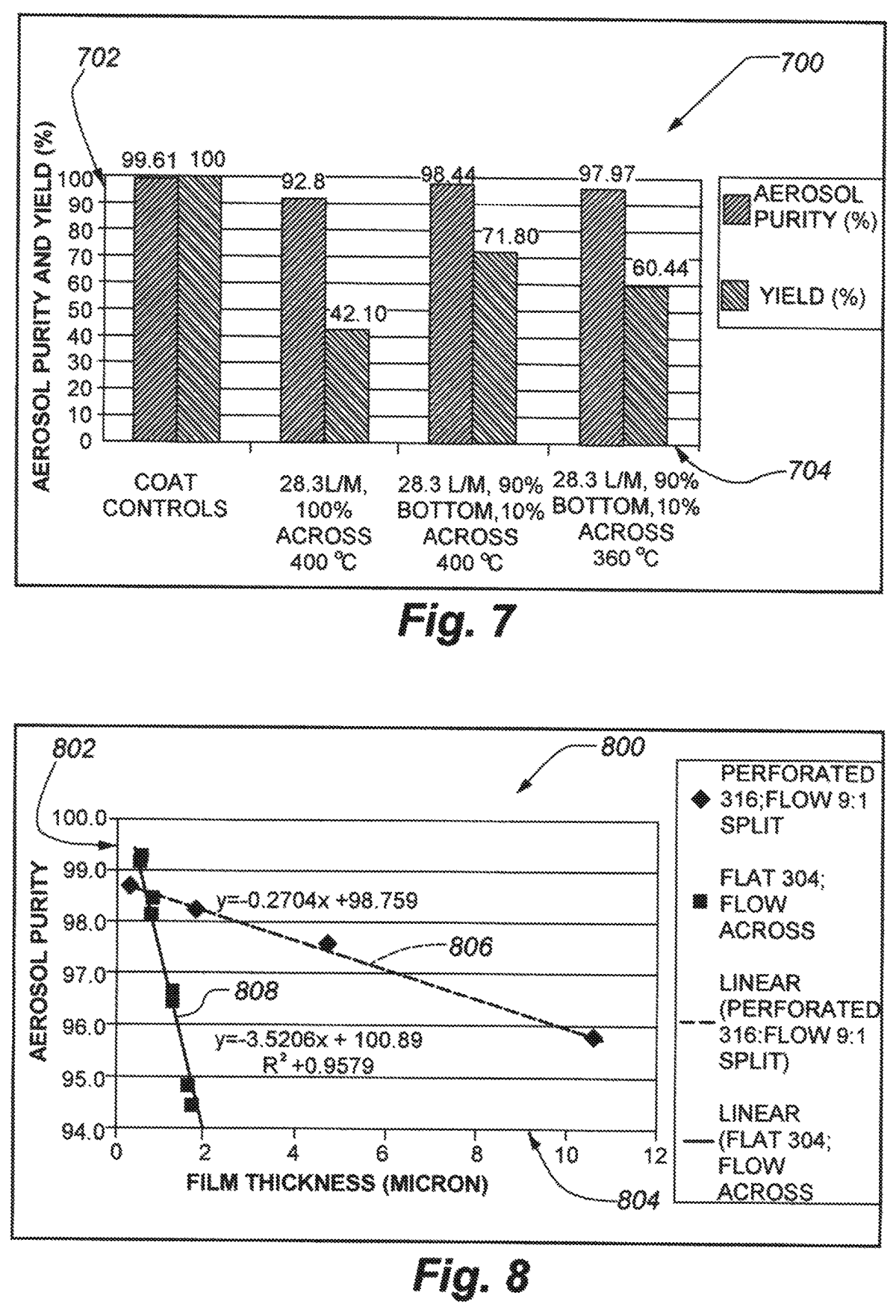

FIG. 7 is a bar graph 700 showing aerosol purity (%) and yield (%) 702 for a sildenafil coating density of 0.18 mg/cm$^2$ at various air flow ratio conditions 704 at 400° C. and 360° C. (last set of data). Of the tested air flow ratios, the highest aerosol purity and yield were obtained when 90% of the air flow was directed from under the bottom (uncoated side) of the substrate (refer to FIG. 2B), and 10% from across the substrate.

Sildenafil aerosols were produced by the substrate screening apparatus using the perforated 316 stainless steel substrates described above and a solid (i.e., non-perforated) 304 stainless steel substrate. The substrates were spray-coated with a 15 mg/mL solution of sildenafil free base (isolated from pills, available from Pfizer, Inc., New York, N.Y.) dissolved in dichloromethane/methanol (2:1 volume:volume) at various drug coating densities. Total (across+bottom) air flow rate was 28.3 liters/minute. Various airflow ratios were evaluated.

FIG. 8 is a plot 800 showing aerosol purity (%) 802 of sildenafil free base as a function of drug coating thickness 804. Curve 806 represents aerosol purity for the perforated substrates; curve 808 represents aerosol purity for the solid substrates. As shown in plot 800, when the perforated substrates were tested with a 1:9 across:bottom air flow ratio, aerosol purity levels of 97% or more were obtained with drug coating thicknesses up to 6 μm. For the solid substrates with 100% of the air flow directed across the substrate, aerosol purity dropped off rapidly as the drug coating thickness increased. Drug coating thicknesses greater than about 1 μm resulted in aerosol purity levels below 97%. When the drug coating thickness was increased to 2 μm, aerosol purity levels decreased to 94% and below.

Example 3

Bumetanide condensation aerosols were produced by the substrate screening apparatus using the perforated 316 stainless steel substrates described above. The substrates were spray-coated with a 50 mg/mL solution of bumetanide free base (available from Solmag S.p.A., Garbagnate, Italy) dissolved in methanol/acetone (50:50 volume:volume) at a coating density of 0.07 mg/cm$^2$ (approximate coating thickness: 0.7 am). Total air flow rate was 20 liters/minute.

As discussed above, in certain cases, oxidizing the stainless steel substrates prior to drug vaporization yields increased aerosol purity. Therefore, the perforated stainless steel substrates were heat-oxidized and re-cleaned according to the procedure described above prior to coating with drug.

Figure 9:
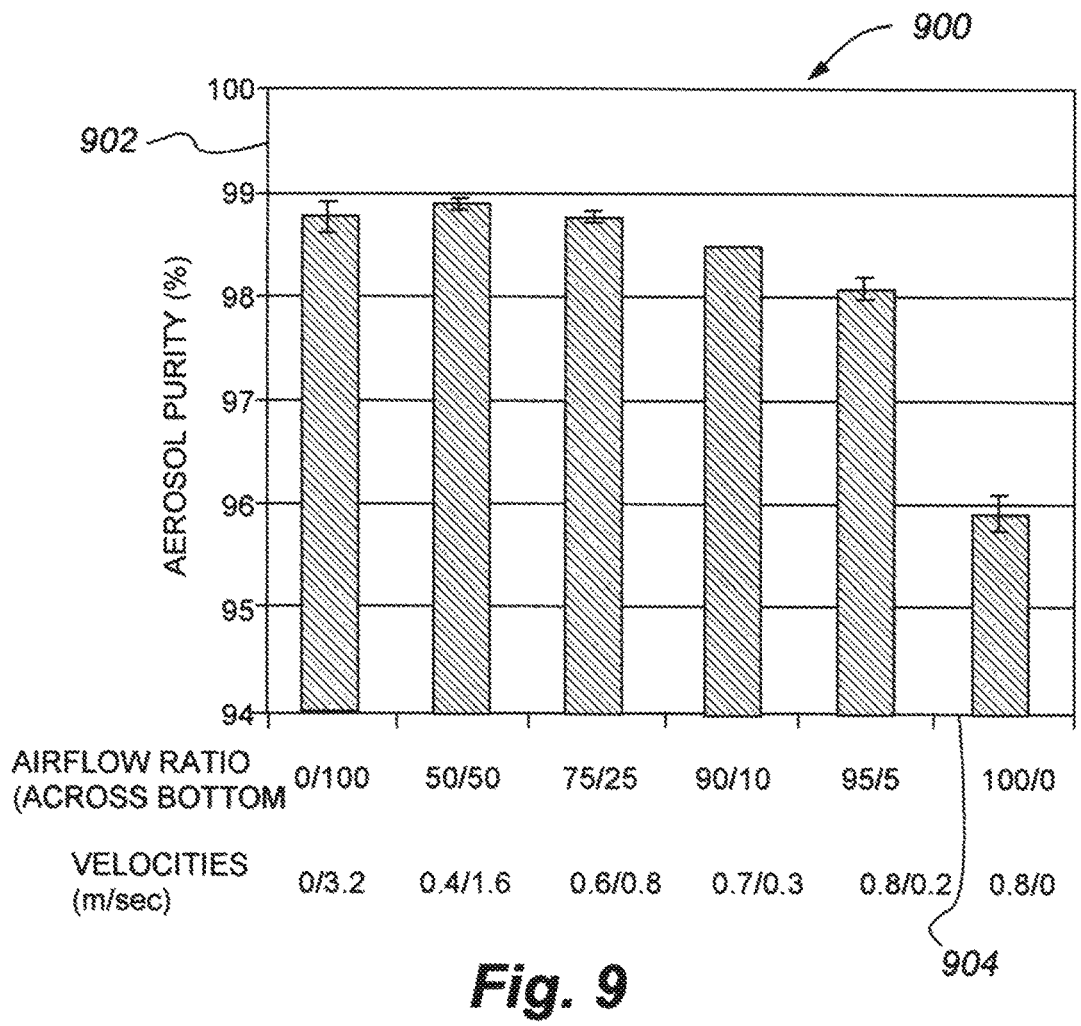
FIG. 9 is a bar graph showing aerosol purity (%) at various air flow ratios (across:bottom) for bumetanide free base.

FIG. 9 is a bar graph 900 showing aerosol purity (%) 902 of bumetanide free base at various air flow ratios 904. As shown in graph 900, as the percentage of air flow coming across (as opposed to from under the bottom, uncoated side) the substrate increased, aerosol purity level decreased. However, aerosol purity level remained at 98% when as little as 5% of the air flow was coming through the substrate.

Table 6 presents aerosol purity data as a function of air flow ratio and drug coating density for aerosolization of bumetanide free base from a heat-oxidized, perforated 316 stainless steel substrate (n=3 for each condition tested). Total air flow rate was 20 liters/minute.

TABLE 6

Aerosolization of Bumetanide from Perforated Stainless Steel Substrates

| Air Flow (Across:Bottom) | Drug Coating Density (mg/cm$^2$) | | |
|---|---|---|---|
| | 0.08 | 0.26 | 0.58 |
| 100:0 | 95.8 ± 0.6 | 94.8 ± 0.2 | 90.7 ± 0.4 |
| 90:10 | 99.2 ± 0.1 | 98.6 ± 0.1 | 98.4 ± 0.3 |
| 0:100 | 99.3 ± 0.1 | 98.9 ± 0.1 | 98.7 ± 0.3 |

The data shown in Table 6 indicate that a high aerosol purity was maintained as the drug coating thickness was increased, when air flowed through the bottom of the substrate (90:10 and 0:100 air flow ratio). Even a seven-fold increase in drug coating density (from 0.08 to 0.58 mg/cm$^2$) resulted in no significant decrease in aerosol purity. The addition of even a small amount of air flow through the substrate was found to provide a significant increase in the amount of drug that can be coated onto the perforated substrate surface.

The aerosol purity of bumetanide aerosolized from heat-oxidized, perforated 316 stainless steel substrates was measured as a function of both drug coating density and air flow ratio. Drug coating densities of 0.07, 0.10, and 0.14 mg/cm$^2$ were tested, at across:bottom air flow ratios of 0:100, 50:50, and 100:0. Total air flow rate was 20 liters/minute.

Table 7 presents aerosol purity data as a function of air flow ratio and drug coating density for aerosolization of bumetanide from a heat-oxidized, perforated 316 stainless steel substrate (n=3 for each condition tested). Total air flow rate was 20 liters/minute.

TABLE 7

Aerosolization of Bumetamde from Perforated Stainless Steel Substrates

| | Drug Coating Density (mg/cm$^2$) | | | |
|---|---|---|---|---|
| | 0.10 | | 0.14 | |
| Air Flow (Across:Bottom) | Mean Aerosol Purity (%) | Relative Standard Deviation (%) | Mean Aerosol Purity (%) | Relative Standard Deviation (%) |
| 100:0 | 95.7 | 0.38 | 94.8 | 0.14 |
| 50:50 | 98.8 | 0.08 | 98.9 | 0.02 |
| 0:100 | 98.8 | 0.06 | 98.8 | 0.08 |

Table 8 presents emitted aerosol purity and emitted drug dose data as a function of air flow ratio for aerosolization of bumetanide from a heat-oxidized, perforated 316 stainless steel substrate (n=3 for each condition tested). Total air flow rate was 20 liters/minute.

TABLE 8

Aerosolization of Bumetanide from Perforated Stainless Steel Substrates

| Air Flow (Across:Bottom) | Emitted Aerosol Purity (%) | SD (%) | Emitted Drug Dose (%) | SD (%) |
|---|---|---|---|---|
| 100:0 | 96.4 | 0.2 | 75 | 7 |
| 50:50 | 98.4 | 0.2 | 89 | 7 |
| 0:100 | 98.5 | 0.1 | 82 | 14 |

The emitted drug dose was calculated using the following equation:

$$\text{Emitted Drug Dose} = \frac{\text{Aerosolized Drug}(\%)}{\text{Coated Drug}(\%)}$$

Figure 10:
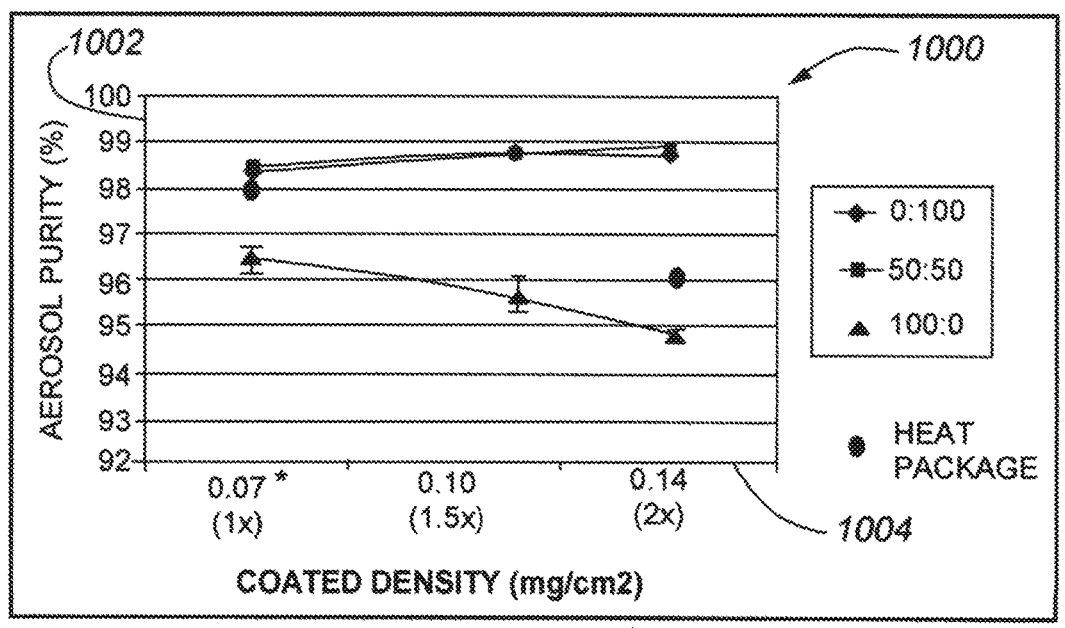
FIG. 10 is a plot showing aerosol purity (%) as a function of drug coating density ($mg/cm^2$) for bumetanide free base.

The data presented in Tables 7 and 8 are represented graphically in FIG. 10, which is a plot 1000 showing aerosol purity (%) 1002 of bumetanide free base as a function of drug coating density 1004. The data shown in Tables 7 and 8 and FIG. 10 corroborate the results shown in FIG. 9, where greater aerosol purities were observed as a greater proportion of the air flow was directed through the substrate. These data substantiate the conclusion that the addition of air flow from beneath the substrate allows for a larger amount of drug to be coated onto the perforated substrate surface, without a loss in aerosol purity.

The effects of varying the air flow ratio on aerosolized particle size were also examined. Table 9 shows mass median aerodynamic diameter (MMAD), geometric standard deviation (GSD), and % drug recovery for aerosolization of bumetanide from heat-oxidized, perforated 316 stainless steel substrates, at various air flow ratios (n=3 for each condition tested). Drug coating density was approximately 0.07 mg/cm$^2$. Total air flow rate was 28.3 liters/minute.

TABLE 9

Aerosolization of Bumetanide from Perforated Stainless Steel Substrates

| Air flow (Across:Bottom) | MMAD (μm) | GSD | % Drug Recovery |
|---|---|---|---|
| 100:0 | 3.6 ± 0.5 | 4.0 ± 0.5 | 63 ± 13 |
| 90:10 | 2.7 ± 0.1 | 2.0 ± 0.1 | 78 ± 10 |
| 0:100 | 0.4 ± 0.0 | 2.4 ± 0.1 | 69 ± 8 |

As shown in Table 9, the particle size (MMAD) tended to decrease as the proportion of the air flow coming through the substrate (as opposed to across the substrate) was increased, allowing the aerosolized drug particle size to be tuned to a desired range by simply varying the across:bottom air flow ratio. The very small drug particle size obtained at the 0:100 across:bottom air flow ratio may indicate that there was substantially more dilution of the vaporized drug compound into the airstream than with the conventional (100% across) air flow arrangement.

The effects of varying both the drug coating density and air flow ratio on aerosolized particle size were also examined. Table 10 shows mass median aerodynamic diameter (MMAD) and standard deviation (SD) for aerosolization of bumetanide from heat-oxidized, perforated 316 stainless steel substrates, at various drug coating densities and air flow ratios (n=3 for each condition tested). Total air flow rate was 28.3 liters/minute.

TABLE 10

Aerosolization of Bumetanide from Perforated Stainless Steel Substrates

| Drug Coating Density (mg/cm$^2$) | Air flow (Across:bottom) | Average MMAD (μm) | SD (μm) |
|---|---|---|---|
| 0.08 | 90:10 | 2.2 | 0.4 |
| 0.26 | 90:10 | 1.6 | 0.2 |
| 0.58 | 100:0 | 1.7 | 0.2 |
|  | 90:10 | 1.9 | 0.1 |
|  | 0:100 | 0.9 | 0.1 |

Figure 11:
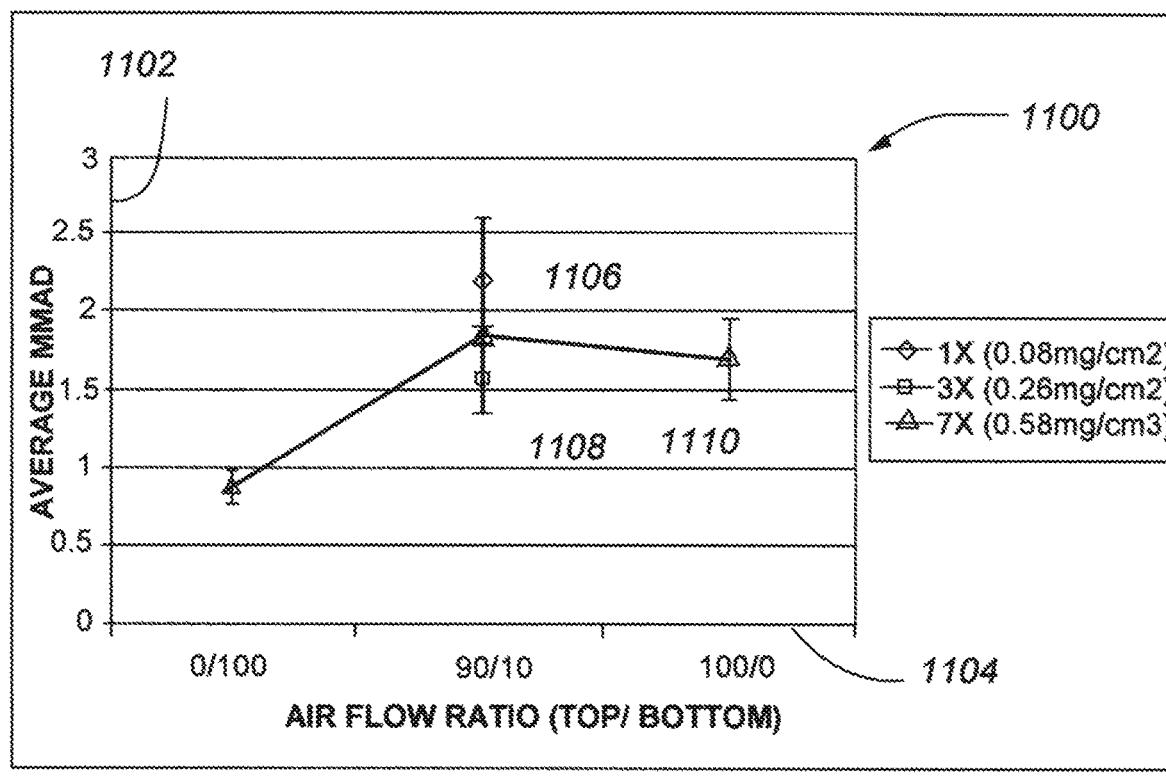
FIG. 11 is a plot showing average MMAD as a function of air flow ratio (across:bottom) for bumetanide free base vaporized from a perforated 316 stainless substrates.

The data presented in Table 10 are illustrated graphically in FIG. 11, which is a plot 1100 of average MMAD 902 as a function of air flow ratio (across:bottom) 1104. Curves 1106, 1108, and 1110 represent drug coating densities of 0.08, 0.26, and 0.58 mg/cm$^2$, respectively.

The data shown in Table 10 and FIG. 11 substantiate the previous findings that the particle size (MMAD) decreases as the proportion of the air flow coming through the substrate is increased, due to increased mixing of drug with the air.

Example 4

Vardenafil condensation aerosols were produced by the substrate screening apparatus using perforated stainless steel substrates. The substrates were spray-coated with a 20 mg/mL solution of vardenafil free base (isolated from the HCl trihydate salt available from Bosche Scientic, LLC, New Brunswick, N.J.) in dichloromethane/methanol (3:1 volume:volume) at drug coating densities of 0.112, 0.334, and 0.883 mg/cm$^2$ (approximate coating thickness: 1.12, 3.34, and 8.83 μm). Total air flow rate was 28.3 liters/minute. Various airflow ratios and vaporization temperatures were evaluated.

Table 11 presents aerosol purity data as a function of drug film thickness, substrate temperature, and air flow ratio for aerosolization of vardenafil from a perforated 316 stainless steel substrate (n=3 for each condition tested, unless otherwise indicated).

TABLE 11

Aerosol Purity of Vardenafil Aerosolized from Perforated Stainless Steel Substrates

| Drug Film Thickness (μm) | Coat | Aerosol Purity (%) Air Flow Ratio (Across:Bottom) | | | | | |
|---|---|---|---|---|---|---|---|
|  |  | 100:0 | | | 75:25 | | |
|  |  | Substrate Temperature (° C.) | | | | | |
|  | Control | 350 | 400 | 425 | 350 | 400 | 425 |
| 1.12 | 98.9 * | 95.3 | 95.3 | 95.0 | 97.0 | 96.6 | 96.6 |
| 3.34 | 98.8 * | 92.5 | 88.9 | 88.7 | 95.8 | 95.7 | 95.6 |
| 8.83 | 98.9 * | 89.5 | 83.2 ** | 80.8 | 96.1 | 93.2 | 93.3 |

* n = 4.
** n = 2.

In general, greater vardenafil drug purities were obtained with a 75:25 (across:bottom) air flow ratio than with a 100:0 air flow ratio. Aerosol purities were observed to decrease as the drug film thickness was increased. This effect was more pronounced with the 100:0 air flow ratio than with the 75:25 air flow ratio. Aerosol purity also tends to decrease as the substrate temperature during aerosolization was increased.

Table 12 presents aerosolized drug yield data as a function of drug film thickness, substrate temperature, and air flow ratio for aerosolization of vardenafil from a perforated 316 stainless steel substrate (n=3 for each condition tested, unless otherwise indicated).

TABLE 12

Drug Yield of Vardenafil Aerosolized from Perforated Stainless Steel Substrates

| Drug | Aerosolized Drug Yield (%) Air flow ratio (Across:bottom) | | | | | |
|---|---|---|---|---|---|---|
| Film Thickness | 100:0 | | | 75:25 | | |
| | Substrate Temperature (° C.) | | | | | |
| (μm) | 350 | 400 | 425 | 350 | 400 | 425 |
| 1.12 | 78.1 | 73.1 | 72.3 | 91.8 | 95.2 | 98.9 |
| 3.34 | 70.8 * | 68.8 | 67.6 | 89.1 | 86.5 | 84.2 |
| 8.83 | 33.6 ** | 48.2 | 50.9 | 47.1 ** | 89.2 | 85.4 |

* n = 1.
** n = 2.

As with drug purities (shown in Table 12), greater vardenafil drug yields were obtained with a 75:25 (across:bottom) air flow ratio than with a 100:0 air flow ratio. Aerosolized drug yields were also seen to decrease as the drug film thickness was increased. Again, this effect was less pronounced with the 75:25 air flow ratio than with the 100:0 air flow ratio.

In summary, the 75:25 (across:bottom) air flow ratio produced good results in terms of both aerosol purity and drug yield for vardenafil aerosolized from a perforated 316 stainless steel substrate. At aerosolization temperatures of 350° C., both aerosol purity and yield were good with the 75:25 air flow ratio and a drug film thickness of less than 3.3 μm. At substrate temperatures of 400° C. and 425° C., both aerosol purity and yield were very similar with either the 75:25 or 100:0 air flow ratios.

Example 5

Tadalafil condensation aerosols were produced by the substrate screening apparatus using perforated stainless steel substrates. The substrates were spray-coated with a 20 mg/mL solution of tadalafil free-base (isolated from the HCl trihydate salt available from Bosch Scientific, LLC, New Brunswick, N.J.) in dichloromethane/methanol (3:1 volume: volume) at drug coating densities of 0.236, 0.604, and 1.17 mg/cm$^2$ (approximate coating thickness: 2.36, 6.04, and 11.7 μm). Total air flow rate was 28.3 liters/minute. Various airflow ratios and vaporization temperatures were evaluated.

Table 13 presents aerosol purity data as a function of drug film thickness, substrate temperature, and air flow ratio for aerosolization of tadalafil from a perforated 316 stainless steel substrate (n=3 for each condition tested, unless otherwise indicated).

TABLE 13

Aerosol Purity of Tadalafil Aerosolized from Perforated Stainless Steel Substrates

| Drug Film | | Aerosol Purity (%) Air Flow Ratio (Across:Bottom) | | | | | | | |
|---|---|---|---|---|---|---|---|---|---|
| Thick-ness | Coat | 100:0 | | | | 75:25 | | | |
| | | Substrate Temperature (° C.) | | | | | | | |
| (μm) | Control | 325 | 350 | 375 | 400 | 325 | 350 | 375 | 400 |
| 2.36 | 99.9 * | 97.8 | 98.0 | 97.4 | 97.8 | 99.2 | 98.9 | 98.8 | 99.0 |
| 6.04 | 99.9 * | 98.6 | 96.2 | 95.1 | 93.2 | 98.8 | 98.6 | 97.9 | 97.2 |
| 11.70 | 99.9 * | — | 92.6 | 87.5 | 84.0 | — | 97.0 | 96.0 | 95.1 |

* n = 4.

As with vardenafil, greater tadalafil drug purities were obtained with a 75:25 (across:bottom) air flow ratio than with a 100:0 air flow ratio. Aerosol purities were also seen to decrease as the drug film thickness was increased. Again, this effect was much more pronounced with the 100:0 air flow ratio than with the 75:25 air flow ratio. Aerosol purity also tended to decrease as the substrate temperature during aerosolization was increased.

Table 14 presents drug yield data as a function of drug film thickness, substrate temperature, and air flow ratio for aerosolization of tadalafil from a perforated 316 stainless steel substrate (n=3 for each condition tested, unless otherwise indicated).

TABLE 14

Drug Yield of Tadalafil Aerosolized from Perforated Stainless Steel Substrates

| Drug | Aerosolized Drug Yield (%) Air Flow Ratio (Across:Bottom) | | | | | | | |
|---|---|---|---|---|---|---|---|---|
| Film Thickness | 100:0 | | | | 75:25 | | | |
| | Substrate Temperature (° C.) | | | | | | | |
| (μm) | 325 | 350 | 375 | 400 | 325 | 350 | 375 | 400 |
| 2.36 | 76.6 | 81.1 | 89.1 | 88.9 | 73.5 | 99.0 | 95.2 | 99.7 |
| 6.04 | 25.7 * | 66.9 | 60.4 | 76.6 | 26.1 | 40.2 | 85.3 * | 96.8 |
| 11.70 | — | 58.2 | 69.0 | 78.7 | — | 68.0 | 80.6 | 80.2 |

* n = 2.

As with vardenafil, greater tadalafil drug yields were obtained with a 75:25 (across:bottom) air flow ratio than with a 100:0 air flow ratio. Aerosolized drug yields were also seen to decrease as the drug film thickness is increased. Again, this effect was more pronounced with the 100:0 air flow ratio than with the 75:25 air flow ratio. In general, higher substrate temperatures during aerosolization tended to result in greater drug yields.

In summary, the 75:25 (across:bottom) air flow ratio produced good results in terms of both aerosol purity and drug yield for tadalafil aerosolized from a perforated 316 stainless steel substrate. The 100:0 air flow ratio resulted in lower drug yields (<85%), even at substrate temperatures of 400° C. The 75:25 air flow ratio, at substrate temperatures of 350° C. and drug film thicknesses of 11.7 μm or more, resulted in drug yields less than 70%. Substrate temperatures of 375° C. and 400° C. result in yields of about 80%. The 75:25 air flow ratio, at substrate temperatures of 375° C. and drug film thicknesses of 11.7 μm, resulted in good drug yields and drug purities of about 96%.

Example 6

Fentanyl condensation aerosols were produced by the substrate screening apparatus using non-perforated polyimide film (KAPTON® polyimide film, available from DuPont, Wilmington, Del.). The substrates were spray-coated with fentanyl free base.

Figure 12:
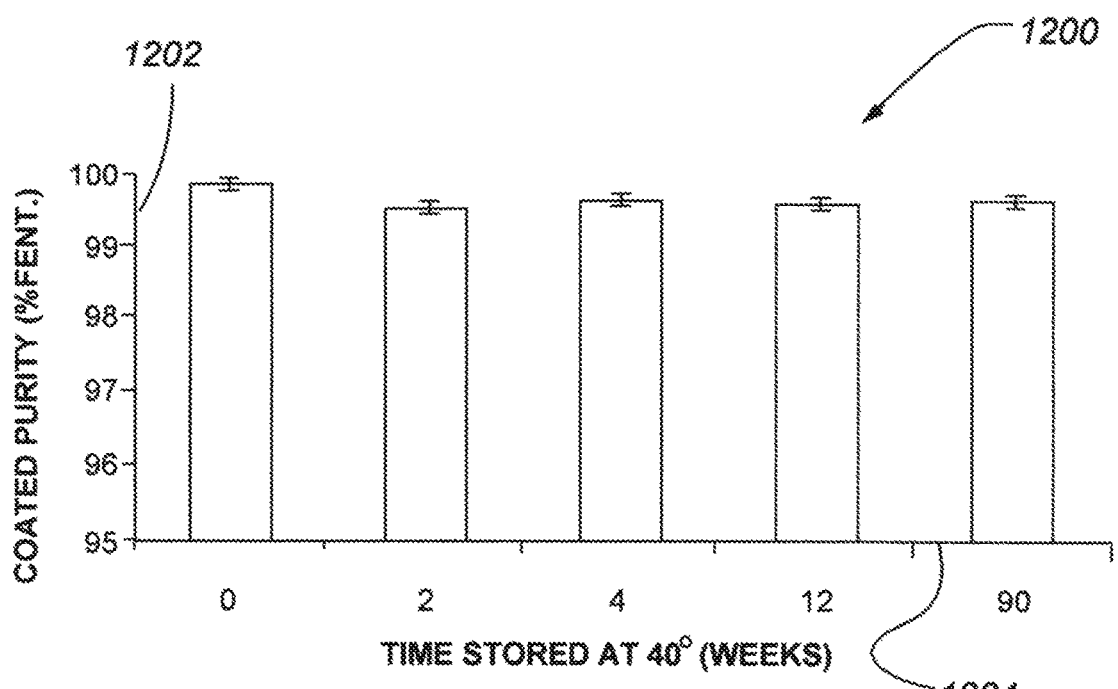
FIG. 12 is a bar graph showing coated purity at various storage times (weeks) at 40° C. for fentanyl free base coated on polyimide film.

Aerosol purity of the coated drug was measured by HPLC initially (storage time 0) and at various time intervals up to 90 weeks. FIG. 12 is a bar graph 1200 showing aerosol purity (%) 1202 of a fentanyl-coated polyimide film as a function of storage time 1204 at 40° C. The aerosol purity of fentanyl coated onto polyimide film remained very high (~99.7%) after 90 weeks storage.

Example 7

Prochlorperazine condensation aerosols were produced by the substrate screening apparatus using perforated polyimide film (KAPTON® polyimide film, available from DuPont, Wilmington, Del.). Copper heater traces were formed on one surface of a sheet of polyimide film. Holes were formed between the heater traces by chemical etching. The polyimide film heating units were spray-coated on the polyimide film surface with a 25 mg/mL solution of prochlorperazine free base (available from Industria Chimica Milanese, Milano, Italy) in acetone. Total air flow rate was 28.3 liters/minute. Various airflow ratios were evaluated.

Figure 13:
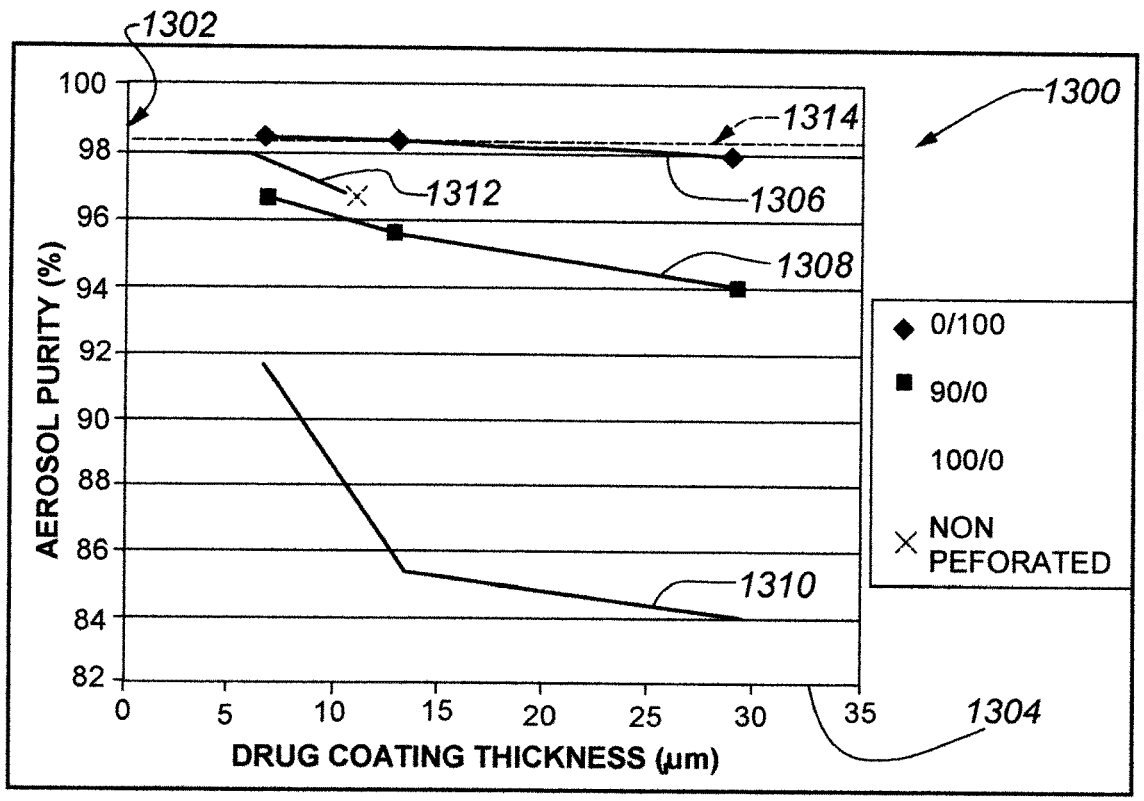
FIG. 13 is a plot showing aerosol purity (%) as a function of drug coating thickness (microns) at various air flow ratios (across:bottom) for prochlorperazine free base using a perforated polyimide film substrate.

The aerosol purity of prochlorperazine aerosolized from perforated polyimide film heating units was measured at various drug coating thicknesses and air flow ratios of 0:100, 90:10, and 100:0 across:bottom. FIG. 13 is a plot 1300 showing aerosol purity (%) 1302 of prochlorperazine at various drug coating thicknesses 1304. Curves 1306, 1308, and 1310 represent across:bottom air flow ratios of 0:100, 90:10, and 100:0, respectively. As a control, curve 1312 represents aerosolization of prochlorperazine from a non-perforated 304 stainless steel substrate. Dotted line 1314 represents the coated aerosol purity.

As previously observed with aerosolization of various drugs from perforated stainless steel substrates, as the percentage of air flow coming from under the bottom side of the substrate increased, aerosol purity level also increased, and a greater drug coating thickness can be used. When 100% of the air flow came through the substrate, aerosol purity levels of 98% or greater were obtained up to at least 30 μm drug coating thickness.

The coated aerosol purity was compared with the aerosol purity of prochlorperazine vaporized from polyimide film substrates having "small" and "large" holes (refer to FIGS. 2A and 2B). Drug coating thickness was 14 μm; total air flow was set at 30 liters/minute. The data from this set of experiments are shown in Table 15, below.

TABLE 15

Vaporization of Prochlorperazine from Perforated Polyimide Film Substrates

| Coated Aerosol | Small Holes Air Flow Ratio (Across:Bottom) | | Large Holes Air Flow Ratio (Across:Bottom) | |
|---|---|---|---|---|
| Purity (%) | 100:0 | 75:25 | 100:0 | 75:25 |
| 98.85 | 94.8 | 97.4 | 97.1 | 97.7 |

For the heaters with the small holes, aerosol purity declined from 97.4% to 94.8% as the air flow coming across the substrate was increased from 75% to 100%. For the large-hole heaters, there was no significant difference in aerosol purity as the relative amount of air flow coming across the substrate was increased. It is believed that the higher than expected aerosol purity coming from the large-holed substrates with 100% across air flow may be due to the presence of air flowing through the heater elements, even though no air is directly routed up from the bottom of the substrate.

Example 8

Adenosine condensation aerosols were produced by the substrate screening apparatus using perforated polyimide film substrates. The substrates were spray-coated with adenosine free base at various coating densities. Various airflow ratios and vaporization temperatures were evaluated.

Figure 14:
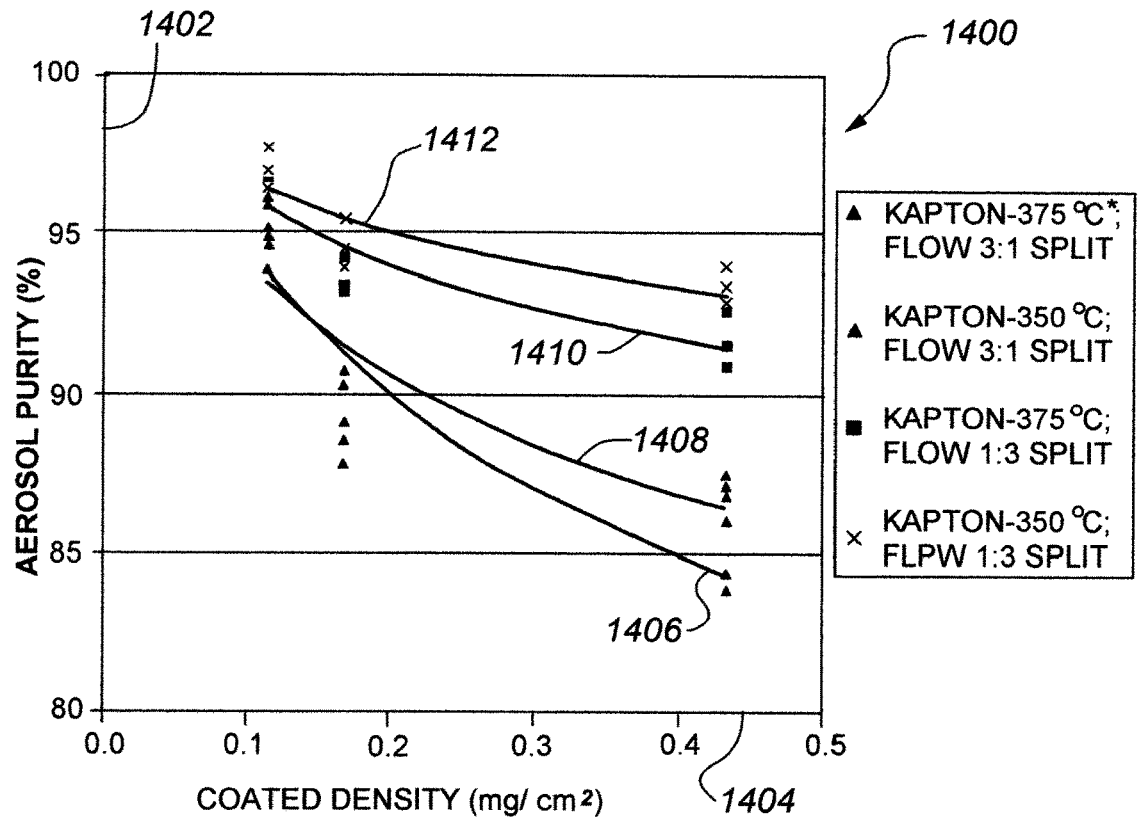
FIG. 14 is a plot showing aerosol purity (%) as function of coated density ($mg/cm^2$) at various air flow ratios and temperatures for adenosine free base using a perforated polyimide film substrate.

FIG. 14 is a plot 1400 showing aerosol purity (%) 1402 of aerosolized adenosine free base as a function of drug coating density (mg/cm$^2$) 1404. Curves 1406 and 1408 represent an across:bottom air flow ratio of 3:1 (21:7 liters per minute) and vaporization temperatures of 375° C. and 350° C., respectively. Curves 1410 and 1412 represent an across:bottom air flow ratio of 1:3 (7:21 LPM) and vaporization temperatures of 375° C. and 350° C., respectively.

As can be seen from the data presented in plot 1400, greater aerosol purities were achieved using lower (350° C. as opposed to 375° C.) vaporization temperatures and greater air flow thorough the substrate as opposed to across the substrate. Aerosol purity showed a decrease with increases in drug coating density.

Example 9

Baclofen condensation aerosols were produced by the substrate screening apparatus using perforated polyimide film substrates. The substrates were spray-coated with baclofen free base at various coating densities. Various air flow ratios and vaporization temperatures were evaluated.

Figure 15:
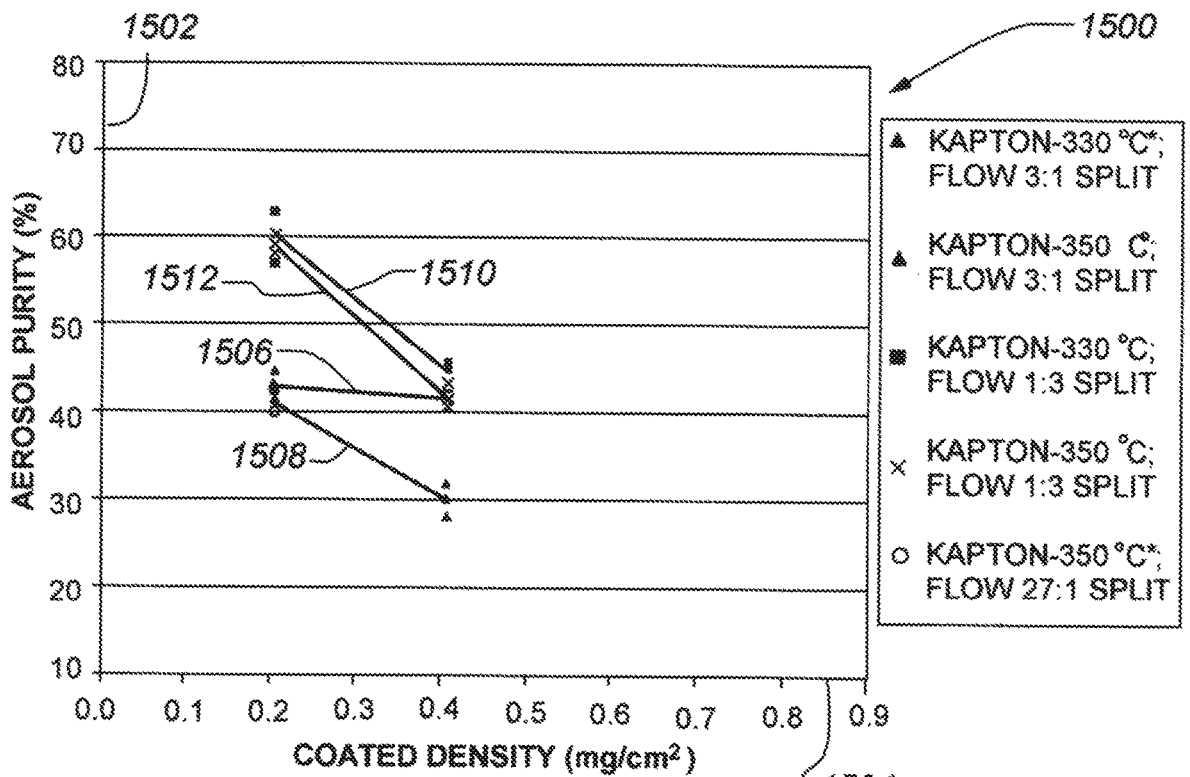
FIG. 15 is a plot showing aerosol purity (%) as function of coated density ($mg/cm^2$) at various air flow ratios and temperatures for baclofen free base using a perforated polyimide film substrate.

FIG. 15 is a plot 1500 showing aerosol purity (%) 1502 of aerosolized baclofen free base as a function of drug coating density (mg/cm$^2$) 1504. Curves 1506 and 1508 represent an across:bottom air flow ratio of 3:1 (21:7 LPM) and vaporization temperatures of 330° C. and 350° C., respectively. Curves 1510 and 1512 represent an across: bottom air flow ratio of 1:3 (7:21 LPM) and vaporization temperatures of 330° C. and 350° C., respectively. Data points 1514 represent an across:bottom air flow ratio of 27:1 and a vaporization temperature of 350° C.

As can be seen from the data presented in plot 1500, greater aerosol purities were achieved using lower (330° C. as opposed to 350° C.) vaporization temperatures and greater air flow through the substrate as opposed to across the substrate. Very poor drug purities of around 20% were obtained when nearly all of the air flow was directed across the substrate (27:1 ratio). Aerosol purity showed a decrease with increases in drug coating density.

Example 10

Ciclesonide condensation aerosols were produced by the substrate screening apparatus using perforated polyimide film substrates and non-perforated heat-passivated stainless steel substrates. The substrates were spray-coated with ciclesonide free base at various coating densities. Various air flow ratios and vaporization temperatures were evaluated.

Figure 16:
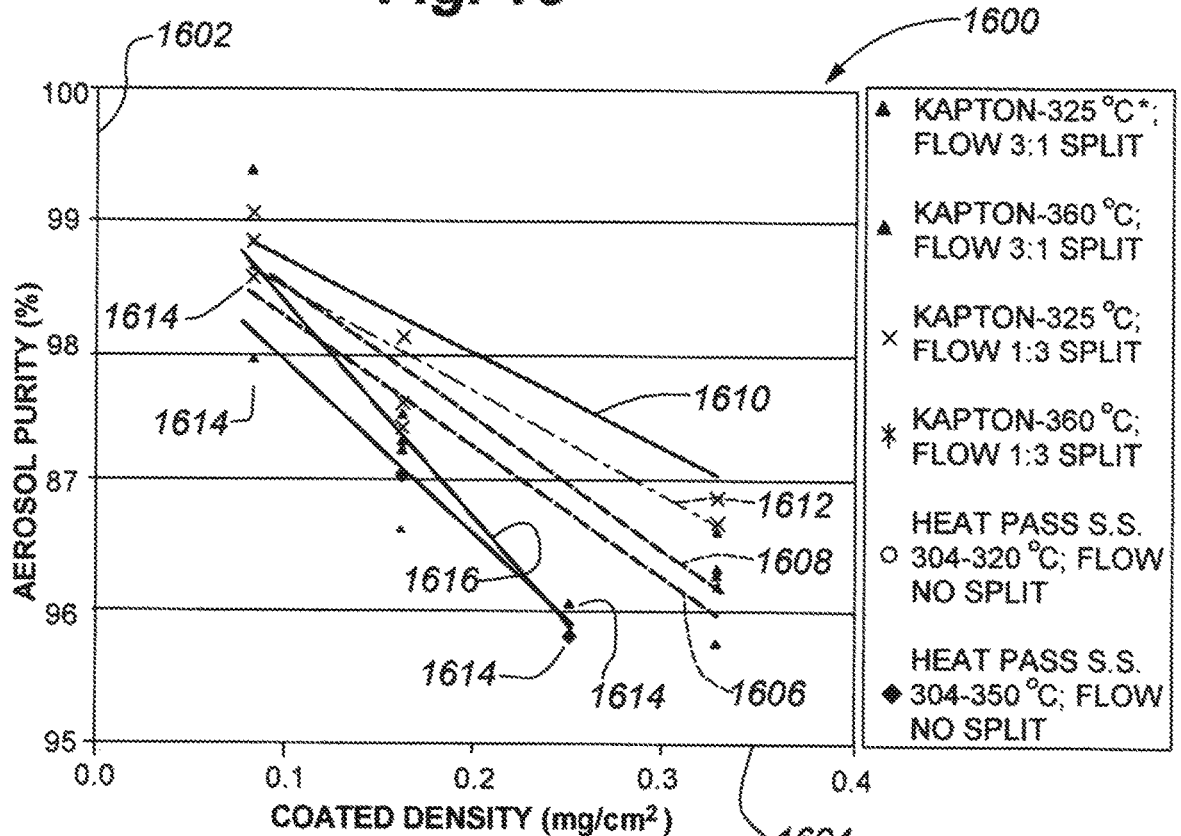
FIG. 16 is a plot showing aerosol purity (%) as function of coated density ($mg/cm^2$) at various air flow ratios and temperatures for ciclesonide free base using a perforated polyimide film substrate and a non-perforated, heat-passivated stainless steel substrate.

FIG. 16 is a plot 1600 showing aerosol purity (%) 1602 of aerosolized ciclesonide free base as a function of drug coating density (mg/cm$^2$) 1604. Curves 1606, 1608, 1610, and 1612 show aerosol purity data for drug vaporized from perforated polyimide film substrates. Curves 1606 and 1608 represent an across:bottom air flow ratio of 3:1 (21:7 LPM) and vaporization temperatures of 325° C. and 360° C., respectively. Curves 1610 and 1612 represent an across: bottom air flow ratio of 1:3 (7:21 LPM) and vaporization temperatures of 325° C. and 360° C., respectively.

Curves 1614 and 1616 show aerosol purity data for drug vaporized from non-perforated heat-passivated 304 stainless steel substrates, with no air flow ratio (i.e., 100% of the air flow was directed across the substrate). Curves 1614 and 1616 represent vaporization temperatures of 320° C. and 350° C., respectively.

As can be seen from the data in plot 1600, greater aerosol purities were achieved using greater air flow through substrate as opposed to across the substrate. Greater aerosol purities were achieved using lower vaporization temperatures (325° C. as opposed to 360° C.) for the perforated polyimide film substrates with the 1:3 air flow ratio. This trend was slightly reversed for the perforated polyimide film substrates with the 3:1 air flow ratio. Aerosol purity decreased with increases in drug coating density. This trend was particularly observed with the stainless steel substrates.

Example 11

Cyclobenzaprine fumarate condensation aerosols were produced by the substrate screening apparatus using perforated polyimide film substrates. The substrates were spray-coated with cyclobenzaprine fumarate at various coating densities. Various air flow ratios and vaporization temperatures were evaluated.

Figure 17:
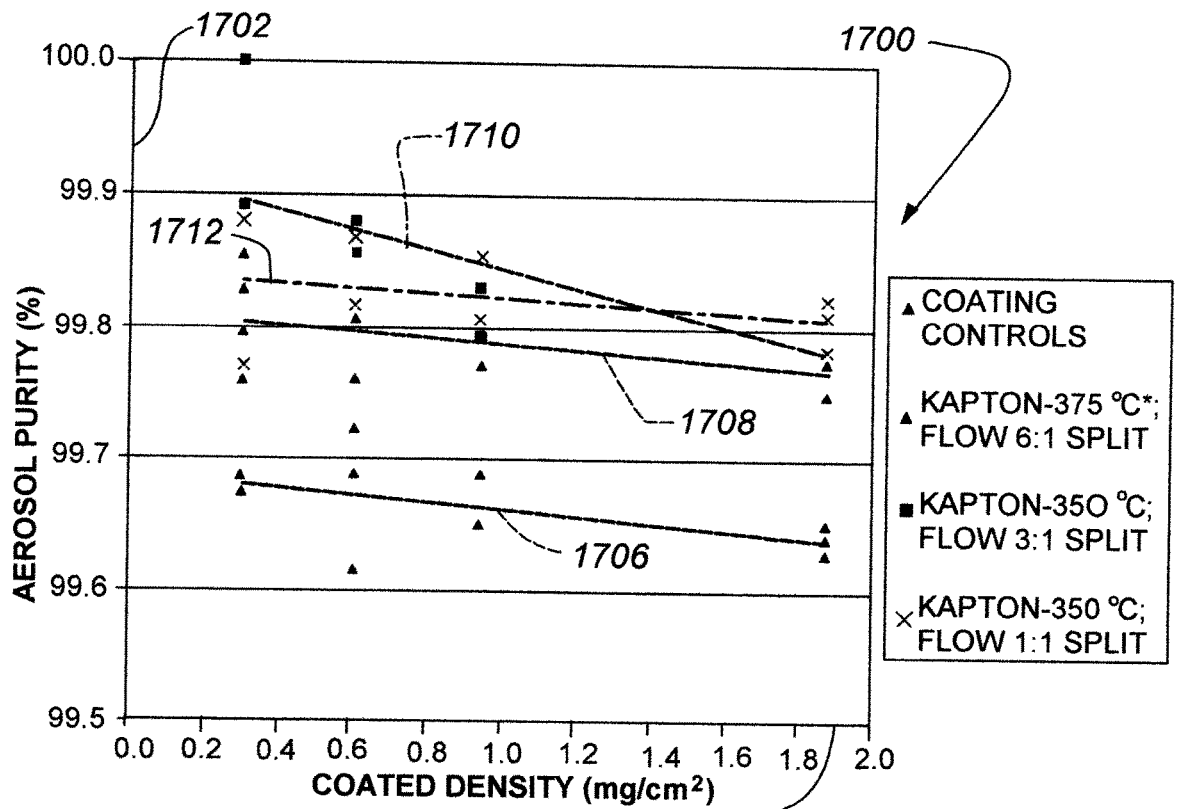
FIG. 17 is a plot showing aerosol purity (%) as function of coated density ($mg/cm^2$) at various air flow ratios and temperatures for cyclobenzaprine fumarate using a perforated polyimide film substrate.

FIG. 17 is a plot 1700 showing aerosol purity (%) 1702 of aerosolized cyclobenzaprine fumarate as a function of drug coating density (mg/cm$^2$) 1704. Curve 1706 represents a drug coating control. Curve 1708 represents an across:bottom air flow ratio of 6:1 (24:4 LPM) and a vaporization temperature of 375° C. Curve 1710 represents an across:bottom air flow ratio of 3:1 (21:7 LPM) and a vaporization temperature of 350° C. Curve 1712 represents an across:bottom air flow ratio of 1:1 (14:14 LPM) and a vaporization temperature of 350° C.

As can be seen from the data presented in plot 1700, all three test conditions provided excellent (>99.7%) aerosol purities. In general, aerosol purities improved using lower (350° C. as opposed to 375° C.) vaporization temperatures and greater air flow through the substrate as opposed to across the substrate. Best results were achieved using a vaporization temperature of 350° C. and an air flow ratio of 3:1, although this set of test conditions was slightly more sensitive to increases in drug coating density. In general, although aerosol purity showed a decrease with increases in drug coating density, this effect was not significant at any of the test conditions.

Example 12

Diphenhydramine fumarate condensation aerosols were produced by the substrate screening apparatus using perforated polyimide film substrates and non-perforated heat-passivated stainless steel substrates. The substrates were spray-coated with diphenhydramine fumarate at various coating densities. Various air flow ratios and vaporization temperatures were evaluated.

Figure 18:
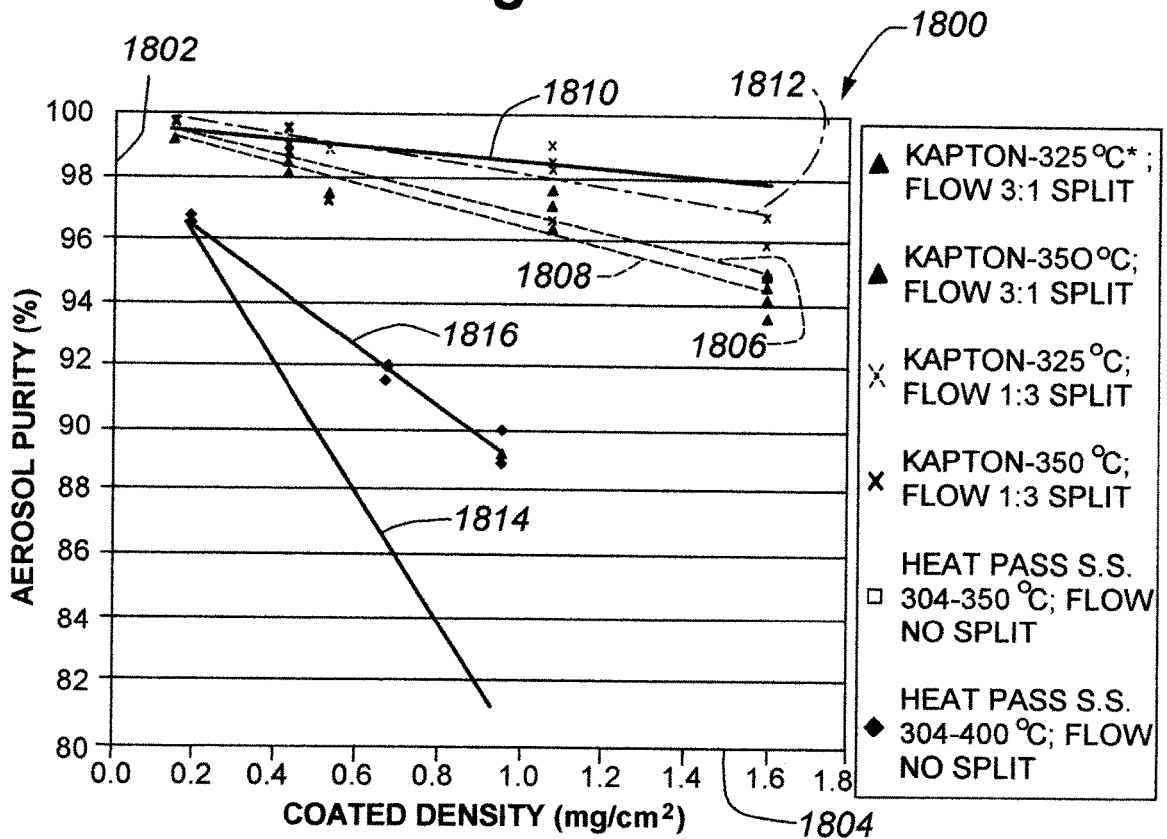
FIG. 18 is a plot showing aerosol purity (%) as function of coated density ($mg/cm^2$) at various air flow ratios and temperatures for diphenhydramine fumarate using a perforated polyimide film substrate and a non-perforated, heat-passivated stainless steel substrate.

FIG. 18 is a plot 1800 showing aerosol purity (%) 1802 of aerosolized diphenhydramine fumarate as a function of drug coating density (mg/cm$^2$) 1804. Curves 1806, 1808, 1810, and 1812 show aerosol purity data for drug vaporized from perforated polyimide film substrates. Curves 1806 and 1808 represent an across:bottom air flow ratio of 3:1 (21:7 LPM) and vaporization temperatures of 325° C. and 350° C., respectively. Curves 1810 and 1812 represent an across:bottom air flow ratio of 1:3 (7:21 LPM) and vaporization temperatures of 325° C. and 350° C., respectively.

Curves 1814 and 1986 show aerosol purity data for drug vaporized from non-perforated heat-passivated 304 stainless steel substrates, with no air flow ratio (i.e., 100% of the air flow was directed across the substrate). Curves 1814 and 1816 represent vaporization temperatures of 350° C. and 400° C.

As can be seen from the data presented in plot 1800, greater aerosol purities were achieved using lower vaporization temperatures (325° C. as opposed to 350° C.) and greater air flow through the substrate as opposed to across the substrate. For the polyimide film substrates, aerosol purity showed some decrease with increases in drug coating density. This trend was particularly observed with the stainless steel substrates.

Example 13

Flunisolide condensation aerosols were produced by the substrate screening apparatus using perforated polyimide film substrates, perforated heat-passivated stainless steel substrates, and perforated SULFINERT-treated stainless steel substrates. (SULFINERT is an amorphous silicon. The SULFINERT-treated stainless steel substrates were obtained from Restek Corp., Bellefonte, Pa.) The substrates were spray-coated with flunisolide free base at various coating densities. All samples were tested using an across:bottom air flow ratio of 3:1 (21:7 LPM). Various vaporization temperatures were evaluated.

Figure 19:
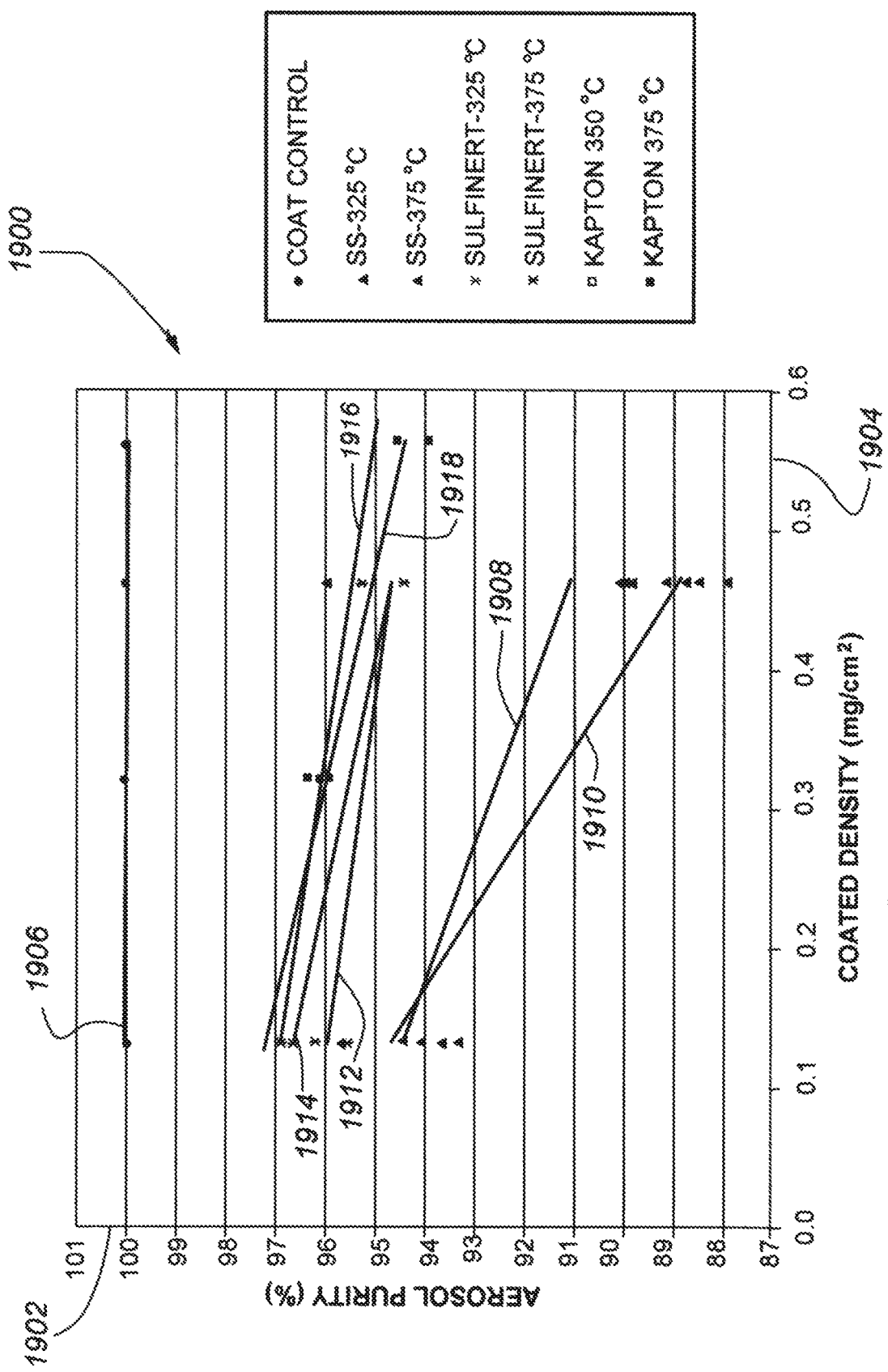
FIG. 19 is a plot showing aerosol purity (%) as function of coated density ($mg/cm^2$) at various air flow ratios and temperatures for flunisolide free base using a perforated polyimide film substrate, a perforated, heat-passivated stainless steel substrate, and a perforated SULFINERT®-treated stainless steel substrate.

FIG. 19 is a plot 1900 showing aerosol purity (%) 1902 of aerosolized flunisolide free base as a function of drug coating density (mg/cm$^2$) 1904. Curve 1906 represents a drug coating control. Curves 1908 and 1910 show aerosol purity data for drug vaporized from perforated heat-passivated 316 stainless steel substrates at vaporization temperatures of 325° C. and 375° C., respectively. Curves 1912 and 1914 show aerosol purity data for drug vaporized from perforated SULFINERT-treated 316 stainless steel substrates at vaporization temperatures of 325° C. and 375° C., respectively. Curves 1916 and 1918 show aerosol purity data for drug vaporized from perforated polyimide film substrates at vaporization temperatures of 350° C. and 375° C., respectively.

As can be seen from the data presented in plot 1900, for the polyimide film substrates and the SULFINERT-treated stainless steel substrates, increased vaporization temperature had little effect on aerosol purity. For the heat-passivated stainless steel substrates, aerosol purities showed a significant decrease with increases in vaporization temperature at the higher drug coating density densities.

Example 14

Fluticasone propionate condensation aerosols were produced by the substrate screening apparatus using perforated polyimide film substrates and non-perforated heat-passivated stainless steel substrates. The substrates were spray-coated with fluticasone propionate at various coating densities. Various air flow ratios and vaporization temperatures were evaluated.

Figure 20:
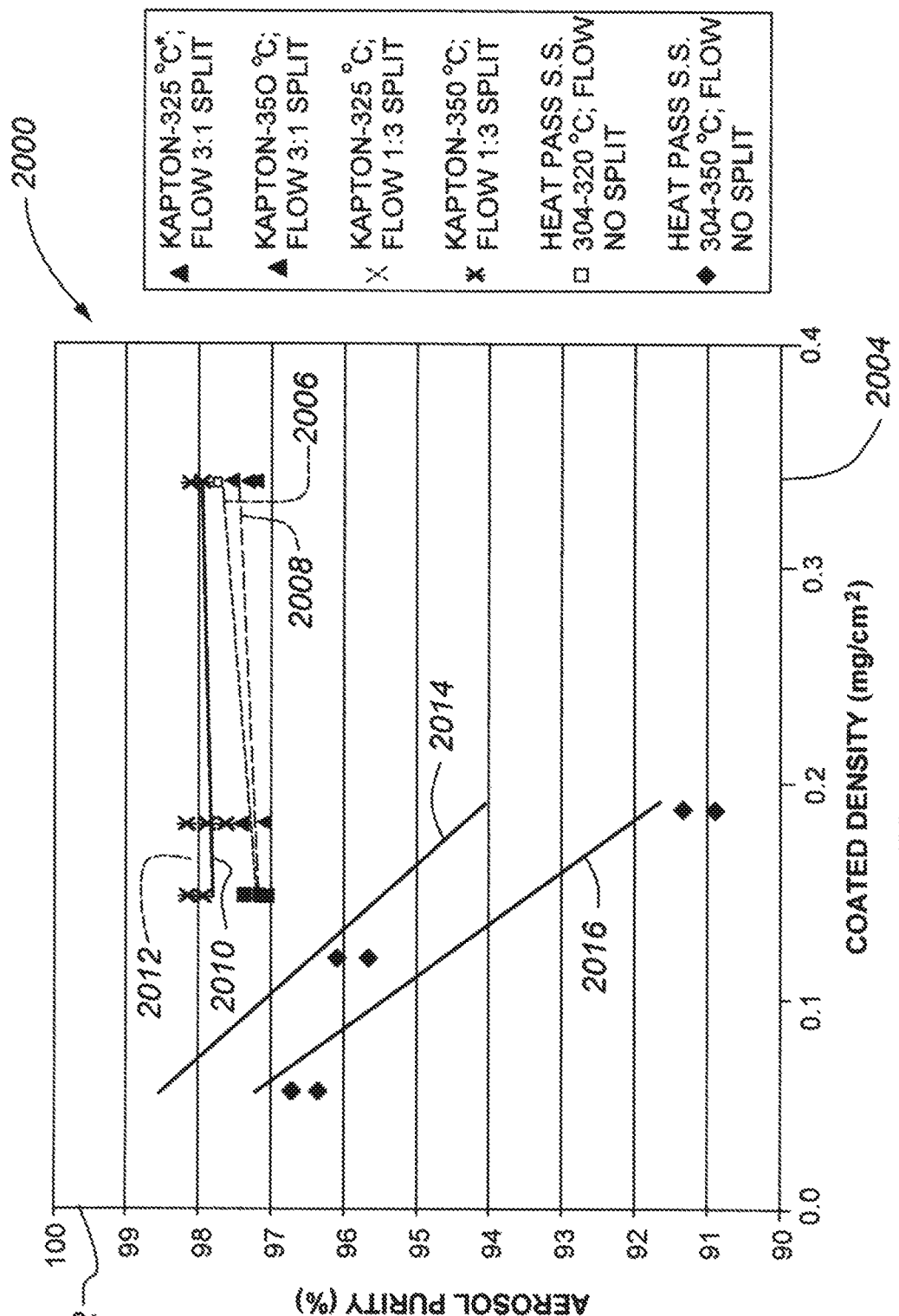
FIG. 20 is a plot showing aerosol purity (%) as function of coated density ($mg/cm^2$) at various air flow ratios and temperatures for fluticasone propionate using a perforated polyimide film substrate and a non-perforated, heat-passivated stainless steel substrate.

FIG. 20 is a plot 2000 showing aerosol purity (%) 2002 of aerosolized fluticasone propionate as a function of drug coating density (mg/cm$^2$) 2004. Curves 2006, 2008, 2010, and 2012 show aerosol purity data for drug vaporized from perforated polyimide film substrates. Curves 2006 and 2008 represent an across:bottom air flow ratio of 3:1 (21:7 LPM) and vaporization temperatures of 325° C. and 350° C., respectively. Curves 2010 and 2012 represent an across:bottom air flow ratio of 1:3 (7:21 LPM) and vaporization temperatures of 325° C. and 350° C., respectively.

Curves 2014 and 2016 show aerosol purity data for drug vaporized from non-perforated heat-passivated 304 stainless steel substrates, with no air flow ratio (i.e., 100% of the air flow was directed across the substrate). Curves 2014 and 2016 represent vaporization temperatures of 320° C. and 350° C., respectively.

As can be seen from the data presented in plot 2000, for the polyimide film substrates, all four test conditions provided excellent (>97%) aerosol purities. For this particular drug aerosolized from polyimide film substrates, neither vaporization temperature nor air flow ratio appeared to have a significant effect on aerosol purity. For the stainless steel substrates, greater drug purities were obtained at lower vaporization temperatures. Drug coating density had a significant effect on aerosol purities for drug vaporized from the stainless steel substrates.

Example 15

Mometasone fumarate condensation aerosols were produced by the substrate screening apparatus using perforated polyimide film substrates, non-perforated heat-passivated stainless steel substrates, and non-perforated SULFINATE-treated stainless steel substrates. The substrates were spray-coated with mometasone fumarate at various coating densities. The polyimide film samples were evaluated using an across:bottom air flow ratio of 3:1 (21:7 LPM). The stainless steel samples were evaluated with no air flow ratio. Various vaporization temperatures were evaluated.

Figure 21:
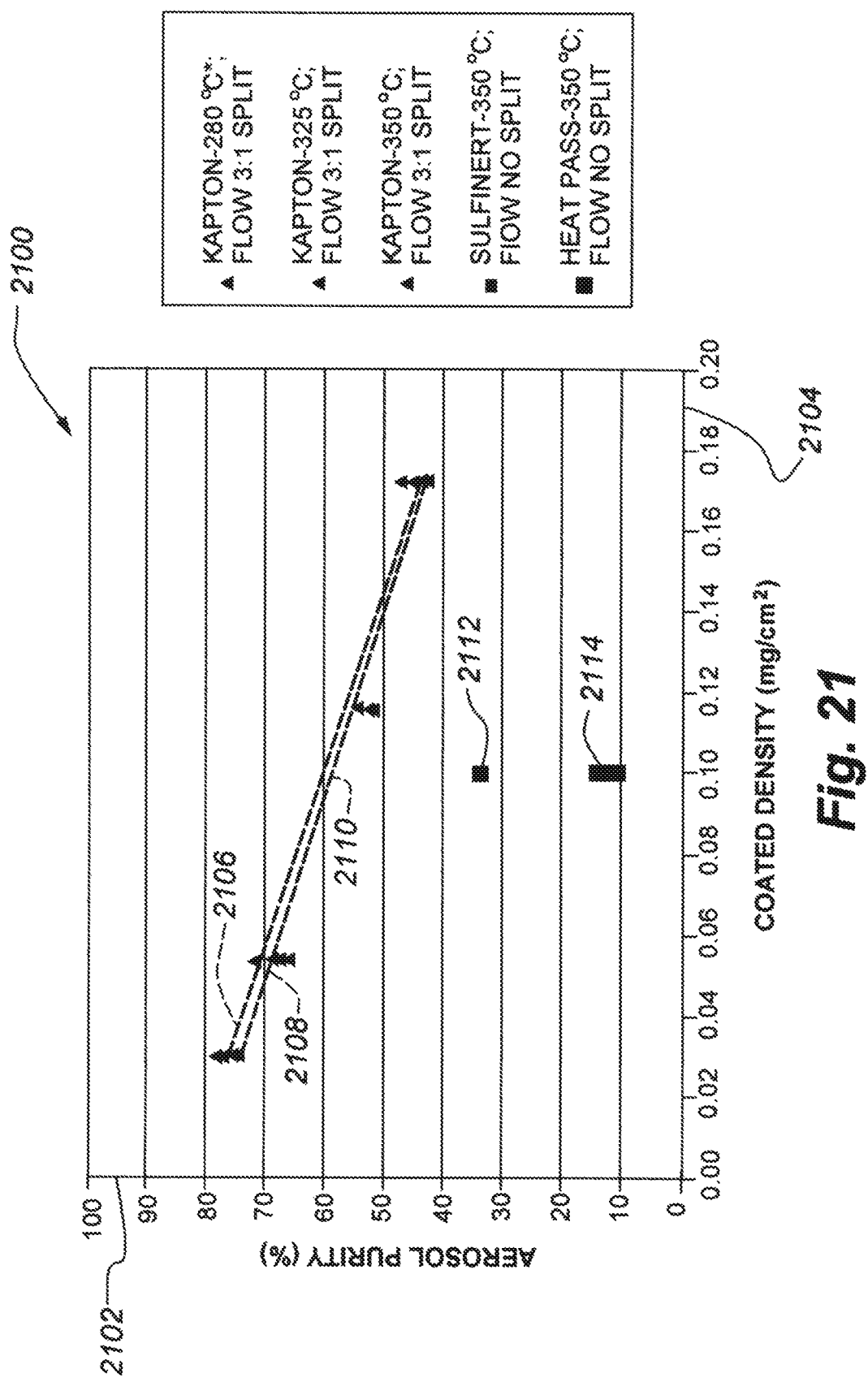
FIG. 21 is a plot showing aerosol purity (%) as function of coated density ($mg/cm^2$) at various air flow ratios and temperatures for mometasone furoate using a perforated polyimide film substrate, a non-perforated, heat-passivated stainless steel substrate, and a non-perforated SULFINERT®-treated stainless steel substrate.

FIG. 21 is a plot 2100 showing aerosol purity (%) 2102 of aerosolized mometasone fumarate as a function of drug coating density (mg/cm$^2$) 2104. Curves 2106, 2108, and 2110 show aerosol purity data for drug vaporized from perforated polyimide film substrates at vaporization temperatures of 280° C., 325° C., and 375° C., respectively. Data point 2112 shows aerosol purity data for drug vaporized from non-perforated SULFINERT-treated stainless steel 304 substrates at a vaporization temperature of 350° C. Data point 2114 shows aerosol purity data for drug vaporized from non-perforated heat-passivated stainless steel 304 substrates at a vaporization temperature of 350° C.

As can be seen from the data presented in plot 2100, for the polyimide film substrates, increased vaporization temperature had little effect on aerosol purity. On the other hand, drug coating density had a significant effect on aerosol purity. Aerosol purities for both the SULFINERT-treated and heat-passivated stainless steel substrates were poor.

Example 16

Paroxetine fumarate condensation aerosols were produced by the substrate screening apparatus using perforated polyimide film substrates and non-perforated heat-passivated stainless steel substrates. The substrates were spray-coated with paroxetine fumarate at various coating densities. Various air flow ratios and vaporization temperatures were evaluated.

Figure 22:
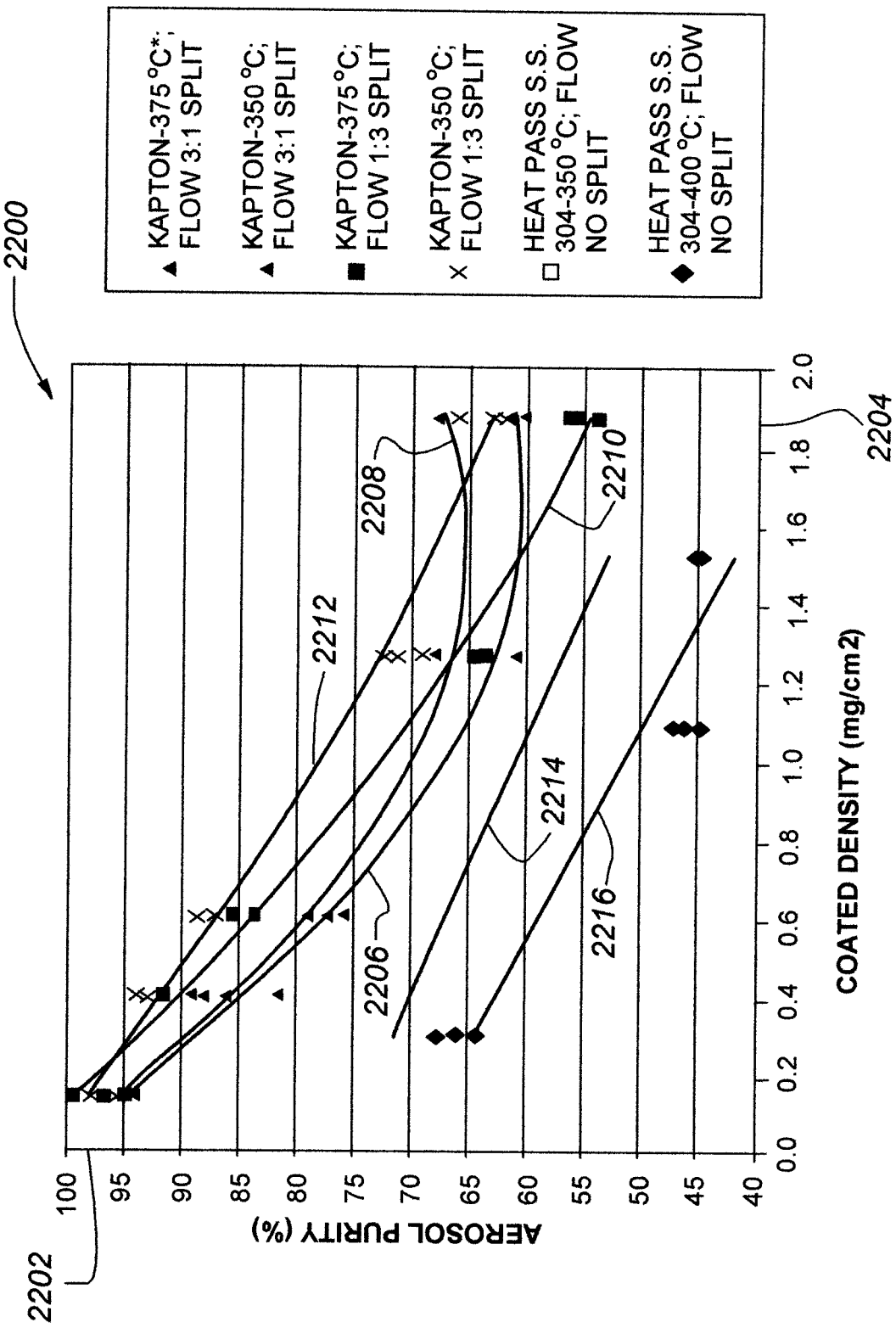
FIG. 22 is a plot showing aerosol purity (%) as function of coated density ($mg/cm^2$) at various air flow ratios and temperatures for paroxetine fumarate using a perforated polyimide film substrate and non-perforated, heat-passivated stainless steel substrate.

FIG. 22 is a plot 2200 showing aerosol purity (%) 2202 of aerosolized paroxetine fumarate as a function of drug coating density (mg/cm$^2$) 2204. Curves 2206, 2208, 2210, and 2212 show aerosol purity data for drug vaporized from perforated polyimide film substrates. Curves 2206 and 2208 represent an across:bottom air flow ratio of 3:1 (21:7 LPM) and vaporization temperature of 375° C. and 350° C., respectively. Curves 2210 and 2212 represent an across:bottom air flow ratio of 1:3 (7:21 LPM) and vaporization temperatures of 375° C. and 350° C., respectively.

Curves 2214 and 2216 show aerosol purity data for drug vaporized from non-perforated heat-passivated 304 stainless steel substrates, with no air flow ratio (i.e., 100% of the air flow was directed across the substrate). Curves 2214 and 2216 represent vaporization temperatures of 320° C. and 400° C., respectively.

As can be seen from the data presented in plot 2200, for the polyimide film substrates, greater aerosol purities were achieved using lower vaporization temperatures (350° C. as opposed to 375° C.) and greater air flow through the substrate as opposed to across the substrate. The stainless steel substrates provided poor aerosol purities in general. For both the polyimide film and stainless steel substrates, aerosol purities decreased with increases in drug coating density.

Example 17

Tadalafil condensation aerosols were produced by the substrate screening apparatus using perforated heat-passivated stainless steel substrates. The substrates were spray-coated with tadalafil free base at various coating densities. Various air flow ratios and vaporization temperatures were evaluated.

Figure 23:
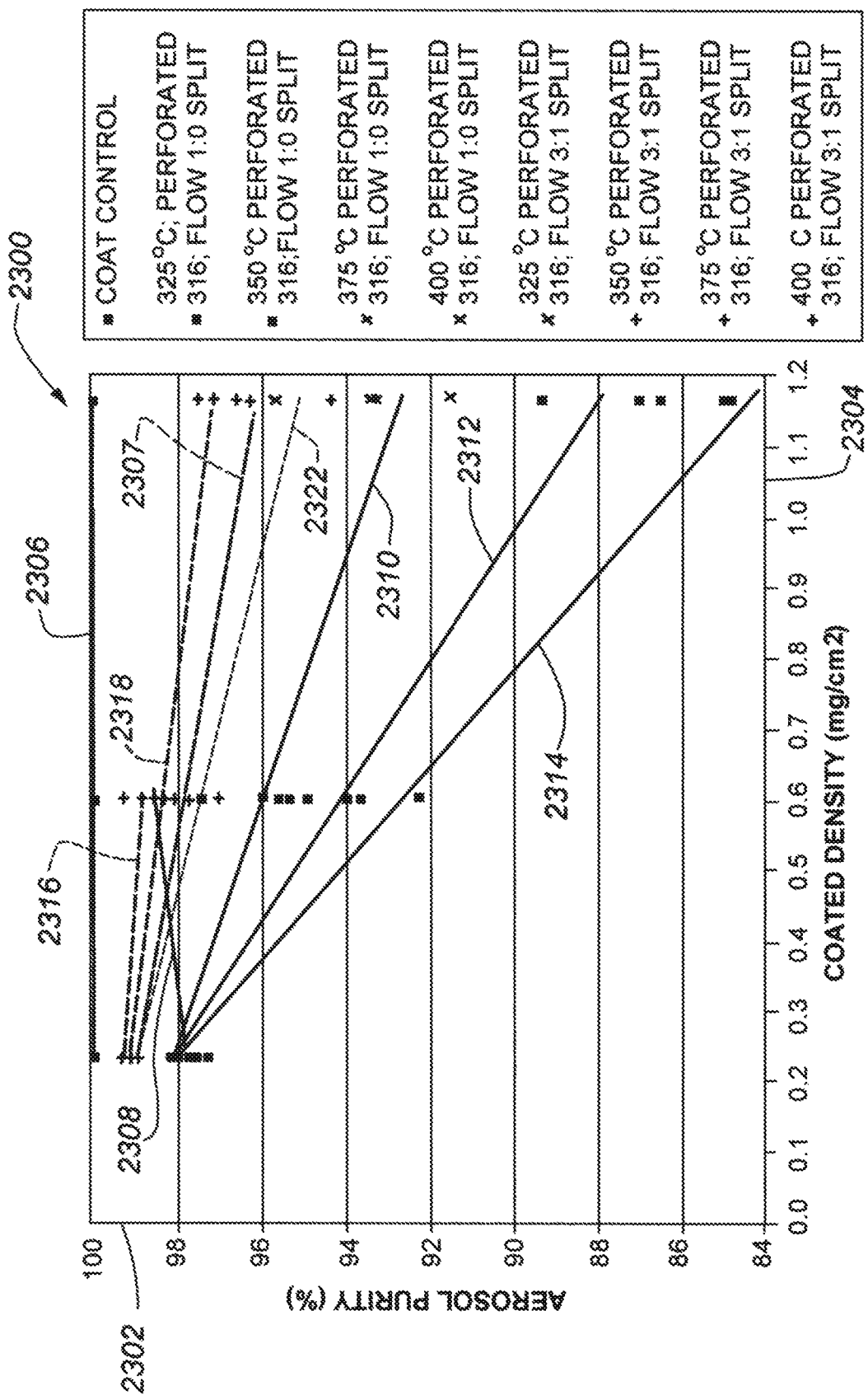
FIG. 23 is a plot showing aerosol purity (%) as function of coated density (mg/cm$^2$) at various air flow ratios and temperatures for tadalafil free base using a perforated, heat-passivated stainless steel substrate.

FIG. 23 is a plot 2300 showing aerosol purity 2302 of aerosolized tadalafil free base as a function of drug coating density (mg/cm$^2$) 2304. Curve 2306 represents a drug coating control. Curves 2308, 2310, 2312, and 2314 represent an across:bottom air flow ratio of 1:0 (27:0 LPM) and vaporization temperatures of 325° C., 350° C., 375° C., and 400° C., respectively. Curves 2316, 2318, 2320, and 2322 represent an across:bottom air flow ratio of 3:1 (21:7 LPM) and vaporization temperatures of 325° C., 350° C., 375° C., and 400° C., respectively.

As can be seen from the data presented in plot 2300, greater aerosol purities were achieved using lower vaporization temperatures and greater air flow through the substrate as opposed to across the substrate. Although, in general, aerosol purities dropped as drug coating density increased, this effect was especially pronounced at the 1:0 air flow ratio.

Example 18

Tizanadine condensation aerosols were produced by the substrate screening apparatus using perforated polyimide film substrates, non-perforated heat-passivated stainless steel substrates, and non-perforated non-passivated stainless steel substrates. The substrates were spray-coated with tizanadine free base at various coating densities. Various air flow ratios and vaporization temperatures were evaluated.

Figure 24:
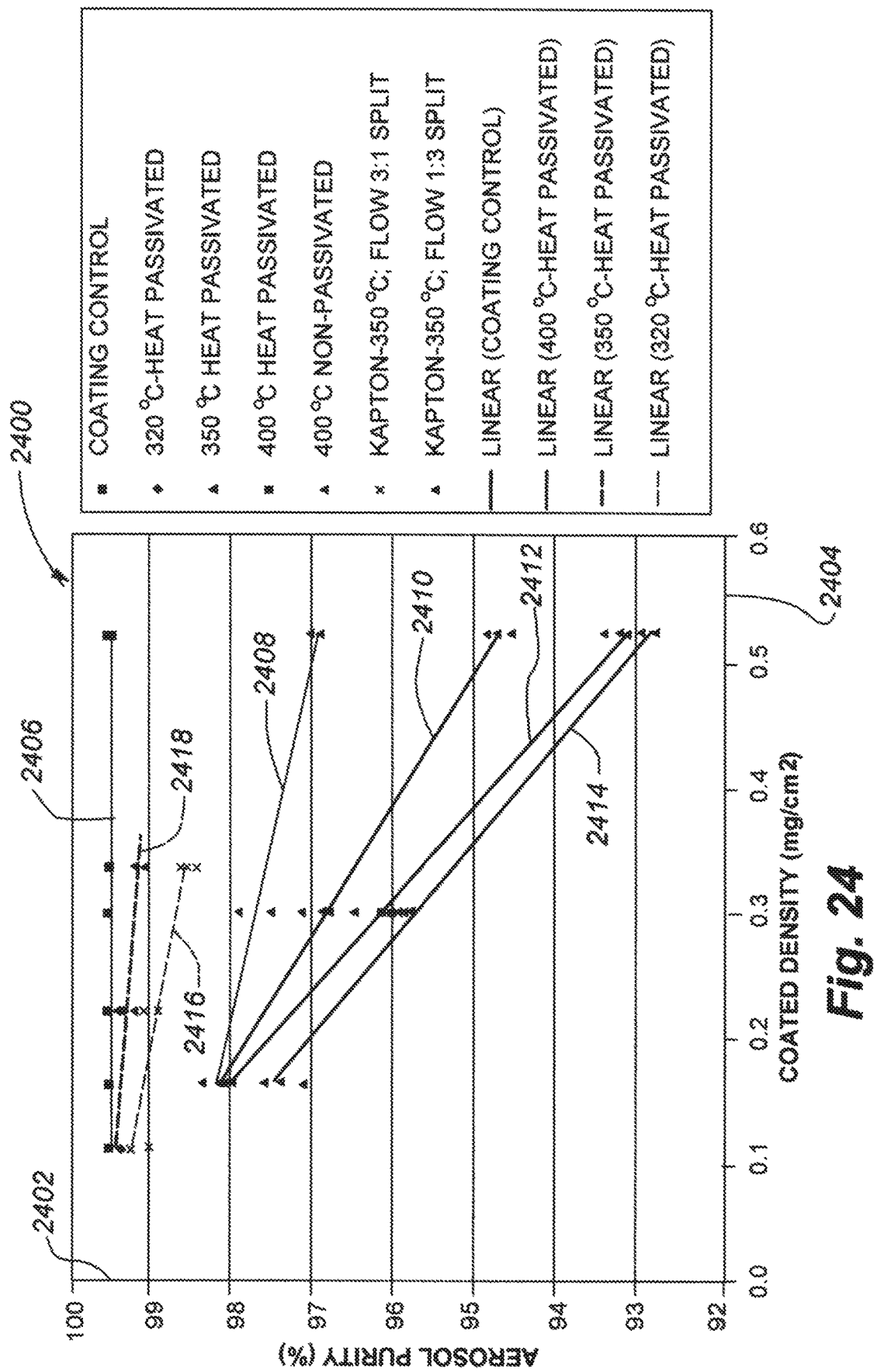
FIG. 24 is a plot showing aerosol purity (%) as function of coated density (mg/cm$^2$) at various air flow ratios and temperatures for tizanadine free base using a perforated polyimide film substrate, a non-perforated, heat-passivated stainless steel substrate, and a non-perforated, (non-heat-passivated) stainless steel substrate.

FIG. 24 is a plot 2400 showing aerosol purity (%) 2402 of aerosolized tizanadine free base as a function of drug coating density (mg/cm$^2$) 2404. Curve 2406 represents the drug coating control. Curves 2408, 2410, and 2412 show aerosol purity data for drug vaporized from non-perforated heat-passivated 304 stainless steel substrates, with no air flow ratio and vaporization temperatures of 320° C., 350° C., and 400° C., respectively. Curve 2414 shows aerosol purity data for drug vaporized from non-perforated non-passivated 304 stainless steel substrates, with no air flow ratio and a vaporization temperature of 400° C.

Curves 2416 and 2418 show aerosol purity data for drug vaporized from perforated polyimide film substrates. Curves 2416 and 2418 represent across:bottom air flow ratios of 3:1 (21:7 LPM) and 1:3 (7:21 LPM), respectively, and a vaporization temperature of 350° C.

As can be seen from the data presented in plot 2400, both of the polyimide film samples showed excellent (>98%) aerosol purity, regardless of the air flow ratio. For the heat-passivated stainless steel substrates, aerosol purity declined with increases in vaporization temperature and drug coating density. The non-passivated stainless steel substrates performed most poorly of all.

Example 19

Vardenafil condensation aerosols were produced by the substrate screening apparatus using perforated polyimide film substrates and perforated heat-passivated stainless steel substrates. The substrates were spray-coated with vardenafil free base at various coating densities. Various air flow ratios and vaporization temperatures were evaluated.

Figure 25:
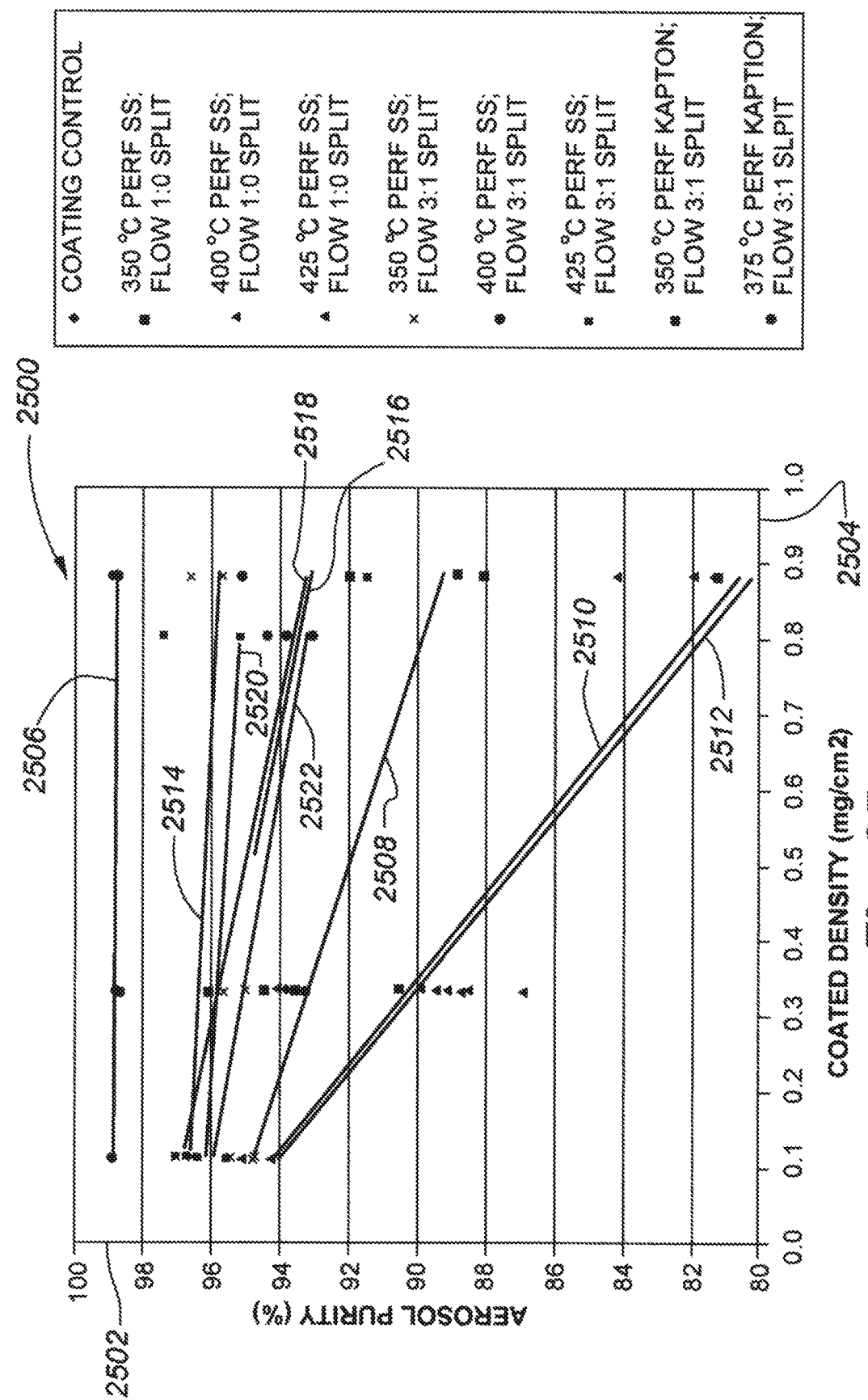
FIG. 25 is a plot showing aerosol purity (%) as function of coated density (mg/cm$^2$) at various air flow ratios and temperatures for vardenafil free base using a perforated polyimide film substrate and a perforated, heat-passivated stainless steel substrate.

FIG. 25 is a plot 2500 showing aerosol purity (%) 2502 of aerosolized vardenafil free base as a function of drug coating density (mg/cm$^2$) 2504. Curve 2506 represents a drug coating control. Curves 2508, 2510, and 2512 show aerosol purity data for drug vaporized from perforated heat-passivated 316 stainless steel substrates, at an across:bottom air flow ratio of 1:0 and vaporization temperatures of 350° C., 400° C., and 425° C., respectively. Curves 2514, 2516, and 2518 show aerosol purity data for drug vaporized from perforated heat-passivated 316 stainless steel substrates, at an across:bottom air flow ratio of 3:1 (21:7 LPM) and vaporization temperatures of 350° C., 400° C., and 425° C., respectively.

Curves 2520 and 2522 show aerosol purity data for drug vaporized from perforated polyimide film substrates, at an across:bottom air flow ratio of 3:1 (21:7 LPM) and vaporization temperatures of 350° C. and 375° C., respectively.

As can be seen from the data presented in plot 2500, the greatest aerosol purities were obtained at an air flow ratio of 3:1 and vaporization temperature of 350° C., for both the polyimide film and stainless steel substrates. These conditions also showed very little sensitivity to increases in drug coating density. Worst results were obtained with the stainless steel substrates at an air flow ratio of 1:0 and vaporization temperatures of 400° C. and 425° C. Under these conditions, a decrease in aerosol purity with increasing drug coating density was observed.

Example 20

Zaleplon condensation aerosols were produced by the substrate screening apparatus using perforated polyimide film substrates and non-perforated heat-passivated stainless steel substrates. The substrates were spray-coated with zaleplon free base at various coating densities. Various air flow ratios and vaporization temperatures were evaluated.

Figure 26:
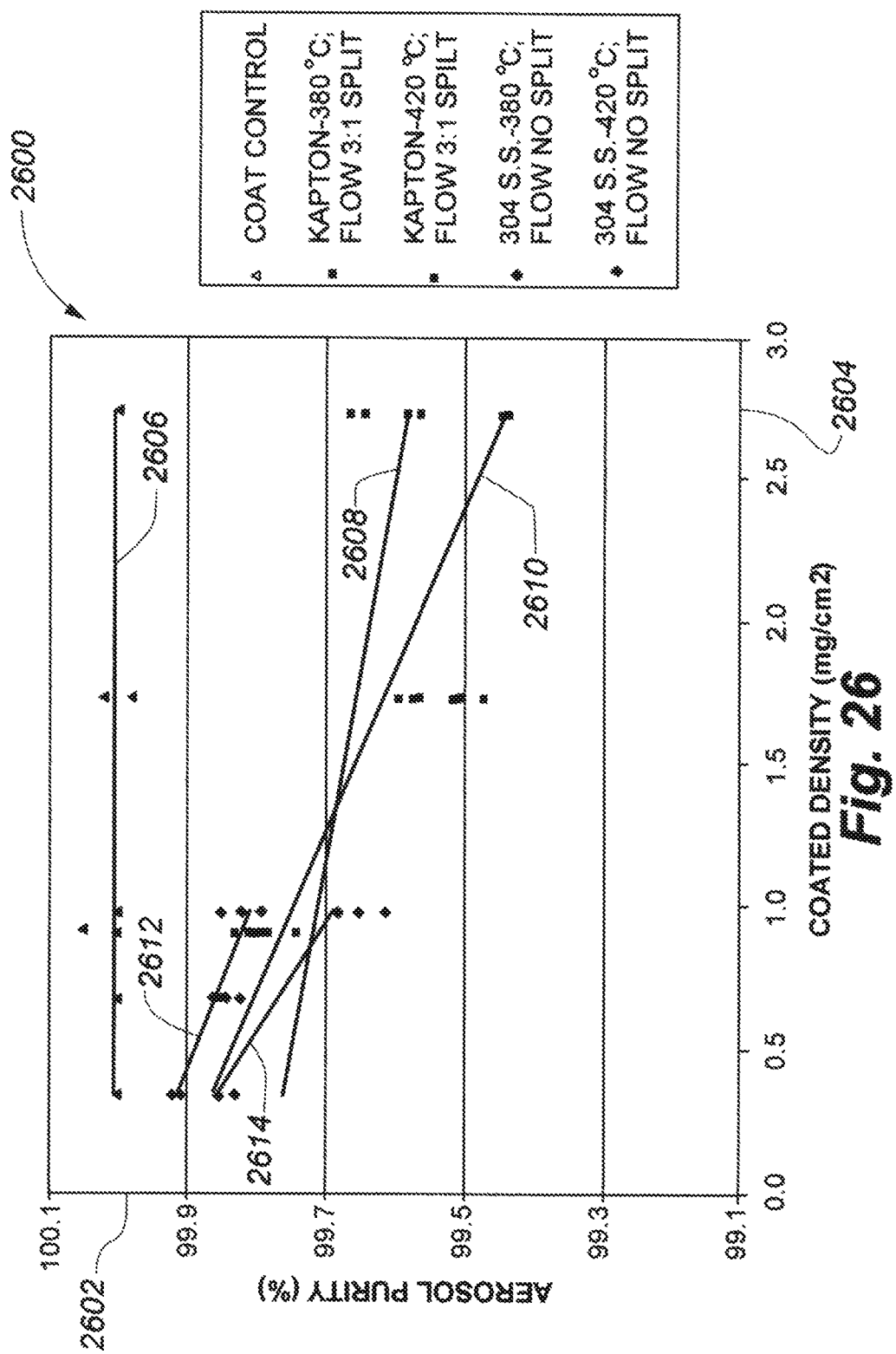
FIG. 26 is a plot showing aerosol purity (%) as function of coated density (mg/cm$^2$) at various air flow ratios and temperatures for zaleplon free base using a perforated polyimide film substrate and a non-perforated, heat-passivated stainless steel substrate.

FIG. 26 is a plot 2600 showing aerosol purity (%) 2602 of aerosolized zaleplon free base as a function of drug coating density (mg/cm$^2$) 2604. Curve 2606 represents a drug coating control. Curves 2608 and 2610 show aerosol purity data for drug vaporized from perforated polyimide film substrates, at an across:bottom air flow ratio of 3:1 (21:7 LPM) and vaporization temperatures of 380° C. and 420° C., respectively. Curves 2612 and 2614 show aerosol purity data for drug vaporized from non-perforated heat-passivated stainless steel substrates, with no air flow ratio and vaporization temperatures of 380° C. and 420° C., respectively.

As can be seen from the data presented in plot 2600, all four test conditions provided excellent (>99.4%) aerosol purities. For this particular drug, neither vaporization temperature nor air flow ratio appeared to have a significant effect on aerosol purity, regardless of the substrate. Although aerosol purity decreased with increased drug coating density, this effect appeared to be minimal.

Example 21

Drug is dissolved or suspended in a solvent (e.g., dichloromethane or methanol). The solution or suspension is coated to about a 4 micron thickness on a stainless steel substrate of about 8 cm$^2$ surface area. The substrate may either be a standard stainless steel foil or a heat-passivated stainless steel foil. The substrate is heated to a temperature sufficient to generate a thermal vapor (generally ~350° C.) but at least to a temperature of 200° C. with an air flow typically of 20 L/min (1 m/s) passing over the film during heating. The heating is done in a volatilization chamber fitted with a trap (such as described in the Examples above). After vaporization is complete, airflow is discontinued and the resultant aerosol is analyzed for purity using the methods disclosed herein. If the resultant aerosol contains less than 10% drug degradation product, i.e., the TSR≥9, then the drug is a heat stable drug. If, however, at about 4 micron thickness, greater than 10% degradation is determined, the experiment is repeated at the same conditions, except that film thicknesses of about 1.5 microns, and of about 0.5 micron, respectively, are used. If a decrease in degradation products relative to the 4 micron thickness is seen at either of these thinner film thicknesses, a plot of film thickness versus purity is graphed and extrapolated out to a film thickness of 0.05 microns. The graph is used to determine if there exists a film thickness where the purity of the aerosol would be such that it contains less than 10% drug degradation products. If such a point exists on the graph, then the drug is defined as a heat stable drug.

Example 22

Drug (1 mg) is dissolved or suspended in a minimal amount of solvent (e.g., dichloromethane or methanol). The solution or suspension is pipetted onto the middle portion of a 3 cm by 3 cm piece of aluminum foil. The coated foil is wrapped around the end of a 1½ cm diameter vial and secured with parafilm. A hot plate is preheated to approximately 300° C., and the vial is placed on it foil side down. The vial is left on the hotplate for 10 s after volatilization or decomposition has begun. After removal from the hotplate, the vial is allowed to cool to room temperature. The foil is removed, and the vial is extracted with dichloromethane followed by saturated aqueous NaHCO$_3$. The organic and aqueous extracts are shaken together, separated, and the organic extract is dried over Na$_2$SO$_4$. An aliquot of the organic solution is removed and injected into a reverse-phase HPLC with detection by absorption of 225 nm light. A drug is preferred for aerosolization where the purity of the drug isolated by this method is greater than 85%. Such a drug has a decomposition index less than 0.15. The decomposition index is arrived at by subtracting the aerosol purity fraction (i.e., 0.85) from 1.

Although the invention has been described with respect to particular embodiments, it will be apparent to those skilled in the art that various changes and modifications can be made without departing from the invention. One of ordinary skill in the art can combine the foregoing embodiments or make various other embodiments and aspects of the method and device of the present invention to adapt them to specific usages and conditions. As such, these changes and modifications are properly, equitably, and intended to be within the full range of equivalents of the following claims.

We claim:

1. An aerosol drug delivery device comprising a drug supply unit comprising a perforated substrate, characterized in that the perforated substrate has a plurality of formed through holes, wherein air flows through said holes, and wherein at least a portion of the surface of the substrate is coated with a drug composition, wherein the substrate has a thickness, wherein the holes are circular and wherein the air flow is initiated by a user placing the device in his/her mouth then inhaling.

2. The aerosol drug delivery device of claim 1 further comprising a housing (152) defining an airway (164, 166), said drug supply unit being in communication with said airway and configured to heat the coated drug composition to a temperature sufficient to vaporize the drug composition.

3. The aerosol drug delivery device of claim 1 wherein the number of and spacing between the holes is sufficient that, when the drug composition is vaporized from the substrate, the vaporized drug exhibits a purity that is greater than the purity of a drug vaporized from a substrate that does not include a plurality of holes formed therethrough.

4. The drug delivery device of claim 1, wherein the substrate has a thickness of at least 0.00127 cm ($5.0 \times 10^{-4}$ inches).

5. The drug delivery device of claim 1, wherein the substrate has a thickness in the range of 0.00127 cm ($5.0 \times 10^{-4}$) to 0.0127 cm ($5.0 \times 10^{-3}$) inches.

6. The drug delivery device of claim 1, wherein the portion of the surface that is coated with a drug composition has a surface area in the range of 8 mm$^2$ to 20 cm$^2$.

7. The drug delivery device of claim 1, wherein the portion of the surface that is coated with a drug composition has a porosity in the range of 1% to 70%.

8. The drug delivery device of claim 1, wherein the substrate comprises a metal.

9. The drug delivery device of claim 8, wherein the metal is selected from the group consisting of stainless steel, aluminum, gold, copper, titanium, and combinations thereof.

10. The drug delivery device of claim 9, wherein the metal is stainless steel and wherein the stainless steel is heat-passivated.

11. The drug delivery device of claim 9, wherein the metal is stainless steel and wherein the stainless steel is amorphous silicon treated.

12. The drug delivery device of claim 1, wherein the substrate comprises a polymer.

13. The drug delivery device of claim 12, wherein the polymer is a polyimide film having a first surface and second surface, and wherein electrically conductive traces are formed on the first surface of the polyimide film substrate.

14. The drug delivery device of claim 1, wherein the plurality of holes comprises at least 10 holes.

* * * * *